United States Patent
Hakim et al.

(10) Patent No.: US 12,139,534 B2
(45) Date of Patent: Nov. 12, 2024

(54) METHODS AND COMPOSITIONS FOR DECREASING SOLUBLE IMMUNE RECEPTOR CD28

(71) Applicant: BIOND BIOLOGICS LTD., Misgav (IL)

(72) Inventors: Motti Hakim, Kibbutz Gazit (IL); Dror Alishekevitz, Kiryat Tivon (IL); Dana Haves Ziv, Karmiel (IL); Edna Meilin, Kfar Veradim (IL); Yair Sapir, Manof (IL); Avidor Shulman, Rakefet (IL); Tehila Ben-Moshe, Tel Aviv (IL); Ilana Mandel, Manof (IL)

(73) Assignee: BIOND BIOLOGICS LTD., Misgav (IL)

( * ) Notice: Subject to any disclaimer, the term of this patent is extended or adjusted under 35 U.S.C. 154(b) by 1077 days.

(21) Appl. No.: 16/980,409

(22) PCT Filed: Mar. 14, 2019

(86) PCT No.: PCT/IL2019/050292
§ 371 (c)(1),
(2) Date: Sep. 13, 2020

(87) PCT Pub. No.: WO2019/175885
PCT Pub. Date: Sep. 19, 2019

(65) Prior Publication Data
US 2021/0047411 A1 Feb. 18, 2021

Related U.S. Application Data

(60) Provisional application No. 62/643,334, filed on Mar. 15, 2018, provisional application No. 62/643,355, filed on Mar. 15, 2018, provisional application No. 62/774,254, filed on Dec. 2, 2018.

(51) Int. Cl.
| | | |
|---|---|---|
| A61K 45/06 | (2006.01) | |
| C07K 16/28 | (2006.01) | |
| G01N 33/574 | (2006.01) | |

(52) U.S. Cl.
CPC ...... C07K 16/2818 (2013.01); C07K 16/2827 (2013.01); G01N 33/57488 (2013.01); *A61K 45/06* (2013.01); *C07K 2317/55* (2013.01); *C07K 2317/565* (2013.01); *C07K 2317/569* (2013.01); *C07K 2317/622* (2013.01); *G01N 2333/70521* (2013.01); *G01N 2500/04* (2013.01)

(58) Field of Classification Search
CPC ............ C07K 16/2818; C07K 16/2827; C07K 2317/55; C07K 2317/565; C07K 2317/569; C07K 2317/622; C07K 2317/76; G01N 33/57488; G01N 2333/70521; G01N 2500/04; A61K 45/06; A61P 35/00

USPC ....................................................... 424/133.1
See application file for complete search history.

(56) References Cited

U.S. PATENT DOCUMENTS

2008/0038273 A1 2/2008 Soulillou et al.

FOREIGN PATENT DOCUMENTS

| CN | 100509849 C | 7/2009 |
|---|---|---|
| EP | 1378520 A1 | 1/2004 |
| JP | 2010195797 A | 9/2010 |
| WO | 2004096139 A2 | 11/2004 |
| WO | 2005066867 A2 | 7/2005 |
| WO | 2010009391 A1 | 1/2010 |
| WO | 2019175885 A1 | 9/2019 |

OTHER PUBLICATIONS

Byers, T. (CA Cancer Journal, 1999, 49: 353-361).*
Almagro & Fransson, Frontiers in Bioscience 2008; 13:1619-33.*
De Genst et al., Dev Comp Immunol 2006; 30:187-98.*
Yoshinaga et al., J. Biochem 2008; 143: 593-601.*
Daniel et al., "Costimulation With Agonistic Anti-CD28 Antibodies Prevents T Cell Apoptosis and is Required for Efficient Immunotherapy With CD3x19 Bispecific Antibodies in B Cell Lymphoma", Free communications and posters, Article 97, S42, 1997.
Hedemann et al., "ADAM17 inhibition enhances platinum efficiency in ovarian cancer", Oncotarget, vol. 9, No. 22, 16043-16058, 2018.
Huang et al., "Targeting the Sheddase Activity of ADAM17 by an Anti-ADAM17 Antibody D1(A12) Inhibits Head and Neck Squamous Cell Carcinoma Cell Proliferation and Motility via Blockage of Bradykinin Induced HERs Transactivation", International Journal of Biological Sciences, vol. 10 (7): 702-714, 2014.
Isitmangil et al., "Association of CTLA4 and CD28 Gene Variants and Circulating Levels of Their Proteins in Patients with Breast Cancer", in vivo, 30, 485-494, 2016.
Murray et al., "CD28-mediated pro-survival signaling induces chemotherapeutic resistance in multiple myeloma", Blood, vol. 123, No. 24, 3770-3779, 2014.
Hamzaoui et al., "Circulating soluble CD28 in patients with Behçet's disease: Relationship to clinical manifestations", Clinical and Experimental Rheumatology, 23 (Suppl. 38), S49-S52, 2005.
Hebbar et al., "Detection of circulating soluble CD28 in patients with systemic lupus erythematosus, primary Sjögren's syndrome and systemic sclerosis", Clinical and Experimental Immunology, 136, 388-392, 2004.

(Continued)

*Primary Examiner* — Yan Xiao
(74) *Attorney, Agent, or Firm* — The Roy Gross Law Firm, LLC; Roy Gross

(57) ABSTRACT

Methods of treating cancer and improving immunotherapies comprising decreasing soluble immune receptor levels are provided. Agents that bind membranal immune receptor and inhibit proteolytic cleavage of the receptor and agents that bind soluble immune receptor and that are neither receptor agonists nor antagonists are also provided, as are methods of producing these agents.

10 Claims, 33 Drawing Sheets
Specification includes a Sequence Listing.

(56) References Cited

OTHER PUBLICATIONS

Igawa et al., "Sweeping antibody as a novel therapeutic antibody modality capable of eliminating soluble antigens from circulation", Immunological Reviews, vol. 270, 132-151, 2016.

W.K. Ip, et al., "Plasma Concentrations of Soluble CTLA-4, CD28, CD80 and CD86 Costimulatory Molecules Reflect Disease Severity of Acute Asthma in Children", Pediatric Pulmonology 41, 674-682, 2006.

Sun et al., "Enhancement of soluble CD28 levels in the serum of Graves' disease", Central European Journal of Immunology, 39 (2), 216-222, 2014.

Wang et al., "Plasma sCD28, sCTLA-4 levels in neuromyelitis optica and multiple sclerosis during relapse", Journal of Neuroimmunology, 243, 52-55, 2012.

Wong et al., "Aberrant production of soluble costimulatory molecules CTLA-4, CD28, CD80 and CD86 in patients with systemic lupus erythematosus", Rheumatology, 44, 989-994, 2005.

Schroter et al., "A generic approach to engineer antibody pH-switches using combinatorial histidine scanning libraries and yeast display", mAbs., vol. 7, Issue 1, 138-151, 2015.

Yang et al., "Maximizing in vivo target clearance by design of pH-dependent target binding antibodies with altered affinity to FcRn", MABS, vol. 9, Issue 7, 1105-1117, 2017.

Kamphorst et al., "Rescue of exhausted CD8 T cells by PD-1-targeted therapies is CD28-dependent", Science, 355, 6332, 1423-1427, 2017.

Hui et al., "T cell costimulatory receptor CD28 is a primary target for PD-1-mediated inhibition", Science, 355, 6332, 1428-1433, 2017.

Magistrelli et al., "Identification of Three Alternatively Spliced Variants of Human CD28 mRNA", Biochemical and Biophysical Research Communications, 259, 34-37, 1999.

PCT Search Report for International Application No. PCT/IL2019/050292 mailed Jun. 17, 2019, 6 pp.

PCT Written Opinion for International Application No. PCT/IL2019/050292 mailed Jun. 17, 2019, 8 pp.

PCT Preliminary Report on Patentability for International Application No. PCT/IL2019/050292 dated Sep. 15, 2020, 9 pp.

Yunjie, Shi et al., "Expression and its significance of the membrane CD28 in cells and the serum level of soluble CD28 in elders" Abstract—Present day immunology, 2007, 27(1), pp. 38-40.

\* cited by examiner

METHODS AND COMPOSITIONS FOR DECREASING SOLUBLE IMMUNE RECEPTOR CD28

CROSS REFERENCE TO RELATED APPLICATIONS

This application is a National Phase of PCT Patent Application No. PCT/IL2019/050292 having International filing date of Mar. 14, 2019, which claims the benefit of priority under 35 U.S.C. § 119(e) of U.S. Provisional Patent Application No. 62/643,334, filed on Mar. 15, 2018, U.S. Provisional Patent Application No. 62/643,355, filed on Mar. 15, 2018, and U.S. Provisional Patent Application No. 62/774,254, filed on Dec. 2, 2018, the contents of which are all incorporated herein by reference in their entirety.

FIELD OF INVENTION

The present invention is in the field of immune regulation and immunotherapy.

BACKGROUND OF THE INVENTION

The adaptive immune system plays a critical role in the regulation and protection against pathogens and cancer cells, mainly by orchestrating the stimulation of antigen specific helper CD4+ and cytotoxic CD8+xT cells. Durable and persistent activation of T cells by antigen presenting cells (APC), involves i) engagement of the T cell receptor (TCR) with peptides presented by major histocompatibility complexes (MHCs) on APC; and ii) co-stimulatory CD28 receptors on T cells binding B7-1 (CD80) and B7-2 (CD86) ligands expressed also by the APC. The biological consequences of CD28 co-stimulation are numerous and include control of the T cell cycle, expansion, differentiation, as well as amplification of TCR stimulation by lowering the threshold needed for achieving immune effector function.

In contrast to the activating co-stimulatory molecule CD28, the structurally homolog, cytotoxic T lymphocyte associated 4 (CTLA-4), is an inhibitory co-stimulatory receptor, with membrane expression driven by the triggering of CD28. Both, CTLA-4 and CD28 are type I trans-membrane proteins. Their extracellular portion is composed with one V-set immunoglobulin super family (Ig-V) domain, which is homo-covalently linked by a cysteine residue located outside the IgV domain in proximity to the transmembrane region. Despite the resemblance, CTLA-4 and CD28 differ in terms of affinities and quaternary structural arrangements. CTLA-4 was found to have higher binding affinities to B7 molecules, and a different dimerization mode from CD28 resulting in dissimilar stoichiometric binding with the shared ligands. CD28 exhibits a mono-valent binding stoichiometry, while CTLA-4 interacts in a bivalent fashion. Hence, CTLA-4 binds B7 molecules with a much higher affinity and avidity than CD28 and consequently downregulates T cell responses and favors the onset of antigen specific tolerance.

It has been indicated that some co-stimulatory molecules have several physiological forms. Alongside membrane-bound forms, soluble forms have been described that are expressed in naive immune cells, increasing the complexity of T cell biology. The soluble form of CD28 (sCD28) has been ascribed to alternatively spliced gene product. The splicing event results in a frame shift with the consequence of addition of two glutamate residues after glycine at position 137 before translational termination. The final product lacks the entire transmembrane and cytoplasmic regions and importantly is lacking the cysteine residue, at position 141, that mediates the disulfide linkage of dimeric CD28 (Magistrelli G., Biochem Biophy Res Commun, 1999). The biological function and counter-receptor binding of the monomeric CD28 soluble form was examined (Hebbar, M., Clin Exp Immunol, 2004) and was shown to also inhibit T cell proliferation. Still, in the case of dimeric sCD28 it has been suggested to have a regulatory role to suppress T cell functionality by binding to B7 molecules (Sun, Z., Centr Eur J Immunol, 2014; Hebbar, M., Clin Exp Immunol, 2004). Remarkably, an elevation in the number of sCD28 molecules in the serum of patients with auto-immune disorders has been reported (Wong, C. K., Rheumatol, 2005; Hamzaoui, K., Clin Exp Rheumatol, 2005; Hebbar, M., Clin Exp Immunol, 2004; Sun, Z., Clin Immunol, 2014). The definite source of sCD28 is debated. Using in-vitro models of T cell activation, reflecting the durable inflammation state of T cells in auto-immune patients, it has been shown that during the process of T cell activation the transcription of the alternative soluble form is repressed and only full-length membrane form of CD28 is evident, while the amount of the sCD28 in the culture is elevated (Hebbar, M., Clin Exp Immunol, 2004). This phenomenon led to the proposition that active shedding of the membrane form of CD28 is the cause for elevated soluble molecules in the serum, however, this has yet to be proven. Active shedding during T cell activation was described in the past as a regulatory mechanism to counteract persistent activation by the proteolysis of adhesion molecules.

While CTLA-4 limits the amplitude of early T cell responses, another inhibitory receptor, PD-1, suppresses T cell function in periphery. The expression of PD-1 is elevated during the activation of T cells, and its known ligands are the B7 family homologs: B7-H1 (PD-L1) and B7-H2 (PD-L2). These homologs are found on APCs and cancer cells and drive activated T cells into a state of cellular anergy, leading to a dampened immune response. Accordingly, targeted therapies for the CTLA-4 and PD-1/PD-L1 axis have shown clinical activity in a wide variety of cancer types. Recently, studies have shown that the signaling pathway of CD28 is targeted and repressed by PD-1 (Hui, E., Science, 2017) and concomitantly for an effective PD-1 therapy to take place an intact active CD28/B7 axis is essential (Kamphorst, A. O., Science, 2017).

However, not all patients respond to PD-1 based immunotherapy or immunotherapy in general, and those that do often relapse. Methods and molecules that can improve the ability of a patient's immune cells to attack cancer are thus greatly in need.

SUMMARY OF THE INVENTION

The present invention provides Methods of treating cancer and improving PD-1/PD-L1 based immunotherapy comprising decreasing soluble CD28 levels. Agents that bind membranal CD28 and inhibit proteolytic cleavage of mCD28 and agents that bind soluble CD28 and that are neither CD28 agonists nor antagonists are also provided, as are methods of producing these agents.

According to a first aspect, there is provided a method of treating and/or preventing cancer in a subject in need thereof, the method comprising decreasing soluble CD28 (sCD28) levels in the subject.

According to another aspect, there is provided a method of improving PD-1 and/or PD-L1 based immunotherapy in a subject in need thereof, the method comprising decreasing sCD28 levels in the subject.

According to another aspect, there is provided an agent that binds soluble CD28 (sCD28) and is neither a CD28 agonist nor antagonist.

According to some embodiments, the subject in need of immunotherapy suffers from cancer. According to some embodiments, the subject does not respond or lowly responds to PD-1 and/or PD-L1 based immunotherapy.

According to some embodiments, the decreasing occurs in the blood, peripheral blood, or tumor microenvironment of the subject. According to some embodiments, the decreasing comprises at least one of:
  a. administering to the subject an agent that binds to sCD28 and wherein the agent, upon binding, degrades the sCD28 or targets the sCD28 for degradation;
  b. administering to the subject an inhibitory nucleic acid molecule, wherein the molecule binds to an mRNA coding for sCD28 and does not bind to an mRNA coding for membranal CD28 (mCD28);
  c. administering to the subject an agent that binds mCD28 and inhibits proteolytic cleavage of the mCD28;
  d. administering to the subject a dimeric peptide comprising a stalk region of human CD28;
  e. administering to the subject an agent that inhibits a protease capable of cleaving mCD28 and
  f. withdrawing blood from the subject, decreasing the amount of sCD28 in the blood and returning the blood to the subject.

According to some embodiments, the stalk region,
  a. comprises the amino acid sequence GKHLCPSPLFPGPSKP (SEQ ID NO: 9) or KGKHLCPSPLFPGPS (SEQ ID NO: 36);
  b. consists of the amino acid sequence HVKGKHLCPSPLFPGPSKP (SEQ ID NO: 10); or
  c. both (a) and (b).

According to some embodiments, the method does not degrade mCD28 or decrease mCD28-mediated immune cell activation.

According to some embodiments, the subject's blood prior to the decreasing comprises at least 5 ng/ml sCD28.

According to some embodiments, the cancer is selected from melanoma, head and neck, non-small cell lung cancer, ovarian, kidney, gastric and colorectal. According to some embodiments, the cancer is selected from melanoma, head and neck, non-small cell lung cancer, ovarian, and colorectal.

According to some embodiments, the method of the invention further comprises administering another immunotherapy to the subject. According to some embodiments, the immunotherapy is selected from:
  a. a checkpoint inhibitor;
  b. a chimeric antigen receptor (CAR) based therapy; and
  c. a cancer vaccine.

According to some embodiments, the checkpoint inhibitor is a PD-1 and/or PD-L1 based immunotherapy.

According to another aspect, there is provided an agent that binds membranal CD28 (mCD28) and inhibits proteolytic cleavage of the mCD28.

According to some embodiments, the agent is neither a CD28 agonist or antagonist. According to some embodiments, the agent neither degrades the mCD28 nor inhibits mCD28-mediated immune cell activation.

According to some embodiments, the agent
  a. does not induce antibody-dependent cell-mediated cytotoxicity (ADCC) or complement-dependent cytotoxicity (CDC);
  b. comprises IgG2 or IgG4;
  c. comprises an Fc domain engineered to decrease CDC, ADCC or both;
  d. lacks an Fc domain;
  e. is a Fab fragment;
  f. is a single chain antibody;
  g. is a single-domain antibody;
  h. is a small molecule;
  i. is a peptide with specific binding to mCD28; or
  j. a combination thereof.

According to some embodiments, the agent binds within the stalk region of CD28. According to some embodiments, the stalk region
  a. comprises the amino acid sequence GKHLCPSPLFPGPSKP (SEQ ID NO: 9) or KGKHLCPSPLFPGPS (SEQ ID NO: 36);
  b. consists of the amino acid sequence HVKGKHLCPSPLFPGPSKP (SEQ ID NO: 10); or
  c. both (a) and (b).

According to some embodiments, the agent inhibits proteolytic cleavage by at least one protease. According to some embodiments, the at least one protease is at least one metalloprotease. According to some embodiments, the at least one metalloprotease is selected from ADAM10 and ADAM17.

According to some embodiments, the agent is an antibody or antigen binding fragment thereof and comprises three heavy chain CDRs (CDR-H) and three light chain CDRs (CDR-L), wherein:
  CDR-H1 comprises the amino acid sequence set forth in SEQ ID NO: 30 (GFTFSSYYMS), CDR-H2 comprises the amino acid sequence as set forth in SEQ ID NO: 31 (TISDGGDNTYYAGTVTG), CDR-H3 comprises the amino acid sequence as set forth in SEQ ID NO: 32 (IHWPYYFDS), CDR-L1 comprises the amino acid sequence as set forth in SEQ ID NO: 33 (RASSSVSYMN), CDR-L2 comprises the amino acid sequence as set forth in SEQ ID NO: 34 (ATSDLAS), and CDR-L3 comprises the amino acid sequence as set forth in SEQ ID NO: 35 (QQWSSHPPT).

According to some embodiments, the agent of the invention comprises at least one of
  a. a heavy chain comprising the amino acid sequence of SEQ ID NO: 53; and
  b. a light chain comprising the amino acid sequence of SEQ ID NO: 55.

According to some embodiments, the agent does not bind membranal CD28 (mCD28).

According to some embodiments, the agent is selected from an antibody or antigen binding fragment thereof, a Fab fragment, a single chain antibody, a single domain antibody, a small molecule, and a peptide with specific binding to sCD28.

According to some embodiments, binding of the agent to sCD28 in an organism results in at least one of:
  a. degradation of the bound sCD28;
  b. removal of sCD28 from blood; and
  c. transport of the bound sCD28 to a lysosome, endosome, proteasome or a combination thereof.

According to some embodiments, the agent does not inhibit binding of the sCD28 to a ligand. According to some embodiments, the agent binds dimeric sCD28, monomeric sCD28 or both. According to some embodiments, the agent binds outside the IgV domain of sCD28.

According to some embodiments, the agent is an antibody or antigen binding fragment thereof and comprises three heavy chain CDRs (CDR-H) and three light chain CDRs (CDR-L), wherein:

CDR-H1 comprises the amino acid sequence set forth in SEQ ID NO: 12 (GYTLTNY), CDR-H2 comprises the amino acid sequence as set forth in SEQ ID NO: 13 (NTYTGK), CDR-H3 comprises the amino acid sequence as set forth in SEQ ID NO: 14 (GDANQQFAY), CDR-L1 comprises the amino acid sequence as set forth in SEQ ID NO: 15 (KASQDINSYLS), CDR-L2 comprises the amino acid sequence as set forth in SEQ ID NO: 16 (RANRLVD), and CDR-L3 comprises the amino acid sequence as set forth in SEQ ID NO: 17 (LQYDEFPPT);

CDR-H1 comprises the amino acid sequence set forth in SEQ ID NO: 18 (GYTFTSY), CDR-H2 comprises the amino acid sequence as set forth in SEQ ID NO: 19 (YPGDGD), CDR-H3 comprises the amino acid sequence as set forth in SEQ ID NO: 20 (NYRYSSFGY), CDR-L1 comprises the amino acid sequence as set forth in SEQ ID NO: 21 (KSSQSLLNSGNQKNYLT), CDR-L2 comprises the amino acid sequence as set forth in SEQ ID NO: 22 (WASTRES), and CDR-L3 comprises the amino acid sequence as set forth in SEQ ID NO: 23 (QSDYSYPLT); or CDR-H1 comprises the amino acid sequence set forth in SEQ ID NO: 24 (GYTFTDY), CDR-H2 comprises the amino acid sequence as set forth in SEQ ID NO: 25 (NPNYDS), CDR-H3 comprises the amino acid sequence as set forth in SEQ ID NO: 26 (SSPYYDSNHFDY), CDR-L1 comprises the amino acid sequence as set forth in SEQ ID NO: 27 (SARSSINYMH), CDR-L2 comprises the amino acid sequence as set forth in SEQ ID NO: 28 (DTSKLAS), and CDR-L3 comprises the amino acid sequence as set forth in SEQ ID NO: 29 (HQRNSYPFT).

According to some embodiments, the agent of the invention comprises at least one of
a. a heavy chain comprising an amino acid sequence selected from SEQ ID NO: 41, 45 or 49; and
b. a light chain comprising an amino acid sequence selected from SEQ ID NO: 43, 47 or 51.

According to some embodiments, the antigen binding fragment is selected from the group consisting of a Fv, Fab, F(ab')2, scFV or a scFV2 fragment.

According to some embodiments, the agent is humanized.

According to some embodiments, the agent does not induce antibody-dependent cell-mediated cytotoxicity (ADCC) or complement-dependent cytotoxicity (CDC).

According to another aspect, there is provided a method for producing an agent of the invention, the method comprising:

obtaining an agent that binds to a CD28 extracellular domain or fragment thereof, testing an ability of the agent to block cleavage of mCD28 by a protease, and selecting at least one agent that blocks cleavage of mCD28 by the protease; or
culturing a host cell comprising one or more vectors comprising a nucleic acid sequence encoding an agent, wherein the nucleic acid sequence is that of an agent that was selected by:
 i. obtaining an agent that binds to a CD28 extracellular domain or fragment thereof,
 ii. testing an ability of the agent to block cleavage of mCD28 by a protease; and
 iii. selecting at least one agent that blocks cleavage of mCD28 by the protease;
thereby producing an agent of the invention.

According to another aspect, there is provided a method for producing an agent of the invention, the method comprising:

obtaining an agent that binds to a CD28 extracellular domain or fragment thereof, assaying mCD28 downstream signaling in the presence of the obtained agent, and selecting at least one agent that neither substantially agonizes nor substantially antagonizes mCD28 signaling; or
culturing a host cell comprising one or more vectors comprising a nucleic acid sequence encoding an agent, wherein the nucleic acid sequence is that of an agent that was selected by:
 i. obtaining an agent that binds to a CD28 extracellular domain or fragment thereof,
 ii. assaying mCD28 downstream signaling in the presence of the obtained agent; and
 iii. selecting at least one agent that neither substantially agonizes nor substantially antagonizes mCD28 signaling;
thereby producing an agent of the invention.

According to some embodiments, the protease is selected from, ADAM10 and ADAM17.

According to some embodiments, obtaining an agent that binds specifically to CD28 extracellular domain or a fragment thereof is obtaining an agent that binds specifically to a CD28 stalk domain.

According to some embodiments, the method of the invention further comprises assaying mCD28 downstream signaling in the presence of the obtained agent and selecting at least one agent that neither substantially agonizes nor substantially antagonizes mCD28 signaling.

According to some embodiments, the method of the invention further comprises at least one of:
a. testing binding of the obtained agent to mCD28 and selecting at least one agent that does not bind mCD28; and
b. testing binding of the obtained agent to sCD28 from a cancer patient and selecting at least one agent that binds the sCD28 from a cancer patient.

According to some embodiments, the obtaining the agent comprises at least one of:
a. immunizing an organism with the CD28 extracellular domain or fragment thereof and collecting antibodies from the immunized organism;
b. screening a library of agents for binding to a CD28 extracellular domain or fragment thereof and selecting an agent that binds.

According to some embodiments, the CD28 extracellular domain or fragment thereof is dimeric or monomeric According to some embodiments, the organism is selected from a rabbit, a mouse, a rat, a shark, a camelid, a chicken, a goat and a phage.

According to some embodiments, the collecting antibodies comprises:
a. extracting B cells from a spleen of the immunized organism;
b. fusing the extracted B cells with myeloma cells to produce a hybridoma; and
c. collecting antibodies from the hybridoma.

According to some embodiments, the selecting an agent that binds comprises sequencing the selected agent and producing a recombinant form of the agent from the sequence.

According to another aspect, there is provided an agent produced by the method of the invention.

According to another aspect, there is provide a pharmaceutical composition comprising an agent of the invention, and a pharmaceutically acceptable carrier, excipient or adjuvant.

According to another aspect, there is provided a method of treating and/or preventing cancer or improving PD-1 and/or PD-L1 based immunotherapy in a subject in need thereof, the method comprising administering to the subject a pharmaceutical composition of the invention.

According to another aspect, there is provided a method of determining suitability of a subject to be treated by a method of the invention, comprising obtaining a sample from the subject and determining sCD28 levels in the sample, wherein a sCD28 level above 5 ng/ml indicates the subject is suitable for a method of treatment of the invention.

According to another aspect, there is provided a kit comprising at least one agent of the invention.

According to some embodiments, the kit of the invention further comprises at least one of:
 a. an anti-PD-1 and/or PD-L1 immunotherapy;
 b. a label stating the agent of the invention is for use with a PD-1 and/or PD-L1 based immunotherapy; and
 c. a secondary detection molecule for detecting the at least one agent of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
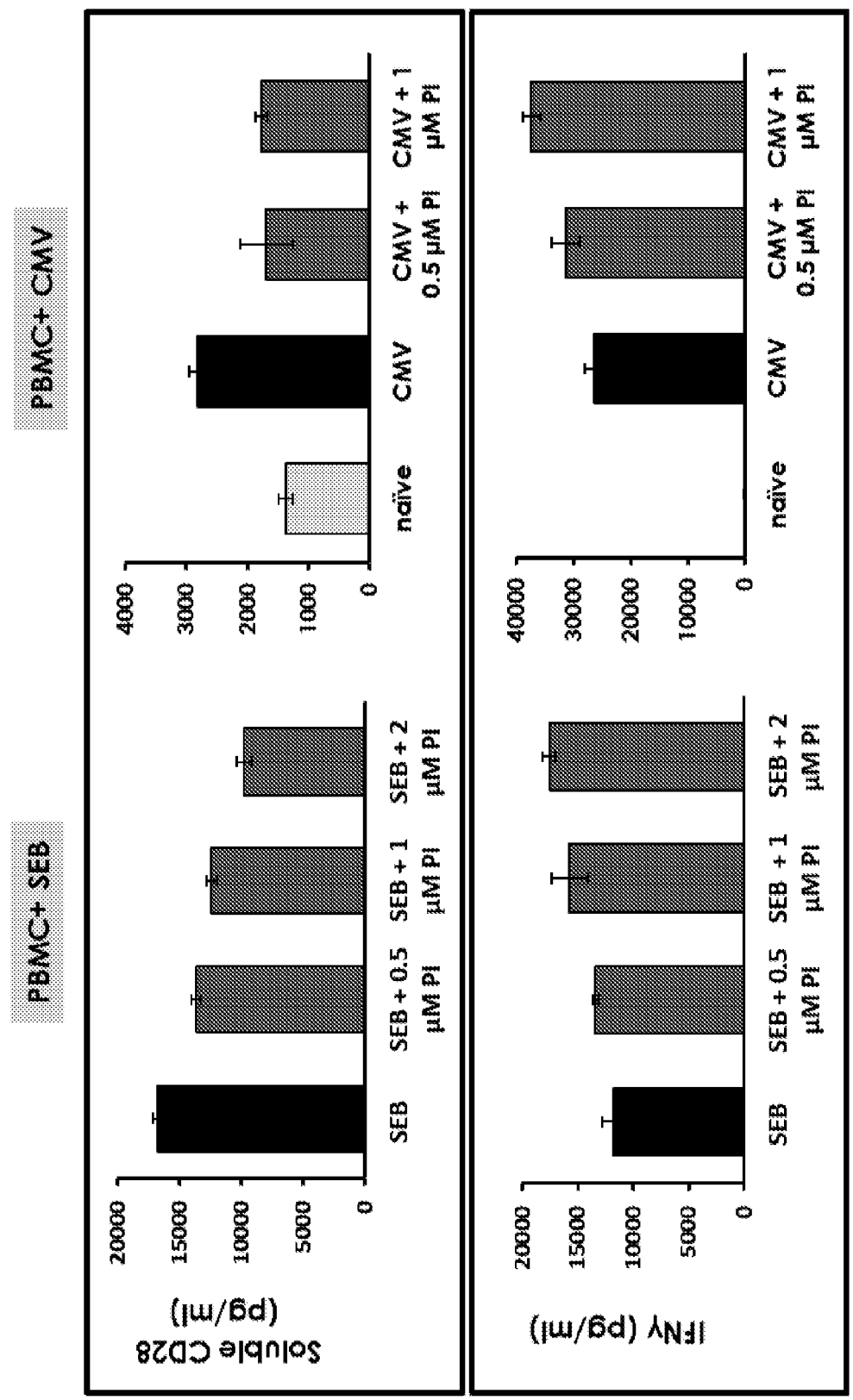
FIG. 1. Soluble CD28 is generated during stimulation of PBMCs and counteracted by addition of protease inhibitors (PI). Bar charts of the amount of soluble CD28 in the culture of PBMCs stimulated with SEB (0.5 ng/mL, left side) or CMV peptides (0.5 µg/mL, right side) as quantified by human CD28 ELISA (top panel). A cocktail of protease inhibitors was added at the indicated concentrations. The overall health and effector activity were examined by the secretion of interferon gamma (low panel).

The present invention, in some embodiments, provides agents that bind membranal CD28 (mCD28) and inhibit proteolytic cleavage of mCD28 and agents that bind soluble CD28 (sCD28) and which are neither CD28 agonists nor antagonists. The present invention further provides agents that upon binding degrade or lead to the degradation of sCD28, or lead to its clearance from the circulation, tissues, and/or tumor microenvironments (TMEs). In some cases, the agents can perform more than one of these tasks. Methods of treating cancer and improving PD-1/PD-L1 based immunotherapy comprising decreasing soluble CD28 (sCD28) levels are also provided. The agents and methods of the invention are based on the surprising finding that a large number of cancer patients have elevated sCD28 levels in their blood stream. sCD28 is a known immune modulator that is sometimes over expressed in autoimmune disease. However, until now highly elevated levels have never been reported in a wide variety of cancers. Further, it was unexpectedly found that sCD28 could inhibit PD-1/PD-L1 based immunotherapy. Thus, a reduction in sCD28 in a subject's blood stream, leads to a reduction in the deleterious effects of sCD28 on a subject's ability to fight cancer and the effectiveness of immunotherapy.

The anti-cleavage molecules of the invention have a double benefit. By blocking proteolytic cleavage of mCD28 they keep the amount of CD28 high on the cell surface of T cells. This allows for rapid and effective T cell activation, that would be impaired if the levels of surface CD28 dropped due to cleavage. Further, the reduction in cleavage leads to a reduction in sCD28 in a subject's blood stream, and thus a reduction in the deleterious effects of sCD28 on a subject ability to fight cancer and the effectiveness of immunotherapy.

Binding sCD28

By a first aspect, there is provided an agent that binds soluble CD28 (sCD28) and is neither a CD28 agonist or antagonist.

In some embodiments, the CD28 is mammalian CD28. In some embodiments the CD28 is human CD28. In some embodiments, the human CD28 comprises or consists of the amino acid sequence:
MLRLLLALNLFPSIQVTGNKILVKQSPMLVAYD-
NAVNLSCKYSYNLFSREFRASLHKG LDSAVEVCV-
VYGNYSQQLQVYSKTGFNCDGKLGNESVTFYLQN-
LYVNQTDIYFCKIE
VMYPPPYLD-
NEKSNGTIIHVKGKHLCPSPLFPGPSKPFWVLVVVG
GVLACYSLLVTVA FIIFWVRSKRSRLLHSDYMNMT-
PRRPGPTRKHYQPYAPPRDFAAYRS (SEQ ID NO: 1).
In some embodiments, mature CD28 lacks a signal peptide and comprises the sequence: NKILVKQSPMLVAYD-
NAVNLSCKYSYNLFSREFRASLHKGLDSAVEVCV-
VYGNYSQQ LQVYSKTGFNCDGKLGNESVTFYLQN-
LYVNQTDIYFCKIEVMYPPPYLDNEKSNGTIIH
VKGKHLCPSPLFPGPSKPFWVLVVVGGVLACYSLL-
VTVAFIIFWVRSKRSRLLHSDYM NMTPRRPGP-
TRKHYQPYAPPRDFAAYRS (SEQ ID NO: 2).

In some embodiments, the DNA coding sequence that codes for full length human CD28 comprises the sequence:
ATGCTCAGGCTGCTCTTGGCTCTCAACTTAT-
TCCCTTCAATTCAAGTAACAGGAAAC AAGAT-
TTGGTGAAGCAGTCGCC-
CATGCTTGTAGCGTACGACAATGCGGTCAACCT
TAGCTGCAAGTATTCCTACAATCTCTTCTCAAGG-
GAGTTCCGGGCATCCCTTCACA AAGGACTGGA-
TAGTGCTGTGGAAGTCTGTGTTGTATATGGGAAT-
TACTCCCAGCAG
CTTCAGGTTTACTCAAAAACGGGGTTCAACTGT-
GATGGGAAATTGGGCAATGAATC AGTGACATTC-
TACCTCCAGAATTTGTATGTTAACCAAACAGATATT-
TACTTCTGCAA
AATTGAAGTTATGTATCCTCCTCCTTACCTA-
GACAATGAGAAGAGCAATGGAACCA TTATCCATGT-
GAAAGGGAAACACCTTTGTCCAAGTCCCCTAT-
TTCCCGGACCTTCTA
AGCCCTTTTGGGTGCTGGTGGTGGTTGGTG-
GAGTCCTGGCTTGCTATAGCTTGCTAG
TAACAGTGGCCTTTATTATrTTCTGGGTGAG-
GAGTAAGAGGAGCAGGCTCCTGCAC AGTGACTA-
CATGAACATGACTCCCCGCCGCCCCGGGCC-
CACCCGCAAGCATTACCA
GCCCTATGCCCCACCACGCGACTTCGCAGCC-
TATCGCTCCTGA (SEQ ID NO: 3).

As used herein, sCD28 refers to any CD28 fragment or variant that does not comprise a transmembrane domain and thus cannot be integrated in a membrane. In some embodiments, the CD28 transmembrane domain comprises the amino acid sequence FWVLVVVGGVLACYSLL-
VTVAFIIFWV (SEQ ID NO: 4). In some embodiments, sCD28 is not membrane bound. In some embodiments, sCD28 is in solution. In some embodiments, the sCD28 is CD28 in blood. In some embodiments, the sCD28 is CD28 in the TME. In some embodiments, sCD28 is CD28 in a bodily fluid. In some embodiments, sCD28 lacks exon 3 of CD28. In some embodiments, sCD28 is a splice variant arising from alternative splicing that splices out exon 3 of CD28. In some embodiments, sCD28 is a cleavage product from membranal CD28 (mCD28). In some embodiments, sCD28 is truncated CD28. In some embodiments, sCD28 lacks the cytoplasmic domain of full-length CD28. In some embodiments, sCD28 is dimeric sCD28. In some embodiments, sCD28 is monomeric sCD28. In some embodiments, sCD28 is not a splice variant arising from alternative splicing of CD28. In some embodiments, the alternative splicing splices out exon 3 of CD28. In some embodiments, sCD28 comprises the amino acid sequence: MLRLLLALNLFP-
SIQVTGNKILVKQSPMLVAYDNAVNLSCKYSYNLFS-
REFRASLHKG LDSAVEVCVVYG-
NYSQQLQVYSKTGFNCDGKLGNESVTFYLQNLYVN
QTDIYFCKIE VMYPPPYLDNEKSNGTIIHVKGEE
(SEQ ID NO: 5). In some embodiments, sCD28 lacks the signal peptide and comprises the sequence: NKIL-
VKQSPMLVAYDNAVNLSCKYSYNLFSRE-
FRASLHKGLDSAVEVCVVYGNYSQQ
LQVYSKTGFNCDGKLGNESVTFYLQNLY-
VNQTDIYFCKIEVMYPPPYLDNEKSNGTIIH VKGEE
(SEQ ID NO: 6).

In some embodiments, the DNA coding sequence that codes for human sCD28 comprises the sequence:

(SEQ ID NO: 7)
ATGCTCAGGCTGCTCTTGGCTCTCAACTTATTCCCTTCAATT

CAAGTAACAGGAAACAAGATTTTGGTGAAGCAGTCGCCCATG

CTTGTAGCGTACGACAATGCGGTCAACCTTAGCTGCAAGTAT

TCCTACAATCTCTTCTCAAGGGAGTTCCGGGCATCCCTTCAC

AAAGGACTGGATAGTGCTGTGGAAGTCTGTGTTGTATATGGG

AATTACTCCCAGCAGCTTCAGGTTTACTCAAAAACGGGGTTC

AACTGTGATGGGAAATTGGGCAATGAATCAGTGACATTCTAC

CTCCAGAATTTGTATGTTAACCAAACAGATATTTACTTCTGC

AAAATTGAAGTTATGTATCCTCCTCCTTACCTAGACAATGAG

AAGAGCAATGGAACCATTATCCATGTGAAAGGTGAGGAGTAA

GAGGAGCAGGCTCCTGCACAGTGACTACATGAACATGACTCC

CCGCCGCCCCGGGCCCACCCGCAAGCATTACCAGCCCTATGC

CCCACCACGCGACTTCGCAGCCTATCGCTCCTGA.

In some embodiments, the agent binds sCD28 and mCD28, and leads to or causes the degradation or clearance of only sCD28. In some embodiments, the agent does not bind membranal CD28 (mCD28). As used herein, mCD28 refers to any CD28 which comprises a transmembrane domain and thus can be integrated in a membrane. In some embodiments, the CD28 transmembrane domain comprises the amino acid sequence FWVLVVVGGVLACYSLL-
VTVAFIIFWV (SEQ ID NO: 4). In some embodiments, mCD28 is in a membrane. In some embodiments, mCD28 has passed from the ER, and through the Golgi into the plasma membrane of a cell. In some embodiments, mCD28 is in the plasma membrane of an immune cell. In some embodiments, mCD28 is in the plasma membrane of a T cell.

In some embodiments, the agent is not a CD28 agonist. In some embodiments, the agent is not a CD28 antagonist. In some embodiments, the agent is neither a CD28 agonist or antagonist. In some embodiments, the sCD28 binding agent is also an mCD28 agonist.

The term "agonist" generally refers to a molecule, compound or agent that binds to a receptor and activates, fully or partially, the receptor. In some embodiments, the agonist binds at the same site as the natural ligand. In some embodiments, the agonist binds at an allosteric site different from the binding site of the natural ligand. The term "antagonist" generally refers to a molecule, compound or agent that binds to a receptor at the same site as an agonist or another site, does not activate the receptor and does one or more of the following: interferes with or blocks activation of the receptor by a natural ligand, and interferes with or blocks activation of the receptor by a receptor agonist. In some embodiments, the antibodies of the invention bind to mCD28 but do not activate or block activation of the receptor. In some embodiments, they do not block activation by CD86. In some embodiments, the antibodies of the invention do not bind mCD28.

As used herein, a "direct agonist/antagonist" refers to a molecule that binds to a receptor (mCD28) and by binding increases/decreases signaling by that molecule. In the case of mCD28 an agonist would bind mCD28 and by binding increase mCD28 signaling in the cell. In some embodiments, the agonist increases T cell activation. In some embodiments, the agonist increases T cell proliferation. In some embodiments, the agonist increases pro-inflammatory cytokine secretion. Pro-inflammatory cytokines are well known in the art and are known to be secreted by activated T cells. Examples of pro-inflammatory cytokines include, but are not limited to, TNFα, IFNγ, IL-1B, and IL-6. In some embodiments, the pro-inflammatory cytokine is IFNγ. In the case of mCD28 an antagonist would bind mCD28 and by binding decrease mCD28 signaling in the cell. In some embodiments, the antagonist decreases T cell activation, decreases T cell proliferation and/or decreases pro-inflammatory cytokine secretion. A molecule that effects a receptor's signaling by contacting its ligand, contacting an inhibitor, contacting a co-receptor or contacting any molecule other than the receptor in question in order to modify receptor signaling is not considered a direct agonist/antagonist. In some embodiments, the agent of the invention contacts sCD28 in serum and thereby allows for increased signaling through mCD28 on cells. Though the result is increased mCD28 signaling the antibody is not a mCD28 agonist or direct agonist as its binding to mCD28 does not increase the receptors signaling.

In some embodiments, the agent does not bind the ligand binding domain of mCD28. In some embodiments, the agent does not obscure or block access to the ligand binding domain. In some embodiments, the agent does not bind, obscure or block access to the IgV domain of sCD28. In some embodiments, the IgV domain is the ligand binding domain. In some embodiments, the ligand binding domain comprises amino acids 28-137 of SEQ ID NO: 1. In some embodiments, the ligand binding domain comprises or consists of the amino acid sequence MLVAYD-NAVNLSCKYSYNLFSREFRASLHKGLDSAVEVCV-VYGNYSQQLQVYSKTG FNCDGKLGNESVTFYLQNLYVNQTDIYFCKI-EVMYPPPYLDNEKSNGTIIHVKG (SEQ ID NO: 8). In some embodiments, the agent does not inhibit binding of sCD28 to a ligand. In some embodiments, the CD28 ligand is selected from: CD80, CD86 and ICOSL. In some embodiments, the CD28 ligand is CD86. In some embodiments, the CD28 ligand is CD80. In some embodiments, the CD28 ligand is ICOSL. In some embodiments, CD86 is CD86-Fc. In some embodiments, CD80 is CD80-Fc.

In some embodiments, the agent binds a stalk region of CD28. In some embodiments, the agent binds a membrane proximal region of mCD28. In some embodiments, the stalk region comprises the sequence GKHLCPSPLFPGPSKP (SEQ ID NO: 9). In some embodiments, the stalk region comprises the sequence KGKHLCPSPLFPGPS (SEQ ID NO: 36). In some embodiments, the stalk region comprises or consists of the sequence HVKGKHLCPSPLFPGPSKP (SEQ ID NO: 10). In some embodiments, the agent binds monomeric sCD28. In some embodiments, the agent binds dimeric sCD28. In some embodiments, the agent binds monomeric sCD28, dimeric sCD28 or both. In some embodiments, the agent binds monomeric but not dimeric CD28. As functional mCD28 is dimeric, binding only CD28 monomer may be employed to ensure the agent does not bind mCD28.

An example of an agent includes, but is not limited to, an antibody, an antigen binding fragment of an antibody, a nanobody, a single chain antibody, a single domain antibody, a small molecule, a peptide and a DARPin. In some embodiments, the agent is selected from an antibody, an antigen binding fragment of an antibody, a Fab fragment, a nanobody, a single chain antibody, a single domain antibody, a small molecule, a peptide and a DARPin. In some embodiments, the agent is selected from an antibody, an antigen binding fragment of an antibody, a Fab fragment, a single chain antibody, a single domain antibody, a small molecule, and a peptide with specific binding to CD28. In some embodiments, the agent is a single domain antibody. In some embodiments, the agent is a nanobody. In some embodiments, the agent is a VHH antibody. As used herein, the terms "single domain antibody", "nanobody" and "VHH antibody" are synonymous and used interchangeably. In some embodiments, the peptide has specific binding to CD28. In some embodiments, the agent is a peptide with specific binding to CD28. In some embodiments, the peptide is selected from an antibody, an antigen binding fragment of an antibody, a Fab fragment, a single chain antibody, a single-domain antibody, a nanobody, a VHH antibody and an antibody mimetic. As used herein, the term "antibody mimetic" refers to an organic compound that can specifically bind to a target antigen. In some embodiments, an antibody mimetic is not structurally related to an antibody. Examples of antibody mimetics include, but are not limited to, affilins, affimers, affitins, alphabodies, anticalins, avimers, DARPins, fynomers, Kunitz domain peptides, monobodies, and nanoCLAMPS. In some embodiments, the antibody mimetic is a DARPin. All of these agents are well known in the art and are known to be useful in blocking interactions between receptors and their ligands. Small molecules and proteins that can bind mCD28 may occlude the cleavage site or may cause hinderance or impair access for the protease. In some embodiments, the protein is an antibody mimetic. As used herein, the term "DARPin" refers to a designed ankyrin repeat protein. DARPins are genetically engineered antibody mimetic proteins that are generally highly specific for their protein target. Thus, a DARPin for CD28 may be an example of an agent.

In some embodiments, the agent that binds sCD28 is an antibody or antigen binding fragment thereof. In some embodiments, the antibody to sCD28 is a single domain antibody. In some embodiments, the antibody to sCD28 lacks an Fc domain. In some embodiments, the agent that binds sCD28 is an antigen binding domain that lacks an Fc domain. In some embodiments, the agent that binds sCD28 is a single-domain antibody. In some embodiments, the agent that binds sCD28 is a camelid, shark or nanobody. In some embodiments, the antibody or fragment is fused to another protein or fragment of a protein. In some embodiments, the second protein or fragment increases half-life, particularly in serum. In some embodiments, the half-life extending protein is human serum albumin. In some embodiments, the agent is modified by a chemical that produces a modification that enhances half-life. In some embodiments, the modification is PEGylation and the chemical is polyethylene glycol. A skilled artisan will appreciate that any half-life extending protein or chemical agent, or modification known in the art may be used.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', F(ab')2 single stranded antibody (svFC), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)~Fc fusions and scFv-scFv-Fc fusions.

Immunoglobulin molecules can be of any type (e.g., IgG, IgE, IgM, IgD, IgA and IgY), class (e.g., IgG1, IgG2, IgG3, IgG4, IgA1 and IgA2) or subclass. In some embodiments, the antibody comprises IgG2 or IgG4. In some embodiments, the antibody comprises IgG2. In some embodiments, the antibody comprises IgG4.

The basic unit of the naturally occurring antibody structure is a heterotetrameric glycoprotein complex of about 150,000 Daltons, composed of two identical light (L) chains and two identical heavy (H) chains, linked together by both noncovalent associations and by disulfide bonds. Each heavy and light chain also has regularly spaced intra-chain disulfide bridges. Five human antibody classes (IgG, IgA, IgM, IgD and IgE) exist, and within these classes, various subclasses, are recognized based on structural differences, such as the number of immunoglobulin units in a single antibody molecule, the disulfide bridge structure of the individual units, and differences in chain length and sequence. The class and subclass of an antibody is its isotype.

The amino terminal regions of the heavy and light chains are more diverse in sequence than the carboxy terminal regions, and hence are termed the variable domains. This part of the antibody structure confers the antigen-binding specificity of the antibody. A heavy variable (VH) domain and a light variable (VL) domain together form a single antigen-binding site, thus, the basic immunoglobulin unit has two antigen-binding sites. Particular amino acid residues are believed to form an interface between the light and heavy chain variable domains (Chothia et al., J. Mol. Biol. 186, 651-63 (1985); Novotny and Haber, (1985) Proc. Natl. Acad. Sci. USA 82 4592-4596).

The carboxy terminal portion of the heavy and light chains form the constant domains i.e. CH1, CH2, CH3, CL. While there is much less diversity in these domains, there are differences from one animal species to another, and further, within the same individual there are several different isotypes of antibody, each having a different function.

The term "framework region" or "FR" refers to the amino acid residues in the variable domain of an antibody, which are other than the hypervariable region amino acid residues as herein defined. The term "hypervariable region" as used herein refers to the amino acid residues in the variable domain of an antibody, which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Kabat et al.).

Immunoglobulin variable domains can also be analyzed using the IMGT information system (www://imgt.cines.fr/) (IMGT@/V-Quest) to identify variable region segments, including CDRs. See, e.g., Brochet, X. et al, Nucl. Acids Res. J6:W503-508 (2008).

Chothia et al. also defined a numbering system for variable domain sequences that is applicable to any antibody. One of ordinary skill in the art can unambiguously assign this system of "Chothia numbering" to any variable domain sequence, without reliance on any experimental data beyond the sequence itself. As used herein, "Chothia numbering" refers to the numbering system set forth by Chothia et al., Journal of Molecular Biology, "Canonical Structures for the Hypervariable regions of immunoglobulins" (1987) and Chothia et al., Nature, "Conformations of Immunoglobulin Hypervariable Regions" (1989).

As used herein, the term "humanized antibody" refers to an antibody from a non-human species whose protein sequences have been modified to increase similarity to human antibodies. A humanized antibody may be produced by production of recombinant DNA coding for the CDRs of the non-human antibody surrounded by sequences that resemble a human antibody. In some embodiments, the humanized antibody is a chimeric antibody. In some embodiments, humanizing comprises insertion of the CDRs of the invention into a human antibody scaffold or backbone. Humanized antibodies are well known in the art and any method of producing them that retains the CDRs of the invention may be employed.

The term "monoclonal antibody" or "mAb" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies and is not to be construed as produced by any specific preparation method. Monoclonal antibodies to be used in accordance with the methods provided herein, may be made by the hybridoma method first described by Kohler et al, Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624-628 (1991) and Marks et al, J. Mol. Biol. 222:581-597 (1991), for example.

The mAb of the present invention may be of any immunoglobulin class including IgG, IgM, IgD, IgE or IgA. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

"Antibody fragments" comprise a portion of an intact antibody, preferably comprising the antigen binding region thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al, Protein Eng. 8(10): 1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three surfaces of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called a, delta, e, gamma, and micro, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies production is known in the art and is described in Natl. Acad. Sci. USA, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain (VH) and a light chain variable domain (VL), where the VHVL unit has polyepitopic specificity, antibodies having two or more VL and VH domains with each VHVL unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s).

The monoclonal antibodies of the invention may be prepared using methods well known in the art. Examples include various techniques, such as those in Kohler, G. and Milstein, C, Nature 256: 495-497 (1975); Kozbor et al, Immunology Today 4: 72 (1983); Cole et al, pg. 77-96 in MONOCLONAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies, one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

In some embodiments, antibodies and portions thereof include: antibodies, fragments of antibodies, Fab and F(ab')2, single-domain antigen-binding recombinant fragments and natural nanobodies. In some embodiments, the antigen binding fragment is selected from the group consisting of a Fv, Fab, F(ab')2, scFV or a scFV$_2$ fragment.

In some embodiments, the present invention provides nucleic acid sequences encoding the antibodies or antigen binding portions of the present invention.

For example, the polynucleotide may encode an entire immunoglobulin molecule chain, such as a light chain or a heavy chain. A complete heavy chain includes not only a heavy chain variable region (VH) but also a heavy chain constant region (CH), which typically will comprise three constant domains: CH, CH2 and CH3; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and CHI and CK or CL domain has been excised. As minibodies are smaller than conventional antibodies they should achieve better tissue penetration in clinical/diagnostic use but being bivalent they should retain higher binding affinity than monovalent antibody fragments, such as dAbs. Accordingly, unless the context dictates otherwise, the term "antibody" as used herein encompasses not only whole antibody molecules, but also antigen-binding antibody fragments of the type discussed above. Each framework region present in the encoded polypeptide may comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

Suitably, the polynucleotides described herein may be isolated and/or purified. In some embodiments, the polynucleotides are isolated polynucleotides.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring".

In some embodiments, the agent is an antibody or antigen-binding portion thereof, comprising three heavy chain CDRs (CDR-H) and three light chain CDRs (CDR-L), wherein: CDR-H1 comprises the amino acid sequence set forth in SEQ ID NO: 12 (GYTLTNY), CDR-H2 comprises the amino acid sequence as set forth in SEQ ID NO: 13 (NTYTGK), CDR-H3 comprises the amino acid sequence as set forth in SEQ ID NO: 14 (GDANQQFAY), CDR-L1 comprises the amino acid sequence as set forth in SEQ ID NO: 15 (KASQDINSYLS), CDR-L2 comprises the amino acid sequence as set forth in SEQ ID NO: 16 (RANRLVD), and CDR-L3 comprises the amino acid sequence as set forth in SEQ ID NO: 17 (LQYDEFPPT).

In some embodiments, the agent is an antibody or an antigen-binding portion thereof, comprising three heavy chain CDRs (CDR-H) and there light chain CDRs (CDR-L), wherein: CDR-H1 comprises the amino acid sequence set forth in SEQ ID NO: 18 (GYTFTSY), CDR-H2 comprises the amino acid sequence as set forth in SEQ ID NO: 19 (YPGDGD), CDR-H3 comprises the amino acid sequence as set forth in SEQ ID NO: 20 (NYRYSSFGY), CDR-L1 comprises the amino acid sequence as set forth in SEQ ID NO: 21 (KSSQSLLNSGNQKNYLT), CDR-L2 comprises the amino acid sequence as set forth in SEQ ID NO: 22 (WASTRES), and CDR-L3 comprises the amino acid sequence as set forth in SEQ ID NO: 23 (QSDYSYPLT).

In some embodiments, the agent is an antibody or an antigen-binding portion thereof, comprising three heavy chain CDRs (CDR-H) and there light chain CDRs (CDR-L), wherein: CDR-H1 comprises the amino acid sequence set forth in SEQ ID NO: 24 (GYTFTDY), CDR-H2 comprises the amino acid sequence as set forth in SEQ ID NO: 25 (NPNYDS), CDR-H3 comprises the amino acid sequence as set forth in SEQ ID NO: 26 (SSPYYDSNHFDY), CDR-L1 comprises the amino acid sequence as set forth in SEQ ID NO: 27 (SARSSINYMH), CDR-L2 comprises the amino acid sequence as set forth in SEQ ID NO: 28 (DTSKLAS), and CDR-L3 comprises the amino acid sequence as set forth in SEQ ID NO: 29 (HQRNSYPFT).

By another aspect, there is provided an antibody or antigen antigen-binding portion thereof, comprising three heavy chain CDRs (CDR-H) and three light chain CDRs (CDR-L), wherein: CDR-H1 comprises the amino acid sequence set forth in SEQ ID NO: 12 (GYTLTNY), CDR-H2 comprises the amino acid sequence as set forth in SEQ ID NO: 13 (NTYTGK), CDR-H3 comprises the amino acid sequence as set forth in SEQ ID NO: 14 (GDANQQFAY), CDR-L1 comprises the amino acid sequence as set forth in SEQ ID NO: 15 (KASQDINSYLS), CDR-L2 comprises the amino acid sequence as set forth in SEQ ID NO: 16 (RANRLVD), and CDR-L3 comprises the amino acid sequence as set forth in SEQ ID NO: 17 (LQYDEFPPT).

By another aspect, there is provided an antibody or an antigen-binding portion thereof, comprising three heavy chain CDRs (CDR-H) and there light chain CDRs (CDR-L), wherein: CDR-H1 comprises the amino acid sequence set forth in SEQ ID NO: 18 (GYTFTSY), CDR-H2 comprises the amino acid sequence as set forth in SEQ ID NO: 19 (YPGDGD), CDR-H3 comprises the amino acid sequence as set forth in SEQ ID NO: 20 (NYRYSSFGY), CDR-L1 comprises the amino acid sequence as set forth in SEQ ID NO: 21 (KSSQSLLNSGNQKNYLT), CDR-L2 comprises the amino acid sequence as set forth in SEQ ID NO: 22 (WASTRES), and CDR-L3 comprises the amino acid sequence as set forth in SEQ ID NO: 23 (QSDYSYPLT).

By another aspect, there is provided an antibody or an antigen-binding portion thereof, comprising three heavy chain CDRs (CDR-H) and there light chain CDRs (CDR-L), wherein: CDR-H1 comprises the amino acid sequence set forth in SEQ ID NO: 24 (GYTFTDY), CDR-H2 comprises the amino acid sequence as set forth in SEQ ID NO: 25 (NPNYDS), CDR-H3 comprises the amino acid sequence as set forth in SEQ ID NO: 26 (SSPYYDSNHFDY), CDR-L1 comprises the amino acid sequence as set forth in SEQ ID NO: 27 (SARSSINYMH), CDR-L2 comprises the amino acid sequence as set forth in SEQ ID NO: 28 (DTSKLAS), and CDR-L3 comprises the amino acid sequence as set forth in SEQ ID NO: 29 (HQRNSYPFT).

In some embodiments, the antibody or antigen-binding fragment thereof comprises a heavy chain comprising the amino acid sequence QIQLVQSGPELKKPGETVKISCKASGYTLTNYGMNWVKQAPGKGLKWMGWINTYTGKPTYVDDFKGRFAFSLETSASTAYLQINNLKNEDTATYFCARGDANQQFAYWGQGTLVTVS (SEQ ID NO: 41). In some embodiments, the variable region of the heavy chain comprises and/or consists of SEQ ID NO: 41. In some embodiments, the antibody or antigen-binding fragment thereof comprises a heavy chain comprising the amino acid sequence QIQLVQSGPELKKPGETVKISCKASGYTLTNYGMNWVKQAPGKGLKWMGWINTYTGKPTYVDDFKGRFAFSLETSASTAYLQINNLKNEDTATYFCARGDANQQFAYWGQGTL VTVSAAKTTPPSVYPLAPGSAAQTNSMVTLGCLVKGYFPEPVTVTWNSGSLSSGVHTF PAVLQSDLYTLSSSVTVPSSTWPSETVTCNVAHPASSTKVDKKI VPRDCGCKPCICTVP EVSSVFIFPPKPKDVLTITLTPKVTCVVVDISKDDPEVQFSWFVDDVEVHTAQTQPREE QFNSTFRSVSELPIMHQDWLNGKEFKCRVNSAAFPAPIEKTISKTKGRPKAPQVYTIPPP KEQMAKDKVSLTCMITDFFPEDITVEWQWNGQPAENYKNTQPIMDTDGSYFVYSKLN VQKSNWEAGNTFTCSVLHEGLHNHHTEKSLSHSPGK (SEQ ID NO: 42). In some embodiments, the heavy chain consists of SEQ ID NO: 42. Antibody #1, as referred to in this application, was sequenced and found to have a heavy chain consisting of SEQ ID NO: 42. The CDRs of this heavy chain, as determined using Chothia scheme, are SEQ ID NOs: 12-14.

In some embodiments, the antibody or antigen-binding fragment thereof comprises a light chain comprising the amino acid sequence DIKMTQSPSSMYASLGERVTITCKASQDINSYLSWFQQKPGKSPKTLIYRANRLVDGVPSRFSGSGSGQDYSLTISSLEYDDMGIYYCLQYDEFPPTFGAGTKLELK (SEQ ID NO: 43). In some embodiments, the variable region of the light chain comprises and/or consists of SEQ ID NO: 43. In some embodiments, the antibody or antigen-binding fragment thereof comprises a light chain comprising the amino acid sequence DIKMTQSPSSMYASLGERVTITCKASQDINSYLSWFQQKPGKSPKTLIYRANRLVDGVPSRFSGSGSGQDYSLTISSLEYDDMGIYYCLQYDEFPPTFGAGTKLELKRADAAPTVSIFP PSSEQLTSGGASVVCFLNNFYPKDINVKWKIDGSERQNGVLNSWTDQDSKDSTYSMSS TLTLTKDEYERHNSYTCEATHKTSTSPIVKSFNRNEC (SEQ ID NO: 44). In some embodiments, the light chain consists of SEQ ID NO: 44. Antibody #1, as referred to in this application, was sequenced and found to have a light chain consisting of SEQ ID NO: 44. The CDRs of this light chain, as determined using Chothia scheme, are SEQ ID NOs: 15-17.

In some embodiments, the antibody or antigen-binding fragment thereof comprises a heavy chain comprising the amino acid sequence QVQLQQSGAELARPGASVKLSCKASGYTFTSYWMQWIKKRPGQGLEWIGAIYPGDGD TRYTQKFKGKATLTADKSSTTAYMQLSSLASEDSAVYFCARNYRYSSFGYWGQGTL V TVSA (SEQ ID NO: 45). In some embodiments, the variable region of the heavy chain comprises and/or consists of SEQ ID NO: 45. In some embodiments, the antibody or antigen-binding fragment thereof comprises a heavy chain comprising the amino acid sequence QVQLQQSGAELARPGASVKLSCKASGYTFTSYWMQWIKKRPGQGLEWIG AIYPGDGD TRYTQKFKGKATLTADKSSTTAYMQLSSLASEDSAVYFCARNYRYSSFGYWGQGTLV TVSAAKTTPPSVYPLAPGCGDTTGSSVTLGCLVKGYFPESVTVTWNSGSLSSSVHTFPA LLQSGLYTMSSSVTVPSSTWPSQTVTCSVAHPASSTTVDKKLEPSGPISTINPCPPCKEC HKCPAPNLEGGPSVFIFPPNIKDVLMISLTPKVTCVVVDVSEDDPDVQISWFVNNVEVH TAQTQTHREDYNSTIRVVSTLPIQHQDWMSGKEFKCKVNNKDLPSPIERTISKIKGLVR APQVYILPPPAEQLSRKDVSLTCLVVGFNPGDISVEWTSNGHTEENYKDTAPVLDSD GS YFIYSKLNMKTSKWEKTDSFSCNVRHEGLKNYYLKKTISRSPGK (SEQ ID NO: 46). In some embodiments, the heavy chain consists of SEQ ID NO: 46. Antibody #2, as referred to in this application, was sequenced and found to have a light chain consisting of SEQ ID NO: 46. The CDRs of this heavy chain, as determined using Chothia scheme, are SEQ ID NOs: 18-20.

In some embodiments, the antibody or antigen-binding fragment thereof comprises a light chain comprising the amino acid sequence DIVMTQSPSSLTVTAGEKVTLSCKSSQSLLNSGNQKNYLTWYQQKPGQPPQLLIYWAS TRESGVPDRFTGSGSGTDFTLTISSVQAEDLAVYYCQSDYSYPLTFGAGTKLELK (SEQ ID NO: 47). In some embodiments, the variable region of the light chain comprises and/or consists of SEQ ID NO: 47. In some embodiments, the antibody or antigen-binding fragment thereof comprises a light chain comprising the amino acid sequence DIVMTQSPSSLTVTAGEKVTLSCKSSQSLLNSGNQKNYLTWYQQKPGQPPQLLIYWAS TRESGVPDRFTGSGSGTDFTLTISSVQAEDLAVYYCQSDYSYPLTFGAGTKLELKRADA APTVSIFPPSSEQLTSGGASVVCFLNNFYPKDINVKWKIDGSERQNGVLNSWTDQDSKD STYSMSSTLTLTKDEYERHNSYTCEATHKTSTSPIVKSFNRNEC (SEQ ID NO: 48). In some embodiments, the light chain consists of SEQ ID NO: 48. In some embodiments, the light chain consists of SEQ ID NO: 48. Antibody #2, as referred to in this application, was sequenced and found to have a light chain consisting of SEQ ID NO: 48. The CDRs of this light chain, as determined using Chothia scheme, are SEQ ID NOs: 21-23.

In some embodiments, the antibody or antigen-binding fragment thereof comprises a heavy chain comprising the amino acid sequence EVQLQQFGAELVKPGASVKISCK-ASGYTFTDYNMDWVKQSHGKSLEWIGDINPNYDS TAYNQKFMGKATLTVDKSSNTAYMELRSLTSED-TAVYYCARSSPYYDSNHFDYWGQ GTSLTVSS (SEQ ID NO: 49). In some embodiments, the variable region of the heavy chain comprises and/or consists of SEQ ID NO: 49. In some embodiments, the antibody or antigen-binding fragment thereof comprises a heavy chain comprising the amino acid sequence EVQLQQFGAELVKPGASVKISCK-ASGYTFTDYNMDWVKQSHGKSLEWIGDINPNYDS TAYNQKFMGKATLTVDKSSNTAYMELRSLTSED-TAVYYCARSSPYYDSNHFDYWGQ GTSLTVS-SAKTTPPSVYPLAPGSAAQTNSMVTLGCLVKGYF-PEPVTVTWNSGSLSSGV HTFPAVLQSDLYTLSSSVTVPSSTWPSETVTCNVAH-PASSTKVDKKIVPRDCGCKPCIC TVPE-VSSVFIFPPKPKDVLTITLTPKVTCVVVDISKDDPE-VQFSWFVDDVEVHTAQTQP REEQFNSTFRSVSELPIMHQDWLNGKEFKCRVN-SAAFPAPIEKTISKTKGRPKAPQVYTI PPPKEQ-MAKDKVSLTCMITDFFPEDITVEWQWNGQPAE-NYKNTQPIMDTDGSYFVYS KLNVQKSNWEAGNTFTCSVL-HEGLHNHHTEKSLSHSPGK (SEQ ID NO: 50). In some embodiments, the heavy chain consists of SEQ ID NO: 50. Antibody #3, as referred to in this application, was sequenced and found to have a heavy chain consisting of SEQ ID NO: 50. The CDRs of this heavy chain, as determined using Chothia scheme, are SEQ ID NOs: 24-26.

In some embodiments, the antibody or antigen-binding fragment thereof comprises a light chain comprising the amino acid sequence QIVLTQSPAIM-SASPGEKVTMTCSARSSINYMHWFQQKPGTSPKR-WIYDTSKLASGVP ARFSGSGSGTSYSLTISNMEAE-DAATYYCHQRNSYPFTFGSGTKLEIK (SEQ ID NO: 51). In some embodiments, the variable region of the light chain comprises and/or consists of SEQ ID NO: 51. In some embodiments, the antibody or antigen-binding fragment thereof comprises a light chain comprising the amino acid sequence QIVLTQSPAIMSASPGEKVTMTCSARSS-INYMHWFQQKPGTSPKRWIYDTSKLASGVP ARFSGSGSGTSYSLTISNMEAEDAATYYCHQRN-SYPFTFGSGTKLEIKRADAAPTVSIFP PSSEQLTSG-GASVVCFLNNFYPKDINVKWKIDGSERQNGVLN-SWTDQDSKDSTYSMSS TLTLTKDEYERHNSYTCEATHKTSTSPIVKSFNRNEC (SEQ ID NO: 52). In some embodiments, the light chain consists of SEQ ID NO: 52. Antibody #3, as referred to in this application, was sequenced and found to have a light chain consisting of SEQ ID NO: 52. The CDRs of this light chain, as determined using Chothia scheme, are SEQ ID NOs: 27-29.

In some embodiments, the agent binds as a monomer. In some embodiments, the agent binds as a dimer. In some embodiments, the agent binds as a monomer and/or a dimer. In some embodiments, the agent binds as a dimer, but does not bind mCD28. In some embodiments, the agent binds as a dimer, but does not crosslink and/or activate mCD28. In some embodiments, the agent binds as a dimer, but only binds a single molecule of CD28. In some embodiments, the agent binds monomeric CD28. In some embodiments, the agent binds dimeric CD28. In some embodiments, the agent binds monomeric and/or dimeric CD28.

In some embodiments, the antibody or antigen binding fragment thereof is an anti-CD28 antibody. In some embodiments, the target antigen of the antibody is CD28, sCD28, dimeric CD28 and/or dimeric sCD28. In some embodiments, the target antigen of the antibody is CD28, sCD28, monomeric CD28 and/or monomeric sCD28. In some embodiments, the target antigen of the antibody is CD28, sCD28, monomeric CD28, monomeric sCD28, dimeric CD28 and/or dimeric sCD28. In some embodiments, the sCD28 or CD28 is monomeric. In some embodiments, the sCD28 or CD28 is dimeric. In some embodiments, the CD28 or sCD28 is monomeric or dimeric. In some embodiments, the antibody or antigen binding fragment thereof is an anti-soluble CD28 (sCD28) antibody. An "anti-CD28 antibody", "an antibody which recognizes CD28", or "an antibody against CD28" is an antibody that binds CD28, with sufficient affinity and specificity. In some embodiments, the antibody has increased binding to CD28 or sCD28. In some embodiments, the antibody has increased binding to sCD28 as compared to membranal mCD28. In some embodiments, the antibody has increased binding to sCD28 as compared to a commercially available CD28 antibody. In some embodiments, the commercially available CD28 antibody is CD28.2. In some embodiments, the antibody or antigen-binding fragment thereof has specific binding affinity for CD28 or sCD28.

As used herein, the terms "increased binding affinity" and "greater binding affinity" are interchangeable. In some embodiments, antibody or antigen-binding portion thereof of the present invention has a greater binding affinity to sCD28 compared to the mCD28. In one embodiment, greater affinity as used herein is by 10%. In one embodiment, greater affinity as used herein is by 30%. In one embodiment, greater affinity as used herein is by 50%. In one embodiment, greater affinity as used herein is by 75%. In one embodiment, greater affinity as used herein is by 100%. In one embodiment, greater affinity as used herein is by 150%. In one embodiment, greater affinity as used herein is by 250%. In one embodiment, greater affinity as used herein is by 500%. In one embodiment, greater affinity as used herein is by 1,000%. In one embodiment, greater affinity as used herein is by 1.5-fold. In one embodiment, greater affinity as used herein is by 2-fold. In one embodiment, greater affinity as used herein is by 5-fold. In one embodiment, greater affinity as used herein is by 10-fold. In one embodiment, greater affinity as used herein is by 50-fold. In one embodiment, greater affinity as used herein is by 100-fold. In one embodiment, greater affinity as used herein is by 500-fold. In one embodiment, greater affinity as used herein is by 1,000-fold.

An "antigen" is a molecule or a portion of a molecule capable of eliciting antibody formation and being bound by an antibody. An antigen may have one or more than one epitope. The specific reaction referred to above is meant to indicate that the antigen will react, in a highly selective manner, with its corresponding antibody and not with the multitude of other antibodies which may be evoked by other antigens.

The term "antigenic determinant" or "epitope" according to the invention refers to the region of an antigen molecule that specifically reacts with particular antibody. Peptide sequences derived from an epitope can be used, alone or in conjunction with a carrier moiety, applying methods known in the art, to immunize animals and to produce additional polyclonal or monoclonal antibodies.

In some embodiments, the antibody comprises an N-linked glycosylation at N304 of the heavy chain.

In some embodiments, the agent is an antibody or antigen binding fragment thereof. In some embodiments, the antigen binding fragment is a Fab fragment. In some embodiments, the antibody is a single domain antibody. In some embodiments, the antibody lacks a Fc domain. In some embodiments, the agent is an antigen binding domain that lacks an Fc domain. In some embodiments, the agent is a single-domain antibody. In some embodiments, the agent is a camelid, shark or nanobody. In some embodiments, the antibody or fragment is fused to another protein or fragment of a protein. In some embodiments, the second protein or fragment increases half-life, particularly in serum. In some embodiments, the half-life extending protein is human serum albumin. In some embodiments, the agent is modified by a chemical that produces a modification that enhances half-life. In some embodiments, the modification is PEGylation and the chemical is polyethylene glycol. A skilled artisan will appreciate that any half-life extending protein or chemical agent, or modification known in the art may be used.

In some embodiments, binding of the agent to sCD28 degrades sCD28. In some embodiments, the binding of the agent to sCD28 leads to or results in degradation of sCD28. In some embodiments, the degradation occurs when the binding is within an organism. In some embodiments, the degradation occurs when the binding is in the bloodstream of an organism. In some embodiments, the degradation occurs when the binding is in the TME of an organism. In some embodiments, degradation comprises removal of sCD28 from blood. In some embodiments, the degradation comprises transport of the bound sCD28 to a lysosome, endosome, proteasome or a combination thereof. Each possibility represents a separate embodiment of the invention.

In some embodiments, binding of the agent to sCD28 in an organism results in removal of sCD28 from blood. In some embodiments, binding of the agent to sCD28 in an organism results in sweeping of the sCD28 from blood. In some embodiments, binding of the agent to sCD28 in an organism results in removal of sCD28 from the TME. In some embodiments, binding of the agent to sCD28 in an organism results in sweeping of the sCD28 from the TME. In some embodiments, binding of the agent to sCD28 in an organism results in removal of sCD28 from blood, the TME or both. In some embodiments, binding of the agent to sCD28 in an organism results in sweeping of the sCD28 from blood, the TME or both. In some embodiments, the sCD28 is not degraded, but is removed from blood, the TME or both. In some embodiments, the bound sCD28 is an immune complex.

There are many known mechanisms that remove bound antigens from the bloodstream. These include but are not limited to complement mediated removal, phagocytosis by monocytes and macrophages, opsonization, proteolysis, passive diffusion, and active transport. In some embodiments, the active transport is by red blood cells. In some embodiments, the bound antigen is transported to a phagocyte. In some embodiments, the bound antigen is transported to a lysosome. In some embodiments, the bound antigen is transported to a lysosome, endosome, proteasome, or a combination thereof. Any agent that can induce removal of the bound sCD28 complex can be used for the invention.

In some embodiments, the agent reduces sCD28 levels by at least 5, 10, 15, 20, 25, 30, 35, 40, 45, 50, 55, 60, 65, 70, 75, 80, 85, 90, 95, 97 or 99%. Each possibility represents a separate embodiment of the invention. In some embodiments, the agent reduces sCD28 levels to that of a healthy individual. In some embodiments, the agent reduces sCD28 levels to at most 1, 2, 3, 4, 5, 10, 15, 20, 25, 30, 35, 40, 45, or 50 ng/ml. Each possibility represents a separate embodiment of the invention. In some embodiments, the agent reduces sCD28 blood levels to at most 5 ng/ml. In some embodiments, the agent reduces sCD28 blood levels to at most 10 ng/ml. In some embodiments, the agent reduces sCD28 blood levels to at most 20 ng/ml. In some embodiments, the agent reduces sCD28 levels to that of a healthy individual. In some embodiments, the agent reduces sCD28 levels to below 1, 2, 3, 4, 5, 10, 15, 20, 25, 30, 35, 40, 45, or 50 ng/ml. Each possibility represents a separate embodiment of the invention. In some embodiments, the agent reduces sCD28 levels to below 5 ng/ml. In some embodiments, the agent reduces sCD28 levels to below 10 ng/ml. In some embodiments, the agent reduces sCD28 levels to below 20 ng/ml. In some embodiments, the reducing or decreasing occurs in blood, peripheral blood or the TME of the subject. In some embodiments, the reducing or decreasing occurs in blood.

In some embodiments, sCD28 levels are as measured by ELISA. In some embodiments, the ELISA is a sandwich ELISA. In some embodiments, the ELISA is a standardized sandwich ELISA. In some embodiments, the ELISA is a Bender MedSystems ELISA. In some embodiments, the ELISA is Bender MedSystems ELISA kit BMS290. In some embodiments, the ELISA is performed with an agent of the invention.

In some embodiments, the agent is a sweeping antibody. As used herein, the term "sweeping antibody" refers to any antibody or antigen binding fragment thereof that decreases the amount of a soluble component from a solution. In some embodiments the sweeping antibody does not induce antibody dependent cell-mediated cytotoxicity (ADCC). In some embodiments, the sweeping antibody does not induce complement-dependent cytotoxicity (CDC). In some embodiments, the sweeping antibody does not induce ADCC and/or CDC. In some embodiments, the sweeping antibody comprises an IgG2 or IgG4 domain. In some embodiments, the sweeping antibody comprises an IgG2 domain. In some embodiments, the sweeping antibody comprises an IgG4 domain. In some embodiments, the sweeping antibody comprises an IgG1 or IgG3 mutated to reduce cell death mediated by binding of the antibody. In some embodiments, the mutation mutates a Fc receptor binding domain. In some embodiments, a Fc domain of the antibody is engineered or mutated to decrease CDC, ADCC or both. Fc engineering is well known in the art, and any mutation or amino acid change that is known to decrease antibody mediated cell killing may be used.

In some embodiments, the antibody does not comprise IgG1 and/or IgG3. In some embodiments, the antibody does not induce antibody-dependent cell-mediated cytotoxicity (ADCC). In some embodiments the antibody does not induce complement-dependent cytotoxicity (CDC). In some embodiments, the antibody comprises an IgG1 or IgG3 comprising a mutation that reduces ADCC, CDC or both induced by the antibody's binding. In some embodiments, the mutation reduces the ADCC, CDC or both to nothing. ADCC and CDC are well characterized and antibody sequences that allow for these cytotoxic pathways to be induced are well known. Mutations, such as for non-limiting examples, mutation of IgG1 or IgG3 to IgG2 or IgG4 are well known. Any such mutation may be used in the backbone of the antibodies of the invention.

In some embodiments, the Fc domain of the antibody is a human Fc domain. In some embodiments, the Fc domain comprises a mutation that reduces the ADCC, CDC or both. In some embodiments, the antibody comprises a mutation that increases dissociation of the antibody or antigen binding portion thereof from sCD28 at low pH. In some embodiments, the low pH is a pH at or below 6.9, 6.8. 6.7, 6.6, 6.5, 6.4, 6.3, 6.2, 6.1, 6, 5.9, 5.8, 5.7, 5.6, 5.5, 5.4, 5.3, 5.2, 5.1, 5, 4.5, 4, 3.5 or 3. Each possibility represents a separate embodiment of the invention. In some embodiments, low pH is at or below a pH of 6. In some embodiments, low pH is the pH found in a human endosome. In some embodiments, low pH is the pH found in a human lysosome. In some embodiments, the antibody comprises a mutation that increases dissociation of the antibody or antigen binding portion thereof from sCD28 at low calcium concentration. In some embodiments, the low calcium concentration is the calcium concentration at or below 1.2, 1.1, 1.0, 0.9, 0.8, 0.7, 0.6, 0.5, 0.4, 0.3, 0.2, 0.1, 0.07, 0.05, 0.03, or 0.01 mM. Each possibility represents a separate embodiment of the invention. In some embodiments, the low calcium concentration is the calcium concentration found in a human endosome. In some embodiments, the mutation that increases dissociation is a mutation in a CDR. In some embodiments, the antibody comprises a mutation that increased dissociation of the antibody from sCD28 in the endosome and/or lysosome.

In some embodiments, the mutation is in the FcRn binding region. In some embodiments, the mutation is in the FcγRIIb binding region. In some embodiments, the mutation increases binding to a Fc receptor. In some embodiments, the Fc receptor is FcRn. In some embodiments, the Fc receptor is FcγRIIb. In some embodiments, the mutation increases Fc receptor binding at neutral pH and/or in serum. In some embodiments, the mutation increases Fc receptor binding at low pH. In some embodiments, the mutation is selected from mutation to a histidine of amino acid 27 of the heavy chain, amino acid 31 of the heavy chain, amino acid 32 of the light chain and amino acid 53 of the light chain. In some embodiments, the mutation increases uptake into cells of the antibody and its bound antigen.

Examples of mutations that increase Fc receptor binding, increase uptake into a cell, increase dissociation at low pH, and/or are useful in generating sweeping antibodies, are well known in the art. Examples of such can be found in, for example, Schroter et al., A generic approach to engineer antibody pH-switches using combinatorial histidine scanning libraries and yeast display, mAbs, 2015; Yang et al., Maximizing in vivo target clearance by design of pH-dependent target binding antibodies with altered affinity to FcRn, mAbs, 2017; and Igawa et al., Sweeping antibody as a novel therapeutic antibody modality capable of eliminating soluble antigens from circulation, Immunological Reviews, 2016, all of which are incorporated herein by reference in their entirety. Methods of generating such antibodies as well of testing their efficacy are also provided therein. In some embodiments, the mutation is of the human Fc domain and selected from mutation of histidine 268 to glutamine, valine 309 to leucine, alanine 330 to serine and proline 331 to serine. The numbering provided is for IgG1, but comparable mutations, such as can be determined by a skilled artisan, may be made in other IgGs. Further, the efficacy of such antibodies can be examined by performing binding/dissociate assays in media of various pHs. Tests in model organisms such as mice and monkeys are also possible, in which serum levels of sCD28 are measured before and after addition of the antibody. Optionally, tumors expressing human sCD28 may be xenografted to the animal to ensure serum sCD28.

In some embodiments, the antibody comprises a mutation in a CDR that decreases binding to an antigen at low pH. In some embodiments, the antigen is sCD28. In some embodiments, the mutation is mutation to a histidine. In some embodiments, at least 1, 2, 3, 4, or 5 amino acids are mutated to histidine. Each possibility represents a separate embodiment of the invention. In some embodiments, 1, 2, 3, 4, 5, 6, 7, 8, 9, or 10 amino acids are mutated to histidine. Each possibility represents a separate embodiment of the invention. In some embodiments, an amino acid outside of a CDR is mutated to a histidine.

It has been shown that incorporation of histidine residues in the binding interfaces of antibodies can be used to engineer pH-dependent binding. The basis for the pH-sensitive binding arises from the histidine's sensitivity to protonation as a result of lowered pH-values in various microenvironments, including intracellular microenvironments, more specifically endosomal vesicles, more preferably early endosomes. Protonation of a histidines' side chain in binding-interfaces can alter electrostatic interactions or induce conformational changes that lead to pH-dependent differences in binding affinity.

Incorporation of pH-sensitivity into the antigen binding site can increase the number of antigen-binding cycles, pH-dependent antibodies bind with similar high or reduced sufficient affinity to their antigens at plasma pH (pH 7.4) and show decreased binding at low pH resulting in a faster and increased dissociation of the antibody from its antigen binding site within the acidic endosome, thereby enabling recycling back to the plasma and increasing clearance of the antigen from the plasma.

His-scanning, by which each amino acid in the CDRs is replaced by a histidine and pH dependent binding is assessed, is a well-established technique known in the art. More than one histidine mutation may be combined to synergistically, or linearly increase the effect of the mutations. Combinatorial his-scanning library approaches using phage or yeast display are also well known in the art.

In some embodiments, the antibody is a sweeping antibody. In some embodiments, the antibody is a diagnostic antibody. In some embodiments, the antibody is a therapeutic antibody. In some embodiments, the antibody is an anti-cancer antibody.

In some embodiments, the agent is a non-antibody protein. In some embodiments, the peptide is a non-antibody peptide. In some embodiments, the non-antibody protein is an antibody mimetic. In some embodiments, the peptide is a polypeptide. In some embodiments, the agent is a small molecule. In some embodiments, the agent is a nucleic acid molecule. In some embodiments, the agent is a synthetic peptide. In some embodiments, the agent is a synthetic binding protein. In some embodiments, the synthetic peptide is based on a non-antibody scaffold. In some embodiments, the agent is an antibody mimetic. In some embodiments, the antibody mimetic has a molar mass of less than 100, 90, 80, 70, 60, 50, 40, 30 or 20 kDa. Each possibility represents a separate embodiment of the invention. In some embodiments, the agent is a nucleic acid aptamer. In some embodiments, the aptamer is DNA. In some embodiments, the aptamer is RNA. In some embodiments, the aptamer is DNA or RNA.

In some embodiments, the antibody is for use in treating and/or preventing cancer in a subject in need thereof. In some embodiments, the antibody is for use in improving immunotherapy in a subject in need thereof. In some embodiments, the immunotherapy is PD1 and/or PD-L1-based immunotherapy. PD-1 and PD-L1 immunotherapy is well known in the art and includes PD-1 and PD-L1 blockade, and PD-1 and PD-L1 inhibitors. Some examples include, but are not limited to pembrolizumab (Keytruda), nivolumab (Opdivo), pidilizumab, cemiplimab, atezolizumab (Tecentriq), avelumab (Bevancio), and durvalumab (Imfinzi).

Blocking Shedding of mCD28

By another aspect, there is provided an agent that binds membranal CD28 (mCD28) and inhibits proteolytic cleavage of the mCD28.

As used herein, inhibiting proteolytic cleavage refers to any reduction in proteolytic cleavage of mCD28. In some embodiments, the inhibition is a reduction in cleavage of at least 5, 10, 15, 20, 25, 30, 35, 40, 45, 50, 55, 60, 65, 70, 75, 80, 85, 90, 95, 97, 99 or 100%. Each possibility represents a separate embodiment of the invention. In some embodiments, inhibiting proteolytic cleavage maintains levels of mCD28 on immune cells. In some embodiments, inhibiting proteolytic cleavage increases levels of mCD28 on immune cells. In some embodiments, inhibiting proteolytic cleavage maintains levels of mCD28 adequate for immune-stimulation.

In some embodiments, the reduction in proteolytic cleavage is reduction in cleavage by at least one protease. In some embodiments, the reduction in proteolytic cleavage is reduction in cleavage by at least one metalloprotease. In some embodiments, the metalloprotease is ADAM10, ADAM17 or both.

In some embodiments, the agent is an antibody or antigen binding fragment thereof. In some embodiments, the antibody or fragment is fused to another protein or fragment of a protein. In some embodiments, the second protein or fragment increases half-life, particularly in serum. In some embodiments, the half-life extending protein is human serum albumin. In some embodiments, the agent is modified by a chemical that produces a modification that enhances half-life. In some embodiments, the modification is PEGylation and the chemical is polyethylene glycol. A skilled artisan will appreciate that any half-life extending protein or chemical agent, or modification known in the art may be used.

In some embodiments, the agent binds as a monomer. In some embodiments, the agent binds as a dimer. In some embodiments, the agent binds as a monomer and/or a dimer. In some embodiments, the agent binds as a dimer, but does not crosslink and/or activate mCD28. In some embodiments, the agent binds as a dimer, but only binds a single molecule of CD28. In some embodiments, the agent binds monomeric CD28. In some embodiments, the agent binds dimeric CD28. In some embodiments, the agent binds monomeric and/or dimeric CD28.

In some embodiments, the agent is not a CD28 agonist. In some embodiments, the agent is not a CD28 antagonist. In some embodiments, the agent is neither a CD28 agonist or antagonist.

In some embodiments, the agent does not bind the ligand binding domain of mCD28. In some embodiments, the agent does not obscure or block access to the ligand binding domain. In some embodiments, the agent binds the cleavage site. In some embodiments, the agent obscures or blocks access to the cleavage site. In some embodiments, the agent blocks accesses of the protease to the cleavage site. In some embodiments, the agent binds a stalk region of CD28. In some embodiments, the agent binds a membrane proximal region of mCD28. In some embodiments, the cleave site is within the stalk region. In some embodiments, the stalk region comprises the sequence GKHLCPSPLFPGPSKP (SEQ ID NO: 9). In some embodiments, the stalk region comprises the sequence KGKHLCPSPLFPGPS (SEQ ID NO: 36). In some embodiments, the stalk region comprises or consists of the sequence HVKGKHLCPSPLFPGPSKP (SEQ ID NO: 10).

In some embodiments, the cleavage site is before a leucine. In some embodiments, the cleavage site is before a valine. In some embodiments, the cleavage site is before an aromatic amino acid. In some embodiments, the cleavage site is before a leucine, valine and/or aromatic amino acid. In some embodiments, the aromatic amino acid is selected from phenylalanine, tryptophan, tyrosine and histidine. In some embodiments, the cleavage site is before any one of histidine 134, valine 135, histidine 139, leucine 140, leucine 145, and phenylalanine 146 of SEQ ID NO: 1. In some embodiments, the cleavage site is before histidine 134, valine 135, histidine 139, leucine 140, leucine 145, or phenylalanine 146 of SEQ ID NO: 1. Each possibility represents a separate embodiment of the invention. In some embodiments, the cleavage site is before leucine 145 of SEQ ID NO: 1.

In some embodiments, the agent does not modulate CD28 function and/or signaling. In some embodiments, the agent does not degrade mCD28. In some embodiments, the agent does not lead to or facilitate mCD28 degradation. In some embodiments, the signaling is mCD28-mediated immune cell activation. In some embodiments, the agent does not inhibit immune cell activation. In some embodiments, the agent does not induce CD28 receptor internalization or recycling. Co-stimulation via mCD28 is essential for immune activation of T-cells. Proteolytic cleavage removed the ligand-binding domain in the extracellular region of CD28 from the transmembrane and cytoplasmic portions of the protein which remain in the membrane. Thus, cleaved CD28 cannot signal and cannot contribute to T cell activation. Thus, an agent that blocks cleavage, and is also an antagonist does not allow for mCD28 activation. Similarly, an agent that blocks cleavage, but is also an agonist could induce aberrant T-cell activation, and potentially an autoimmune response. In some embodiments, the agent is not anti-CD28 antibody MAB342. In some embodiments, the agent is not anti-CD28 antibody clone #37407.

In some embodiments, the agent does not reduce surface levels of mCD28 on an immune cell. In some embodiments, the immune cell is a T cell. In some embodiments, the agent reduces surface levels of mCD28 by less than 50, 40, 30, 25, 20, 15, 10, 7, 5, 3, 2 or 1%. Each possibility represents a separate embodiment of the invention.

In some embodiments, the binding of the agent to a cell does not kill the cell. In some embodiments, the binding of the agent to a cell does not lead to death of the cell. In some embodiments the agent does not induce antibody dependent cell-mediated cytotoxicity (ADCC). In some embodiments, the agent does not induce complement-dependent cytotoxicity (CDC). In some embodiments, the agent does not induce ADCC and/or CDC. In some embodiments, the agent is an antibody and comprises an IgG2 or IgG4 domain. In some embodiments, the antibody comprises an IgG2 domain. In some embodiments, the antibody comprises an IgG4 domain. In some embodiments, the antibody comprises an IgG1 or IgG3 mutated to reduce cell death mediated by binding of the antibody. In some embodiments, the mutation mutates a Fc receptor binding domain. In some embodiments, a Fc domain of the antibody is engineered or mutated to decrease CDC, ADCC or both. Fc engineering is well known in the art, and any mutation or amino acid change that is known to decrease antibody mediated cell killing may be used.

In some embodiments, the agent is a non-antibody protein. In some embodiments, the agent is a small molecule. In some embodiments, the agent is a nucleic acid molecule. In some embodiments, the agent is a synthetic peptide. In some embodiments, the agent is a synthetic binding protein. In some embodiments, the synthetic peptide is based on a non-antibody scaffold. In some embodiments, the agent is an antibody mimetic. In some embodiments, the antibody mimetic has a molar mass of less than 100, 90, 80, 70, 60, 50, 40, 30 or 20 kDa. Each possibility represents a separate embodiment of the invention. In some embodiments, the agent is a nucleic acid aptamer. In some embodiments, the aptamer is DNA. In some embodiments, the aptamer is RNA. In some embodiments, the aptamer is DNA or RNA. Examples of antibody mimetics include, but are not limited to, affilins, affimers, affitins, alphabodies, anticalins, avimers, DARPins, fynomers, Kunitz domain peptides, monobodies, and nanoCLAMPS. In some embodiments, the antibody mimetic is a DARPin.

In some embodiments, the agent inhibits proteolytic cleavage by at least one protease. In some embodiments, the protease is a metalloprotease. In some embodiments, the protease is a matrix metalloprotease. In some embodiments, the protease is a serine protease. In some embodiments, the protease is a cysteine protease. In some embodiments, the protease is a threonine protease. In some embodiments, the protease is a serine, cysteine or threonine protease. In some embodiments, the protease is an aspartic protease. In some embodiments, the protease is a glutamic protease. In some embodiments, the protease is selected from an aspartic, a glutamic, a serine, a cysteine and a threonine protease. In some embodiments, the protease is an asparagine peptide lyases. In some embodiments, the protease is a sheddase. In some embodiments, the metalloprotease is an exopeptidase. In some embodiments, the metalloprotease is an endopeptidase. In some embodiments, the metalloprotease is an exopeptidase or endopeptidase. In some embodiments, the metalloprotease is zinc catalyzed. In some embodiments, the metalloprotease is cobalt catalyzed. In some embodiments, the metalloprotease is ADAM10. In some embodiments, the metalloprotease is ADAM17. In some embodiments, the metalloprotease is ADAM10 and/or ADAM17. In some embodiments, the metalloprotease is ADAM10, ADAM17 or both.

In some embodiments, an antibody or antigen binding fragment thereof comprises three heavy chain CDRs (CDR-H) and three light chain CDRs (CDR-L), wherein: CDR-H1 comprises the amino acid sequence set forth in SEQ ID NO: 30 (GFTFSSYYMS), CDR-H2 comprises the amino acid sequence as set forth in SEQ ID NO: 31 (TISDGGDNTYY-AGTVTG), CDR-H3 comprises the amino acid sequence as set forth in SEQ ID NO: 32 (IHWPYYFDS), CDR-L1 comprises the amino acid sequence as set forth in SEQ ID NO: 33 (RASSSVSYMN), CDR-L2 comprises the amino acid sequence as set forth in SEQ ID NO: 34 (ATSDLAS), and CDR-L3 comprises the amino acid sequence as set forth in SEQ ID NO: 35 (QQWSSHPPT).

In some embodiments, the antibody or antigen-binding fragment thereof comprises a heavy chain comprising the amino acid sequence DVKLVESGG-GLVKLGGSLKLSCVASGFTFSSYYMSWVRQTPEKR-LEWVATISDGGDN TYYAGTVTGRFTISRDFAKNT-LYLQMNSLTSEDTAVYYCARIHWPYYFDSWGQGTTL TVSS (SEQ ID NO: 53). In some embodiments, the variable region of the heavy chain comprises and/or consists of SEQ ID NO: 53. In some embodiments, the antibody or antigen-binding fragment thereof comprises a heavy chain comprising the amino acid sequence GACGTGAAGCTCGTG-GAGTCTGGGGGAGGCTTAGTGAAGCTTGGAGGGT CCCTGA AACTCTCCTGTGTAGCCTCTGGATT-CACTTTCAGTAGCTATTACATGTCTTGGGTTC GCCAGACTCCGGAGAAGAGGCTG-GAGTGGGTCGCGACCATAAGTGATGGTGGTGA TAACACCTACTACGCAGGCACTGTGACGGGCCGAT-TCACCATCTCCAGAGACTTTG CCAAGAACACCCTGTACCTGCAAAT-GAACAGTCTGACCTCTGAGGACACAGCCGT GTAT-TACTGTGCAAGAATTCATTGGCCTTACTAT-TTTGACTCCTGGGGCCAAGGCA CCACTCTCACAGTCTCCTCA (SEQ ID NO: 54). In some embodiments, the heavy chain consists of SEQ ID NO: 54. An anti-cleavage antibody of this application, was sequenced and found to have a heavy chain consisting of SEQ ID NO: 54. The CDRs of this heavy chain, as determined using Chothia scheme, are SEQ ID NOs: 30-32.

In some embodiments, the antibody or antigen-binding fragment thereof comprises a light chain comprising the amino acid sequence QFVLSQSPAILSASPGEMLTMT-CRASSSVSYMNWYQQKPGSSPKPWIYATSDLASGVP ARFSGSGSGTSYSLTISRVEAE-DAATYYCQQWSSHPPTFGGGTKLEIR (SEQ ID NO: 55). In some embodiments, the variable region of the light chain comprises and/or consists of SEQ ID NO: 55. In some embodiments, the antibody or antigen-binding fragment thereof comprises a light chain comprising the amino acid sequence CAAT-TTGTTCTCTCCCAGTCTCCAGCAATCCTGTCTG-CATCTCCCGGGGAGATGCTC ACAATGACTTGCAGGGCCAGCTCAAGTGTAAGT-TATATGAACTGGTATCAGCAGA AGCCAG-GATCTTCCCCCAAACCCTGGATTTATGCCA-CATCCGACCTGGCTTCTGGA GTCCCTGCTCGCTTCAGTGGCAGTGGGTCTGGGA CCTCTTATTCTCTCACAATCAGC AGAGTGGAGGCT-GAAGATGCTGCCACTTATTACTGCCAGCAGTG-GAGTAGTCACCC ACCCACGTTCGGAGGGGGGAC-CAAGCTGGAAATAAGA (SEQ ID NO: 56). In some embodiments, the light chain consists of SEQ ID NO: 56. An anti-cleavage antibody, as referred to in this application, was sequenced and found to have a light chain consisting of SEQ ID NO: 56. The CDRs of this light chain, as determined using Chothia scheme, are SEQ ID NOs: 33-35.

Methods of Treating/Preventing Cancer

By another aspect there is provided a method of treating and/or preventing cancer in a subject in need thereof, the method comprising decreasing soluble CD28 (sCD28) levels in said subject.

By another aspect there is provided a method of improving immunotherapy in a subject in need thereof, the method comprising decreasing sCD28 levels in said subject.

In some embodiments, the immunotherapy is PD-1 and/or PD-L1 based immunotherapy. In some embodiments, the PD-1/PD-L1 based immunotherapy comprises administering an anti-PD1 or anti-PD-L1 antibody. In some embodiments, the therapy comprises blockade of the PD-1 checkpoint. In some embodiments, the immunotherapy comprises administering allogenic, syngenic or autologous immune cells to the subject. In some embodiments, the immune cells are T cells. In some embodiments, the subject in need of immunotherapy suffers from cancer.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

In some embodiments, the decreasing comprises administering to the subject at least one agent of the invention. As used herein, the terms "administering," "administration," and like terms refer to any method which, in sound medical practice, delivers a composition containing an active agent to a subject in such a manner as to provide a therapeutic effect. One aspect of the present subject matter provides for oral administration of a therapeutically effective amount of an agent of the invention to a patient in need thereof. Other suitable routes of administration can include parenteral, subcutaneous, intravenous, intramuscular, or intraperitoneal.

By another aspect, there is provided a pharmaceutical composition comprising an agent of the invention and a therapeutically acceptable carrier, adjuvant or excipient. In some embodiments, the administering is administering a pharmaceutical composition of the invention.

As used herein, the term "carrier," "excipient," or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

In some embodiments, decreasing comprises administering an inhibitory nucleic acid molecule that binds to an mRNA coding for sCD28 and does not bind to mRNA coding for mCD28. One possible source of sCD28 is from translation of transcriptional variants of CD28 that lack the transmembrane domain. Such variants may have unique mRNA sequences that can be targeted in order to degrade or inhibit translation of the mRNA. For non-limiting example, sCD28 is produced by an mRNA splice variant that lacks exon 3 (SEQ ID NO: 7). In this variant the exon 2 and exon 4 junction is the only sequence which is present in the variant but lacking in full-length CD28. In some embodiments, the nucleic acid molecule binds to the at least the junction of exon 2 and exon 4 of SEQ ID NO: 7. In some embodiments, the splice junction of exons 2 and 4 comprises the sequence AAAGGTGA (SEQ ID NO: 11). In some embodiments, the nucleic acid molecule binds at least 10, 15, 20, 25, 30, 35, 40, 45, or 50 bases of SEQ ID NO: 7 including the splice junction of exons 2 and 4. Each possibility represents a separate embodiment of the invention.

In some embodiments, the nucleic acid molecule is an siRNA. In some embodiments, the molecule is an shRNA. In some embodiments, the molecule is an siRNA or an shRNA.

In some embodiments, decreasing comprises administering an agent that inhibits a protease capable of cleaving mCD28. In some embodiments, the agent inhibits ADAM10, ADAM17 or both. Protease inhibitors are well known in the art. Examples of protease inhibitors that inhibit ADAM17 and ADAM10 include, but are not limited to, TAPI-1, GM6001, and GI254023X. Further therapeutic protease inhibitors are disclosed in International Patent Application WO2004096139.

In some embodiments, decreasing comprises administering a peptide comprising a stalk region of CD28 or a fragment thereof. In some embodiments, the peptide is monomeric. In some embodiments, the peptide is dimeric. In some embodiments, the CD28 is human CD28. In some embodiments, the peptide inhibits access of the protease to the cleavage site. In some embodiments, the peptide induces production of autoantibodies that block the cleavage site.

In some embodiments, the methods of the invention do not degrade or lead to degradation of mCD28. In some embodiments, the methods of the invention do not decrease mCD28 levels on immune cells. In some embodiments, the methods of the invention do not decrease mCD28-mediated immune cell activation. In some embodiments, the methods of the invention maintain mCD28 levels on immune cells in the subject. In some embodiments, the methods of the invention increase mCD28 levels on immune cells in the subject.

In some embodiments, the reduction is at least a 10, 20, 30, 40, 50, 60, 70, 80, 90, 95, or 99% reduction in sCD28. Each possibility represents a separate embodiment of the invention. In some embodiments, the reduction is in serum sCD28. In some embodiments, the reduction is in the blood levels of sCD28. In some embodiments, the reduction is in the levels of sCD28 in the tumor microenvironment (TME).

In some embodiments, the subject's blood comprises elevated levels of sCD28. In some embodiments, the subject's blood before the decreasing comprises elevated levels of sCD28. In some embodiments, the levels are elevated above those of healthy subjects. In some embodiments, the subject's sCD28 levels are elevated by at least 5%, 10%, 15%, 20%, 25%, 30%, 40%, 50%, 60%, 70%, 80%, 90%, 100%, 150%, 200%, 250%, 300%, 350%, 400%, 500%, 600%, 700%, 800%, 900%, or 1000% above healthy subject levels. Each possibility represents a separate embodiment of the invention. In some embodiments, the levels are elevated above 5, 6, 7, 8, 9, 10, 12, 14, 15, 16, 18, 20, 25, 30, 35, 40, 45 or 50 ng/ml of blood. Each possibility represents a separate embodiment of the invention. In some embodiments, the levels are elevated above 5 ng/ml. In some embodiments, the levels are elevated above 10 ng/ml. In some embodiments, the levels are elevated above 20 ng/ml. In some embodiments, the subject's blood comprises at least 5, 6, 7, 8, 9, 10, 12, 14, 15, 16, 18, 20, 25, 30, 35, 40, 45 or 50 ng sCD28 per ml of blood. Each possibility represents a separate embodiment of the invention. In some embodiments, the subject's blood prior to the decreasing comprises at least 5, 6, 7, 8, 9, 10, 12, 14, 15, 16, 18, 20, 25, 30, 35, 40, 45 or 50 ng sCD28 per ml of blood. Each possibility represents a separate embodiment of the invention. In some embodiments, the subject's blood comprises at least 5 ng/ml sCD28. In some embodiments, the subject's blood comprises at least 10 ng/ml sCD28. In some embodiments, the subject's blood comprises at least 20 ng/ml sCD28. In some embodiments, the subject's blood prior to the decreasing comprises at least 5 ng/ml sCD28. In some embodiments, the subject's blood prior to the decreasing comprises at least 10 ng/ml sCD28. In some embodiments, the subject's blood prior to the decreasing comprises at least 20 ng/ml sCD28.

In some embodiments, the subject suffers from cancer. In some embodiments, the cancer is a cancer that can be treated with PD-1/PD-L1 therapy. In some embodiments, the subject has undergone PD-1/PD-L1 therapy. In some embodiments, the subject is a non-responder to PD-1/PD-L1 therapy. In some embodiments, the subject is naïve to PD-1/PD-L1 therapy. In some embodiments, the methods of the invention are performed together with PD-1/PD-L1 therapy. In some embodiments, the methods of the invention are performed before PD-1/PD-L1 therapy.

In some embodiments, the method further comprises administering another immunotherapy to the subject. In some embodiments, the method further comprises administering a PD-1 and/or PD-L1 based immunotherapy. In some embodiments, the another immunotherapy is a checkpoint inhibitor. In some embodiments, the checkpoint inhibitor is a PD-1 and/or PD-L1 inhibitor. In some embodiments, the checkpoint inhibitor is a CTLA-4 inhibitor. In some embodiments, the another immunotherapy is a chimeric antigen receptor (CAR) based immunotherapy. In some embodiments, the CAR is a CAR-T. In some embodiments, the CAR is a CAR-NK. In some embodiments, the another immunotherapy is a cancer vaccine.

As used herein, the terms "CAR-T cell" and "CAR-NK cell" refer to an engineered receptor which has specificity for at least one protein of interest (for example an immunogenic protein with increased expression following treatment with an epigenetic modifying agent) and is grafted onto an immune effector cell (a T cell or NK cell). In some embodiments, the CAR-T cell has the specificity of a monoclonal antibody grafted onto a T-cell. In some embodiments, the CAR-NK cell has the specificity of a monoclonal antibody grafted onto a NK-cell. In some embodiments, the T cell is selected from a cytotoxic T lymphocyte and a regulatory T cell.

CAR-T and CAR-NK cells and their vectors are well known in the art. Such cells target and are cytotoxic to the protein for which the receptor binds. In some embodiments, a CAR-T or CAR-NK cell targets at least one viral protein. In some embodiments, a CAR-T or CAR-NK cell targets a plurality of viral proteins. In some embodiments, a CAR-T or CAR-NK cell targets a viral protein with increased expression due to contact with an epigenetic modifying agent.

Construction of CAR-T cells is well known in the art. In one non-limiting example, a monoclonal antibody to a viral protein can be made and then a vector coding for the antibody will be constructed. The vector will also comprise a costimulatory signal region. In some embodiments, the costimulatory signal region comprises the intracellular domain of a known T cell or NK cell stimulatory molecule. In some embodiments, the intracellular domain is selected from at least one of the following: CD3Z, CD27, CD28, 4-1BB, OX40, CD30, CD40, PD-1, ICOS, lymphocyte function-associated antigen-1 (LFA-1), CD2, CD 7, LIGHT, NKG2C, B7-H3, and a ligand that specifically binds with CD83. In some embodiments, the vector also comprises a CD3Z signaling domain. This vector is then transfected, for example by lentiviral infection, into a T-cell.

In some embodiments, the cancer is a cancer with elevated sCD28 levels. In some embodiments, the cancer comprises high sCD28 levels. In some embodiments, elevated and/or high sCD28 levels are levels at and/or above 5, 6, 7, 8, 9, 10, 12, 14, 15, 17, 20, 25, 30, 35, 40, 50, 60, 70, 80, 90 or 100 ng/ml. Each possibility represents a separate embodiment of the invention. In some embodiments, the cancer comprises high sCD28 levels. In some embodiments, elevated and/or high sCD28 levels are levels at and/or above 5, 10, 15, 20, 25, 30, 35, 40, 45, 50, 55, 60, 65, 70, 75, 80, 85, 90, 95, 100, 150, 200, 300, 400, 500, 600, 700, 800, 900, or 1000% of the levels in a healthy subject. Each possibility represents a separate embodiment of the invention. In some embodiments, the cancer is not breast cancer. In some embodiments, the cancer is selected from melanoma, head and neck, non-small cell lung cancer, ovarian, kidney, gastric and colorectal. In some embodiments, the cancer is selected from melanoma, head and neck, non-small cell lung cancer, ovarian, and colorectal. In some embodiments, the cancer is melanoma, head and neck, non-small cell lung cancer, ovarian, kidney, gastric or colorectal. Each possibility represents a separate embodiment of the invention.

In some embodiments, the method is performed in vivo. In some embodiments, the method is performed in vitro. In some embodiments, the decreasing is performed in vivo. In some embodiments, the decreasing is performed in vitro. In some embodiments, the decreasing comprises removing blood from the subject decreasing the sCD28 levels in the removed blood and returning the blood to the subject, thereby decreasing sCD28 in the subject. Methods of dialysis and blood cleaning are well known. The invention may be practiced by in vitro sweeping away the sCD28 and then returning the blood to the subject.

Methods of Use

By another aspect, there is provided a method of in vitro detecting sCD28 in a sample the method comprising:
  a. providing a sample comprising sCD28;
  b. contacting the sample with an agent of the invention; and
  c. detecting the agent bound to sCD28;
thereby detecting sCD28 in the sample.

In some embodiments, the sample is from a subject. In some embodiments, the sample comprises a bodily fluid. In some embodiments, the sample comprises tissue. In some embodiments, the sample comprises cells. In some embodiments, the detection is by a secondary antibody. In some embodiments, the detection is which a tagged molecule that binds the agent. In some embodiments, the detection is by ELISA. In some embodiments, the detection is by immunohistochemistry. In some embodiments, the detection is by immunoblot. In some embodiments, the agents of the invention are for detecting sCD28. In some embodiments, the agents of the invention are for detecting sCD28 while not detecting mCD28.

By another aspect, there is provided a method of determining suitability of a subject to be treated by a therapeutic method of the invention, comprising providing a sample from the subject, and determining sCD28 levels in the sample, wherein an elevated sCD28 level indicates the subject is suitable to be treated by a therapeutic method of the invention.

By another aspect, there is provided a method of determining suitability of a subject to be treated by anti-PD-1 and/or PD-L1 immunotherapy and/or by CD80 and/or CD86 based immunotherapy, the method comprising providing a sample from the subject, and determining sCD28 levels in the sample, wherein a sCD28 level above 5 ng/ml indicates the subject is unsuitable to be treated by anti-PD-1 and/or PD-L1 immunotherapy or by CD80 and/or CD86 based immunotherapy.

By another aspect, there is provided a method for making an unsuitable subject suitable to receive anti-PD-1 and/or PD-L1 immunotherapy and/or CD80 and/or CD86 based immunotherapy, the method comprising decreasing sCD28 levels in the unsuitable subject, thereby making them suitable.

By another aspect, there is provided a method of improving CD80 and/or CD86 based immunotherapy in a subject, the method comprising:

a. measuring sCD28 levels in the subject; and
  b. increasing the dose of CD80 and/or CD86 based immunotherapy to a subject comprising a sCD28 level above 5 ng/ml;
thereby improving CD80 and/or CD86 based immunotherapy.

In some embodiments, the method further comprises making the unsuitable subject suitable by performing a method of the invention.

In some embodiments an elevated level is elevated about a level in a healthy subject. In some embodiments an elevated level is elevated about a level in a predetermined threshold. In some embodiments, an elevated level is sCD28 level above 5, 10, 15, 20, 25, 30, 35, 40, 45, or 50 ng/ml. Each possibility represents a separate embodiment of the invention. In some embodiments, a sCD28 level above 5, 10, 15, 20, 25, 30, 35, 40, 45, or 50 ng/ml. indicates the subject is unsuitable to be treated. Each possibility represents a separate embodiment of the invention. In some embodiments, a sCD28 level above 10 indicates the subject is unsuitable to be treated. In some embodiments, a sCD28 level above 20 indicates the subject is unsuitable to be treated.

CD80 and CD86 immunotherapies are well known in the art and comprise administering CD80/CD86 and or mimic, derivatives or mimetics thereof to stimulate an immune response. CD80-Fc is currently in clinical trials as an anticancer immunotherapeutic for non-limiting example.

In some embodiments, detecting the agent bound to sCD28 comprises determining the amount of bound sCD28. In some embodiments, detecting the amount of bound sCD28 is determining the amount of sCD28 in the bodily fluid. In some embodiments, the method is for determining suitability of the subject to be treated with the pharmaceutical composition of the invention. In some embodiments, a level of sCD28 above a predetermined threshold indicates the subject is suitable for treatment with the composition of the invention. In some embodiments, the method is for determining suitability of the subject for immunotherapy. In some embodiments, a level of sCD28 below a predetermined threshold, or the absence of sCD28 indicates the subject is suitable for immunotherapy. In some embodiments, a level of sCD28 above a predetermined threshold indicates the subject is suitable for combined immunotherapy and the composition of the invention.

In some embodiments, the subject suffers from cancer. In some embodiments, the subject is at risk for developing cancer.

In some embodiments, the method further comprises administering to the subject the pharmaceutical composition of the invention. In some embodiments, the method further comprises administering to the subject the pharmaceutical composition of the invention when the detected sCD28 is above a predetermined threshold. In some embodiments, the method further comprises administering to the subject an immunotherapy.

Kits

By another aspect, there is provided a kit comprising at least one agent of the invention, or the pharmaceutical composition of the invention.

In some embodiments, the kit further comprises a PD-1 and/or PD-L1 based immunotherapeutic. In some embodiments, the kit comprises a label stating the agent of the invention is for use with a PD-1 and/or PD-L1 based immunotherapeutic. In some embodiments, the kit comprises a label stating the PD-1 and/or PD-L1 based therapeutic is for use with an antibody or pharmaceutical composition of the invention.

In some embodiments, the kit further comprises a detection molecule for detecting an agent of the invention. In some embodiments, the detection molecule is a secondary detection molecule. In some embodiments, the detection molecule binds to the agent. Detection molecules are well known in the art, and include, but are not limited to fluorescent moieties and molecule, dyes, and secondary antibodies.

By another aspect, there is provided a kit comprising a PD-1 and/or PD-L1 based immunotherapeutic comprising a label stating it is for use with an antibody or pharmaceutical composition of the invention.

In some embodiments, a kit of the invention is for use in treating cancer. In some embodiments, a kit of the invention is a diagnostic kit. In some embodiments, a kit of the invention is for use in determining serum levels of sCD28 in a subject in need thereof. In some embodiments, the subject suffers from cancer. In some embodiments, a kit of the invention is for use in determining suitability of a subject to be treated with an agent or pharmaceutical composition of the invention. In some embodiments, the kit is for use in determining suitability of a subject to be treated with anti-PD-1/PD-L1 based immunotherapy.

Methods of Agent Generation

By another aspect, there is provided a method for producing an agent of the invention, the method comprising:
a. obtaining an agent that binds specifically to a CD28 extracellular domain or fragment thereof, and
b. testing an ability of the agent to block cleavage of mCD28 by a protease, and selecting at least one agent that blocks cleavage of mCD28 by the protease;
thereby producing an agent of the invention.

By another aspect, there is provided a method for producing an agent of the invention, the method comprising:
culturing a host cell comprising one or more vectors comprising a nucleic acid sequence encoding an agent, wherein the nucleic acid sequence is that of an agent that was selected by:
i. obtaining an agent that binds to a CD28 extracellular domain or fragment thereof,
ii. testing an ability of the agent to block cleavage of mCD28 by a protease; and
iii. selecting at least one agent that blocks cleavage of mCD28 by the protease;
thereby producing an agent of the invention.

In some embodiments, the agent is an anti-cleavage agent. In some embodiments, the agent is an anti-shedding agent. In some embodiments, the agent decreases shedding of sCD28 in a subject. In some embodiments, the agent decreases cleavage of mCD28. In some embodiments, the agent decreases cleavage of mCD28 in a subject.

In some embodiments, the protease is ADAM10. In some embodiments, the protease is ADAM17. In some embodiments, the protease is ADAM10, ADAM17 or both.

As used herein, the term "extracellular domain of CD28" refers to the N-terminal portion of CD28 that comes before the transmembrane domain. In some embodiments, an extracellular domain of CD28 is sCD28. In some embodiments, an extracellular domain of CD28 is CD28a. In some embodiments, an extracellular domain of CD28 is the CD28 stalk domain. In some embodiments, an extracellular domain of CD28 comprises the stalk domain of CD28. In some embodiments, an extracellular domain of CD28 comprises or consists of the sequence NKILVKQSPMLVAYD-NAVNLSCKYSYNLFSREFRASLHKGLDSAVEVCV-VYGNYSQQ LQVYSKTGFNCDGKLGNESVTFYLQN-LYVNQTDIYFCKIEVMYPPPYLDNEKSNGTIIH VKGKHLCPSPLFPGPSKP (SEQ ID NO: 37). In some embodiments, the extracellular domain of CD28 or a fragment thereof is dimeric. In some embodiments, the extracellular domain of CD28 or a fragment thereof is monomeric. In some embodiments, the extracellular domain of CD28 or a fragment thereof is dimeric or monomeric.

As used herein, a "fragment" refers to a partial polypeptide that makes up part of the larger protein or protein domain. In some embodiments, a fragment comprises at least 10, 20, 30, 40 or 50 amino acids. Each possibility represents a separate embodiment of the invention. In some embodiments, a fragment comprises at most 10, 20, 30, 40, 50, 60 70, 80, 90 or 100 amino acids. Each possibility represents a separate embodiment of the invention. In some embodiments, obtaining an agent that binds a fragment of the extracellular domain of CD28 is obtaining an agent that binds specifically to a CD28 stalk domain.

In some embodiments, the method further comprises assaying mCD28 downstream signaling in the presence of the obtained agent and selecting at least one agent that neither substantially agonizes nor substantially antagonizes mCD28 signaling. In some embodiments, the selecting is selecting at least one agent that does not antagonize mCD28 signaling. It will be understood by a skilled artisan that for cancer treatment agonizing CD28 signaling might not be deleterious, but that antagonizing the signaling would be counterproductive.

In some embodiments, testing an agent's ability to block cleavage is by a method described hereinbelow. In some embodiments, testing an agent's ability to block cleavage comprises mixing of the agent, the protease and an extracellular domain of CD28 or a fragment thereof comprising a cleavage site. In some embodiments, the testing further comprises sequencing the extracellular domain of CD28 or a fragment thereof to check for truncation and/or cleavage. In some embodiments, the testing further comprises run the extracellular domain of CD28 or a fragment thereof on a gel that is sufficiently sensitive to measure the size change due to cleavage. In some embodiments, the testing further comprises measuring the production of sCD28 from cells expressing mCD28 in the presence of the agent and the protease.

By another aspect, there is provided a method for producing an agent of the invention, the method comprising:
a. obtaining an agent that binds to a CD28 extracellular domain or fragment thereof, and
b. assaying mCD28 downstream signaling in the presence of the obtained agent, and selecting at least one agent that neither substantially agonizes nor substantially antagonizes mCD28 signaling;
thereby producing an agent of the invention.

By another aspect, there is provided a method for producing an agent of the invention, the method comprising:
culturing a host cell comprising one or more vectors comprising a nucleic acid sequence encoding an agent, wherein the nucleic acid sequence is that of an agent that was selected by:
i. obtaining an agent that binds to a CD28 extracellular domain or fragment thereof,
ii. assaying mCD28 downstream signaling in the presence of said obtained agent; and
iii. selecting at least one agent that neither substantially agonizes nor substantially antagonizes mCD28 signaling;
thereby producing an agent of the invention.

In some embodiments, the agent is a sweeping agent. In some embodiments, the agent is for removing sCD28 from a subject. In some embodiments, the agent specifically binds to CD28. In some embodiments, the agent specifically binds to sCD28.

In some embodiments, the method further comprises isolating and/or extracting the agent from the host cell. In some embodiments, the method further comprises isolating and/or extracting the agent from the culture media of the host cell. In some embodiments, the method further comprises purifying the agent from the host cell or the culture media of the host cell.

In some embodiments, the method further comprises testing binding of the obtained agent to mCD28 and selecting at least one agent that does not bind mCD28. In some embodiments, the method further comprises testing binding of the obtained agent to sCD28 from a subject and selected at least one agent that binds the sCD28 from a subject. In some embodiments, the subject is a cancer patient. In some embodiments, the subject is an autoimmune patient.

In some embodiments, obtaining the agent comprises immunizing an organism with the CD28 extracellular domain or fragment thereof, and collecting antibodies from the immunized organism. In some embodiments, the organism is a mouse. In some embodiments, the organism is selected from a rabbit, a mouse, a rat, a shark, a camelid, a chicken a goat and a phage. In some embodiments, the camelid is selected from a camel and a llama. In some embodiments, the collecting comprises drawing blood. In some embodiments, the collecting comprises:
a. extracting B cells from a spleen of the immunized organism;
b. fusing the extracted B cells with myeloma cells to produce a hybridoma; and
c. collecting antibodies from the hybridoma.

In some embodiments, obtaining the agent comprises screening a library of agents for binding to a CD28 extracellular domain or fragment thereof and selecting an agent that so binds. In some embodiments, the library is a phage display library. In some embodiments, the library is an immunized library derived from splenic B cells. In some embodiments, the library is an IgG library. In some embodiments, the library is a Fab library. In some embodiments, the library is a library of VHH antibodies. In some embodiments, the library is a library of single chain, single domain or nanobodies. In some embodiments, obtaining the agent comprises sequencing the agent. In some embodiments, obtaining the agent comprises producing a recombinant form of the agent. In some embodiments, selecting the agent comprises sequencing the agent. In some embodiments, selecting the agent comprises producing a recombinant form of the agent. In some embodiments, the recombinant form is produced from the sequence of the agent. In some embodiments, the method further comprises humanizing the agent.

Expressing of a nucleic acid molecule that encodes an agent within a cell is well known to one skilled in the art. It can be carried out by, among many methods, transfection, viral infection, or direct alteration of the cell's genome. In some embodiments, the gene is in an expression vector such as plasmid or viral vector. One such example of an expression vector containing p16-Ink4a is the mammalian expression vector pCMV p16 INK4A available from Addgene.

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the nucleic acid sequence encoding an agent is operably linked to a promoter. The term "operably linked" is intended to mean that the nucleotide sequence of interest is linked to the regulatory element or elements in a manner that allows for expression of the nucleotide sequence (e.g. in an in vitro transcription/translation system or in a host cell when the vector is introduced into the host cell).

In some embodiments, the vector is introduced into the cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like.

The term "promoter" as used herein refers to a group of transcriptional control modules that are clustered around the initiation site for an RNA polymerase i.e., RNA polymerase II. Promoters are composed of discrete functional modules, each consisting of approximately 7-20 bp of DNA, and containing one or more recognition sites for transcriptional activator or repressor proteins.

In some embodiments, nucleic acid sequences are transcribed by RNA polymerase II (RNAP II and Pol II). RNAP II is an enzyme found in eukaryotic cells. It catalyzes the transcription of DNA to synthesize precursors of mRNA and most snRNA and microRNA.

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO01/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

By another aspect, there is provided an agent produced by a method of the invention.

By another aspect, there is provided a pharmaceutical composition comprising an agent produced by a method of the invention and a pharmaceutically acceptable carrier, excipient or adjuvant.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Antibodies—Commercial mouse monoclonal anti-CD28 clone #CD28.2 (Biolegend, Cat. No. 302902) and FITC conjugated (Biolegend, Cat. No. 302906). Goat polyclonal anti-CD28 (R&D system, Cat. No. AF-342-PB). FITC conjugated anti-Human PD-L1 (BD bioscience, Cat. No. 558065). APC conjugated anti-Human PD-L2 (Biolegend, Cat. No. 345508). PE conjugated anti-Human IDO (R&D system, Cat. No. IC6030P). Goat anti mouse IgG Alexa Fluor 647 (Biolegend, Cat. No. 405322). Donkey anti human IgG (H+L) Alexa Fluor 647 (Jackson immune research, Cat. No. 709-605-149). Goat anti mouse IgG HRP (Jackson immune research, Cat. No. 115-035-071). Anti-Human CD3 clone OKT3 (Biolegend, Cat. No. 317304). Anti-Human PD-1 pembrolizumab (MK-3475). Human IgG (Sigma, cat #I4506).

Production of recombinant soluble human CD28a—CD28a cDNA was subcloned in the pCDNA3·1 vector with a c-terminal TEV protease cleaving site before six histidine residues to facilitate affinity purification. The plasmid was used to transfect HEK293 cells and soluble recombinant CD28a was purified via Immobilized Metal Affinity Chromatography (IMAC). Pooled material was subjected to His-tag cleavage using TEV Protease following a second IMAC to remove His-tags and TEV Protease.

ELISA—Commercial ELISA kits were used for quantitation of the amount of human interferon-gamma (Biolegend, Cat. No. 430103), human interleukin 2 (Biolegend, Cat. No. 431802), human interleukin 6 (Biolegend, Cat. No. 430502), human interleukin 10 (Biolegend, Cat. No. 430603), human tumor growth factor beta 1 (Biolegend, Cat. No. 436708), human interleukin beta 1 (Biolegend, Cat. No. 437004) and human CD28 (R&D system, Cat. No. DY342). Cell Proliferation and viability (MTT assay) was conducted according to manufacturer instructions (Roche, cat #11465007001). Kynurenine (IDO activity) ELISA kit was conducted according to manufacturer instructions (ImmuSmo Cat #BA E-2200).

Cytokine multiplex—The simultaneous evaluation of several cytokines was carried out using ProcartaPLex (Invitrogen, Cat. No. PPX-07-MXXGPY2) on the Magpix system (Millipore).

Flow Cytometry—Generally, cells were kept on ice during all steps. Prior to staining, $5\times10^5$ cells were blocked with 50 µg/mL human IgG (Sigma, Cat. No. 14506) in FACS buffer (PBS with 0.1% BSA) for 15 min. Antibodies were used at concentrations recommended by the manufacturer and incubated for 30 min. in the dark. Incubations were done in a volume of 100 µL in 96-well U bottom plates. Cells were washed twice with 200 µL of FACS buffer and transferred to FACS tubes in 150 µL of FACS buffer for analysis. Cells were analyzed on a Gallios Flow Cytometer (Beckman Coulter) using the Kaluza for Gallios Flow Cytometry Acquisition Software.

Cell lines and isolation of human immune cells—Jurkat leukemic T-cell lymphoblast cell line clone E6.1 and SCC-25 tongue squamous cell carcinoma were obtained from the ATCC. PBMCs were isolated from fresh blood samples of healthy donors using standard lymphocytes separation medium (MBP, Cat. No. 850494). CD3 cells were isolated from fresh blood samples of healthy donors using RossetteSEP™ Human T cells Enrichment Kit (STEMCELL, Cat. No. 15061) by negative selection method. CD4 cells were isolated from fresh blood samples of healthy donors using EasySep™ Human CD4 T cells Enrichment Kit (STEMCELL, Cat. No. 19059) by negative selection method. Monocytes were isolated from fresh blood samples of healthy donors using EasySep™ Human Monocyte Enrichment Kit (STEMCELL, Cat. No. 17952) by negative selection method. All cells were grown in complete RPMI-1640 media supplemented with 10% HI-FCS and pen/strep mixture.

Dendritic cell differentiation—monocytes were cultured at a density of $1\times10^6$/mL in RPMI medium with growth factors that was refreshed at day 3 and at day 6. Immature dendritic cells (iDCs) were induced by 50 ng/mL GM-CSF and 20 ng/mL IL-4 for 6 days. When needed the iDCs were further differentiated into mature dendritic cells by addition of 100 ng/mL LPS for 48 hrs. The generated cell populations were tested for the indicated phenotypes by FACS analysis of relevant markers and by analysis of secretion of characteristic cytokines.

Protease Inhibitors—Protease inhibitors were added at the indicated concentrations at the start of each experiment. In week long assays another portion of the inhibitors was added after 3 days at the final concentration. Protease inhibitors used are TAPI-1 (Cayman, Cat. No. 18505), GM6001 (Santa Cruz, Cat. No. SC-203979), TMI-1 (Sigma, Cat. No. PZ0336) and GI254023X (Sigma, Cat. No. SML0789). Where mentioned the protease cocktail was composed with a mixture of TAPI-1 and GM6001 at equimolar ratio.

PHA activation of CD4 T cells or Jurkat T cell line for the generation of soluble CD28—$1\times10^5$ Jurkat cells or CD4 T cells were incubated with the indicated concentration of Phytohemagglutinin (Sigma, Cat. No. L8902) and various protease inhibitors for additional 5 (Jurkat) or 7 days (CD4 T cells).

SEB or CMV activation of PBMCs for the generation of soluble CD28—$0.3\times10^6$ PBMCs were stimulated with 0.5 ng/mL SEB (Sigma, Cat. No. S4881) for 5-7 days at 37° C. with/without the indicated concentration of various protease inhibitors in 48 well plate. Alternatively, $0.1\times10^6$ PBMCs were stimulated with 0.5 ng/mL SEB in 96 well plate format assay. For CMV stimulation $0.5\times10^6$ PBMCs were stimulated with 0.5 µg/mL CMV peptivator (Milteny Biotec, Cat. No. 130-093-435) for 2-5 days at 37° C. with/without the indicated concentration of various protease inhibitors in a 96 well plate. For continuous shedding experiments PBMC were stimulated with SEB or CMV in 24 well plate for 24 hr, cells were taken and washed three times with RPMI without stimulant and plated again in a 96 well plate. Samples were taken at indicated times and put under freezing conditions until examination for soluble CD28.

Mixed lymphocyte reaction—$1\times10^5$ immature DCs were mixed with $5\times10^5$ isolated autogenic CD3 T cells for 6 days.

SEB or CMV stimulation assay with ectopic recombinant human CD28, human CTLA-4 and human CD80—For CMV stimulation $0.5\times10^6$ PBMCs (from healthy or cancer patients donors) were stimulated with 0.5 µg/mL CMV peptivator (Milteny Biotec, Cat. No. 130-093-435) for 2-5 days at 37° C. with/without the indicated concentration of recombinant human CD28 (R&D systems, Cat. No. 342-CD), human CTLA-4 (R&D systems, Cat. No. 434-CT), human CD80 (R&D systems, Cat. No. 140-B1) in a 96 well plate. For SEB setting, $1\times10^5$ PBMCs were cultured with 0.5 ng/mL Staphylococcal Enterotoxin B (SEB) (Sigma, Cat. No. S4881) concentrations in the presence of indicated concentration of rec. human CD28 for 72 hrs. Where specified, anti-PD1 or human IgG were added at a final concentration of 5 µg/mL.

Autologous monocytes CD3 MLR—$0.5\times10^6$ T cells were mixed with $0.5\times10^5$ monocytes from same CMV reactive donor and stimulated with 0.5 µg/mL CMV peptivator for 6 days at 37° C. with/without the indicated concentration of treatments.

Stimulation of monocytes with recombinant human CD28—$1.5\times10^6$ monocytes were plated at 24 well plate in RPMI medium with 100-100 U/ml IFN gamma (R&D system, Cat. No. 285-IF) in the presence of recombinant human CD28 at the indicated concentrations for 48 hrs. The generated cell populations were tested for the indicated phenotypes by FACS analysis of relevant markers (IDO, PD-L1 and PD-L2) and by analysis of secretion of characteristic cytokines (IL-6).

T cells stimulation with OKT3—$0.1\times10^6$ isolated CD3 T cells (from healthy donors) were stimulated with indicated amount of anti-CD3 clone OKT3 for 48-72 hr at 37° C. When stated recombinant human CD80-Fc (2 µg/mL, R&D system) was added in soluble form. Antibodies to CD28 or controls were added at the indicated concentration in soluble form.

CD86 blocking FACS—$0.5\times10^6$ HEK293 cells stably transfected with human CD28 were incubated with 5 µg/mL CD86-Fc (R&D systems, Cat. No. 141-B2) without or with anti CD28 antibodies (20 µg/mL) for 30 min in room temperature. Cells were washed and taken for secondary binding using anti-human heavy and light chains antibody conjugated to fluorophore at 1:5000 dilution for 20 min on ice.

Co-culture of SCC-25 cancer cell line with monocytes in trans-well based assay—$4\times10^4$ SCC-25 cells were plated on the bottom of 24 well plate with $1\times10^5$ monocytes placed on cell culture insert (Millipore, Cat. No. MCHT241148) with or without indicated treatments for 4 days in starvation media without serum.

Identification, cloning and sequencing of CD28 mRNA variants—Human PBMCs were stimulated with 0.5 ng/mL SEB (Sigma, Cat. No. S4881) for 7 days at 37° C. Human CD4 T cells were incubated with Phytohemagglutinin (2 µg/mL, Sigma, Cat. No. L8902) for 7 days at 37° C. Total RNA was extracted from cell pellets of activated and naïve immune cells with the RNeasy mini kit (Qiagen, Cat. No. 74106) using the Qiacube automated system (Qiagen). From each sample, 500 ng RNA was taken to RT reaction utilizing the High-Capacity cDNA Reverse Transcription Kit (Thermo Fisher Scientific, Cat. No. 4374966). Negative controls for RT reaction were tubes without RNA and another one without Reverse transcriptase. 1 µL of cDNA was taken for PCR using the following forward primer (CD28F) 5'-ATGCTGAGGCTGCTCTTGGCTCTCAAC-3' (SEQ ID NO: 38) and reverse primer (CD28R) 5'-TCAG-GAGCGATAGGCTGCGAAGTCGCG-3' (SEQ ID NO: 39). PCR products were loaded on 1% agarose gel. The PCR products were cut from the gel and were extracted using QIAquick Gel Extraction Kit. Sanger sequencing was performed where indicated using CD28F primer.

Detection of soluble human CD28 in cancer patients' plasma—20 frozen plasma samples in each of 10 different cancer indications and healthy donors were purchased from DxBiosamples (San Diego, Calif., USA). The plasma samples were diluted 1:20 and analyzed for soluble human CD28 by ELISA. Samples with high sCD28 were analyzed again in adequate dilutions.

Direct CD28 EIA—Unless discussed otherwise, Corning high binding plate or equivalent were used for screening. Each well was coated with 200-300 ng of human CD28-Ig chimera (R&D, Cat. No. 342-CD), mouse CD28-Ig chimera (R&D, Cat. No. 483-CD) or BSA conjugated dimeric peptide composed of CD28 stalk region amino acid sequence (Gly137-Pro152). Plates were blocked using 5% milk or 1% casein in PBS for 1 hr. at room temperature (RT). Plates were washed 3 times using PBST and incubated with investigated antibody following detection with goat anti mouse HRP Fc specific diluted 1:5000. Positive control is mouse anti human CD28 clone 28.2 or mice serum from immunized mice. Hybridoma supernatant cultures were screened undiluted.

Simulated sweeping of soluble CD28 from plasma of cancer patient. Antibodies or recombinant proteins were coated on tosyl-activated magnetic beads (Invitrogen, Cat. No. DY-14203) as described by manufacturer protocol. Beads were taken to exhibit the indicated amount of antibody and mixed with plasma sample of cancer patient. The mixture was incubated in a thermomixer for 2 hr, 1000 RPM at 37° C., followed by removal of the beads using a DynaMag magnet (Invitrogen, Cat. No. 12321D) and the samples were examined using CD28 specific ELISA.

Antibody sequencing. Antibodies were supplied to the Rapid Novor company for amino acid sequencing. Sequencing was performed using standard methods, which briefly include: LC-MS analysis performed after enzymatic digestion with six enzymes (pepsin, trypsin, chymotrypsin, elastase, Lys C and Asp N). Digestion was performed with disulfide reduction, and alkylation. LC-MS/MS analysis was performed using a Thermo-Fisher Q-exactive mass spectrometer. In both the heavy and light chains of each antibody 100% of amino acid residues were covered by at least 5 peptide scans, with significant supporting fragment ions. CDRs were determined using Chothia scheme.

Example 1: Human CD28 Undergoes Proteolytic Shedding During Chronic Stimulation

Figure 2:
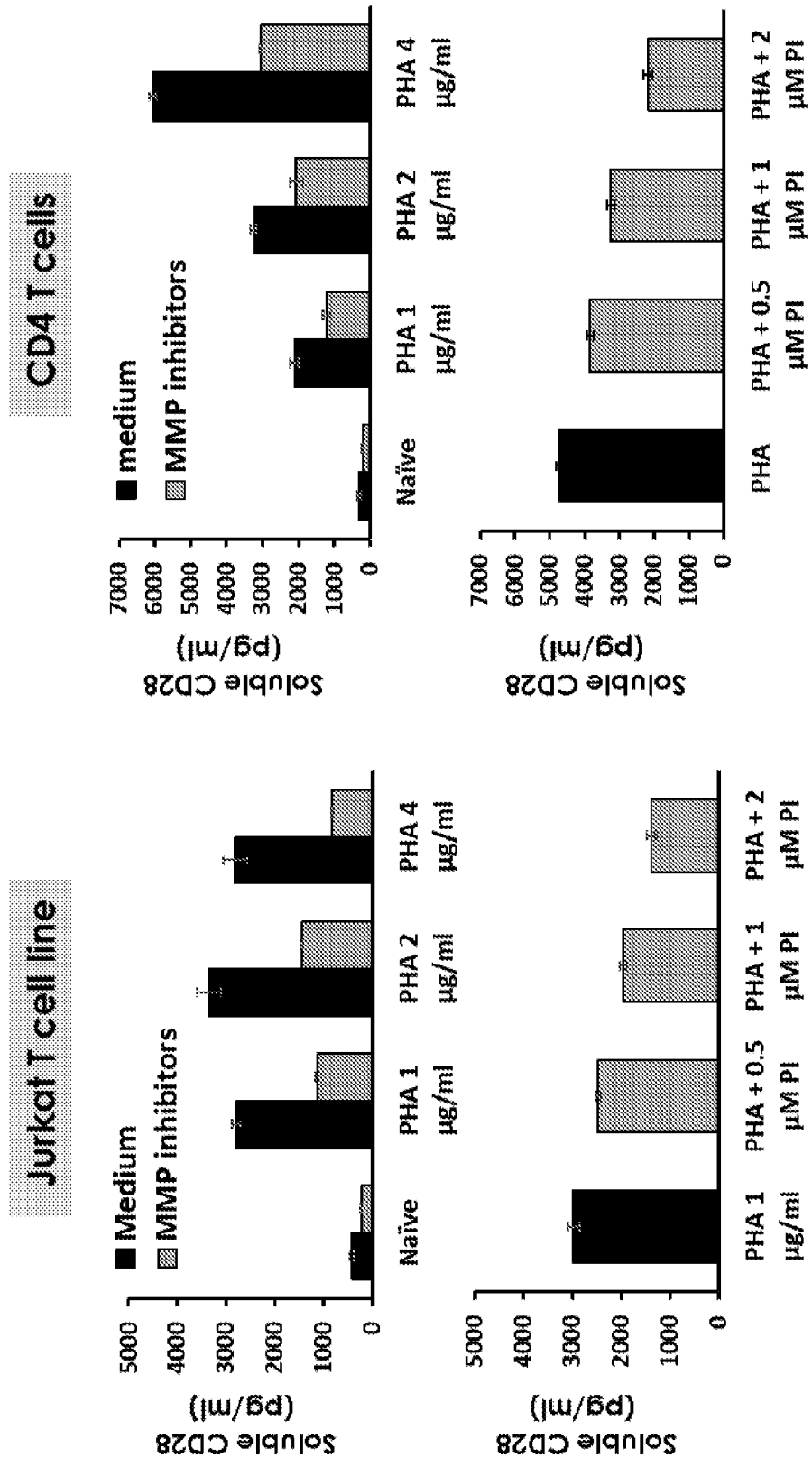
FIG. 2. Soluble CD28 is generated during stimulation of T cells by PHA and counteracted by addition of protease inhibitors. Bar charts of Jurkat cells (upper left) or isolated human CD4 T cells (upper right) stimulated with increasing concentrations of PHA (1-4 µg/mL, upper charts) in the presence of a protease inhibitor cocktail at a fixed concentration (2 µM). In another setup the PHA concentration was fixed to stimulate Jurkat T cells (1 µg/mL PHA, lower left) or human CD4 T cells (2 µg/mL PHA, lower right) and the concentration of the protease inhibitor cocktail was tittered (0.5-2 µM). The concentration of human CD28 in the supernatant was quantified with a standardized sandwich ELISA.

Soluble CD28 (sCD28) was detected by ELISA in the culture of chronically stimulated human PBMCs (FIG. 1). The phenomenon was evident regardless of the nature of the stimulant, artificial (SEB) or physiological (CMV), indicating the robustness of the phenomenon. The origin of soluble CD28 is from shedding of the membrane form, as treatment with TAPI-1 and GM6001 (broad MMP and ADAM17 inhibitors) diminish the amount of sCD28 in a dose dependent manner (FIG. 1). The cellular source of shed CD28 is T cells as can be seen in FIG. 2. Chronic stimulations with PHA, of either the Jurkat T cell line or human CD4 T cells from peripheral blood of healthy donors, results in the generation of sCD28 in a dose dependent manner (FIG. 2, upper charts). Treatment with TAPI-1 and GM6001 diminished the amount of sCD28 at each PHA concentration (FIG. 2, upper charts) and in a dose dependent manner at a fixed PHA concentration (FIG. 2. Lower charts).

Figure 3A:
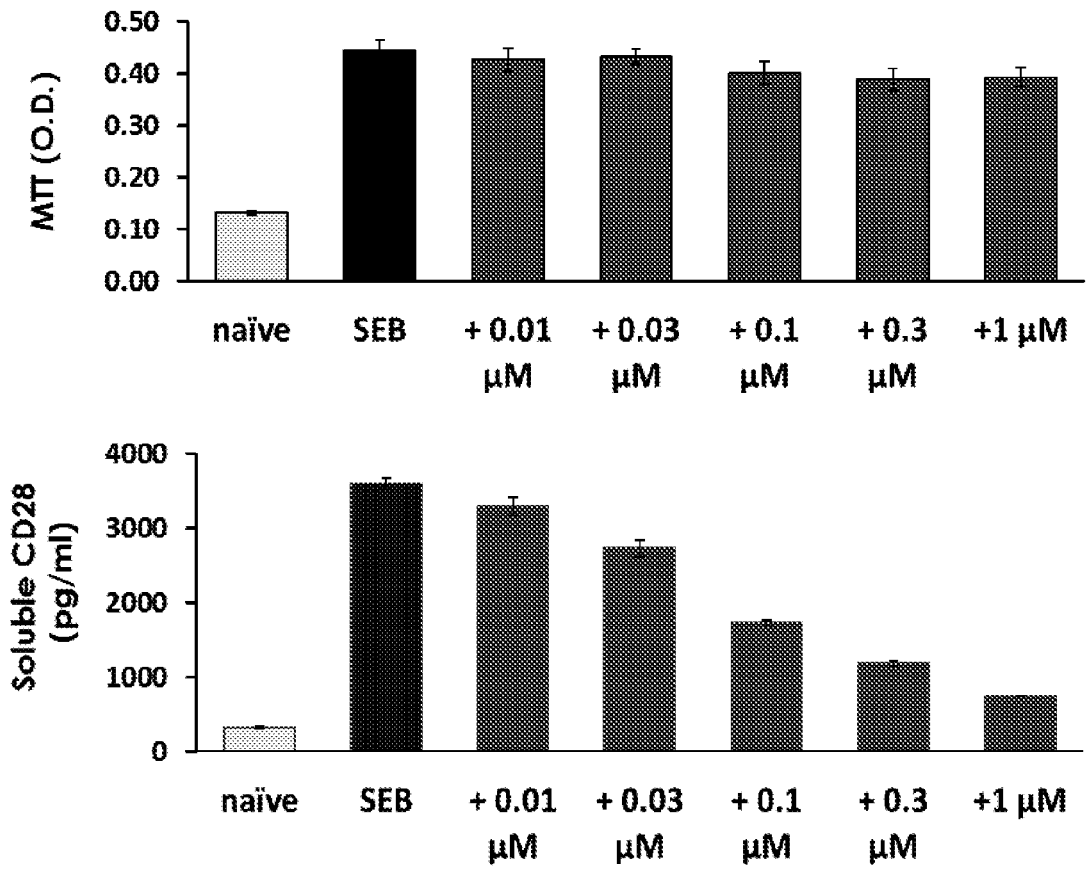
FIGS. 3A-B. Spcific ADAM-10 and ADAM-17 inhibitors eliminate the accumulation of soluble CD28 during human PBMCs activation by SEB while not hampering their viability. (3A-B) Bar charts of human PBMCs stimulated with SEB (1 ng/mL) in the presence of (3A) ADAM-10 specific inhibitor (GI254023X) and (3B) ADAM-17 specific inhibitor (TMI-1) at various concentrations (0.01-1 µM). The viability of the cells in the different treatments was evaluated using MTT assay (upper panel). The concentration of human CD28 (lower panel) in the supernatant was quantified with a standardized sandwich ELISA.
Figure 3B:
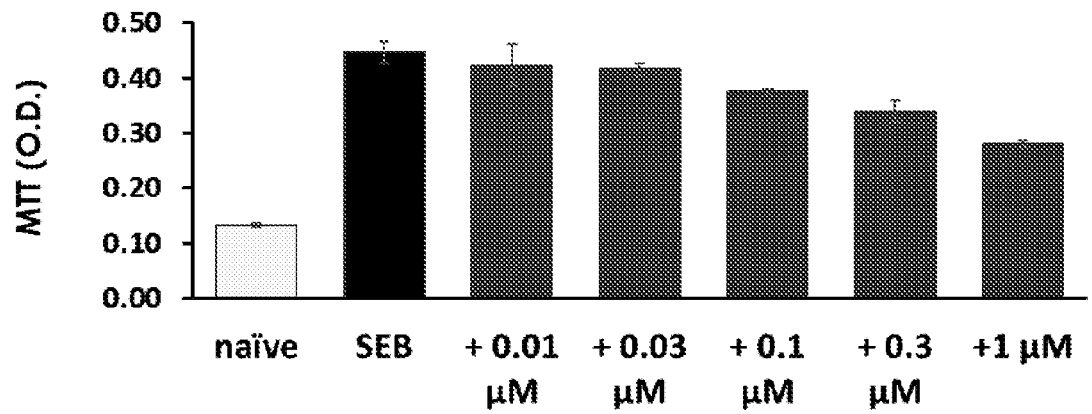
Figure 3B:
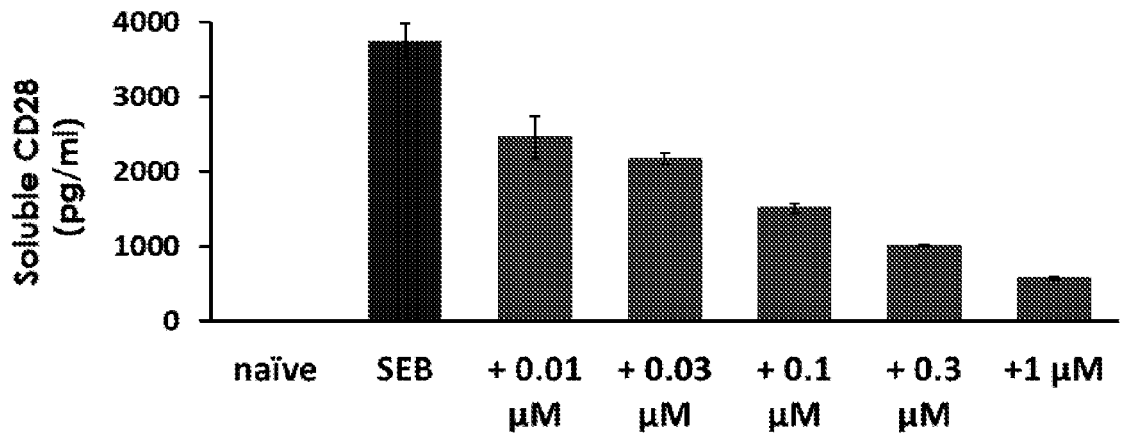

Treatment with GI254023X, a highly specific ADAM-10 inhibitor, resulted in almost complete inhibition of sCD28 release from activated immune cells and in a dose dependent manner (FIG. 3A, lower panel). Similar results were observed with the ADAM-17 specific inhibitor TMI-1 (FIG. 3B, lower panel). The viability of the immune cells was monitored by MTT assay, checking the metabolic activity of the cells in the culture. The results showed no significant difference between treatments with and without either ADAM inhibitor, implying that the low sCD28 levels are caused by blocking of protease activity and are not artifacts of cellular death caused by the protease inhibitor (FIG. 3A-B, upper panels).

Figure 4A:
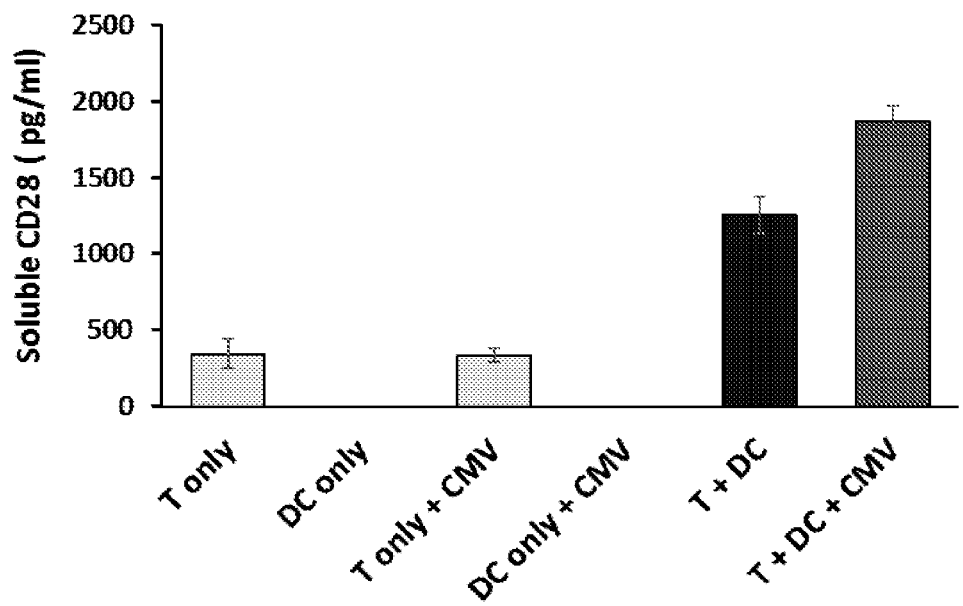
FIGS. 4A-D. Soluble CD28 is generated during PBMC stimulation. (4A) Bar chart of immature dendritic cells mixed in a 1:5 ratio with CD3 T cells from same donor without CMV (black bar) or with CMV peptides (dark grey bar). Control of each cell population alone or with CMV are in light grey bars. The concentration of human CD28 in the supernatant was quantified with a standardized sandwich ELISA. (4B-D) Bar charts of human PBMCs stimulated for 24 with (4B) CMV or (4C) SEB or (4D) SEB in the presence of ADAM-10 and ADAM-17 inhibitors, and then transferred to a clean culture. Measurements in FIG. 4D are 120 hours after cells were transferred.

The generation of sCD28 was validated also in more physiological systems. First, isolated autologous dendritic cells and CD4 T cells which mimic the physiologic stimulation of T cells by antigen presenting cells were utilized. Elevation of sCD28 was evident when mixing the two cell populations and became even more pronounced when CMV was added into the culture (FIG. 4A). This shows that the human CD28 protein experiences a proteolytic shedding process when chronic stimulation takes place.

Figure 4B:
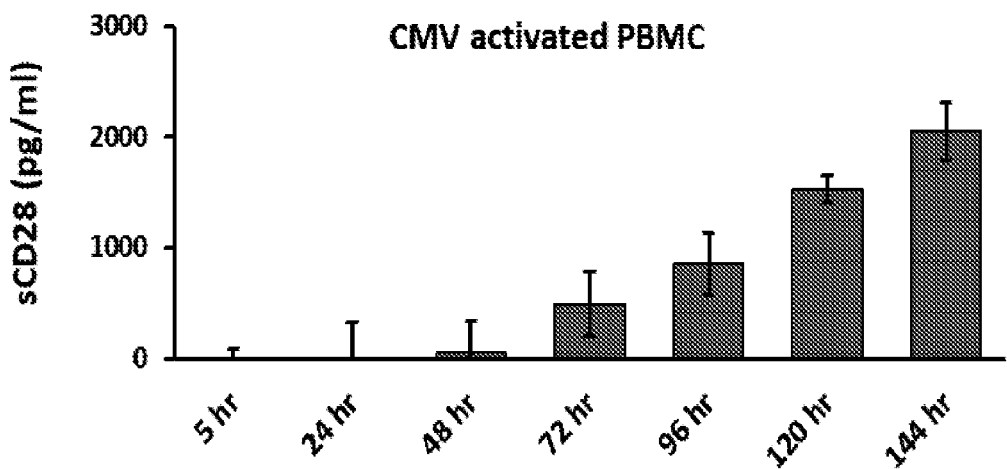
Figure 4C:
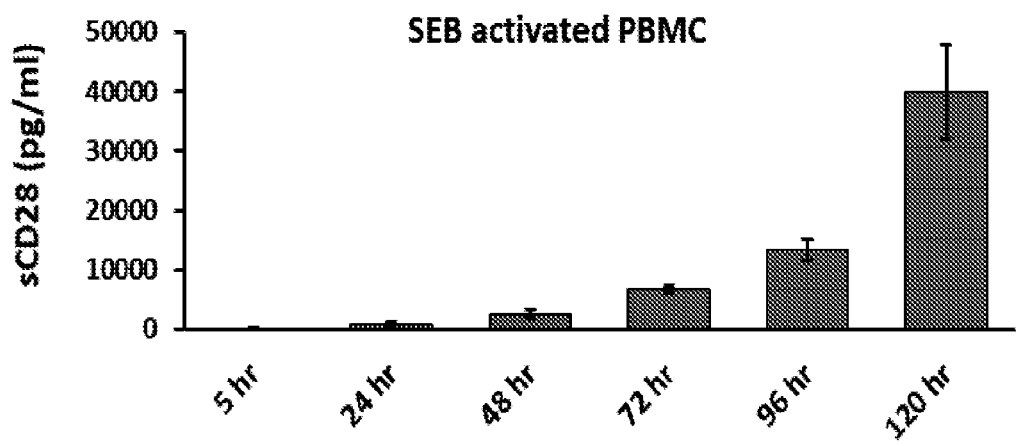
Figure 4D:
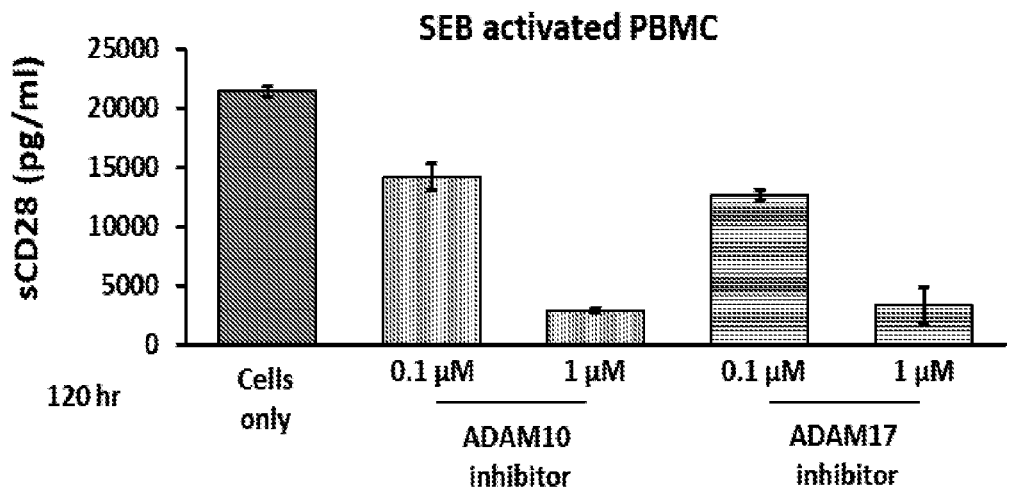

Next, human PBMCs were stimulated with CMV peptides (FIG. 4B), or SEB (FIG. 4C) for 24 hours. Afterwards, the cells were washed to remove the stimulant and plated again without any stimulation signal for various time periods. This was followed by examining for the presence of sCD28 in the culture media. The accumulation of sCD28 is clearly visible over time. Further, the accumulation is dependent of the activity of ADAM-10 and ADAM-17 as can be seen in FIG. 4D. Addition of specific inhibitors at different concentrations, after SEB stimulation, resulted in diminished amounts of sCD28 as quantified after 120 hours. This study can explain the existence of high amount of soluble CD28 in the blood of patients, as CD28 shedding takes place upon primary activation of T cells and does not necessarily need constant or repeated stimulations.

Figure 5:
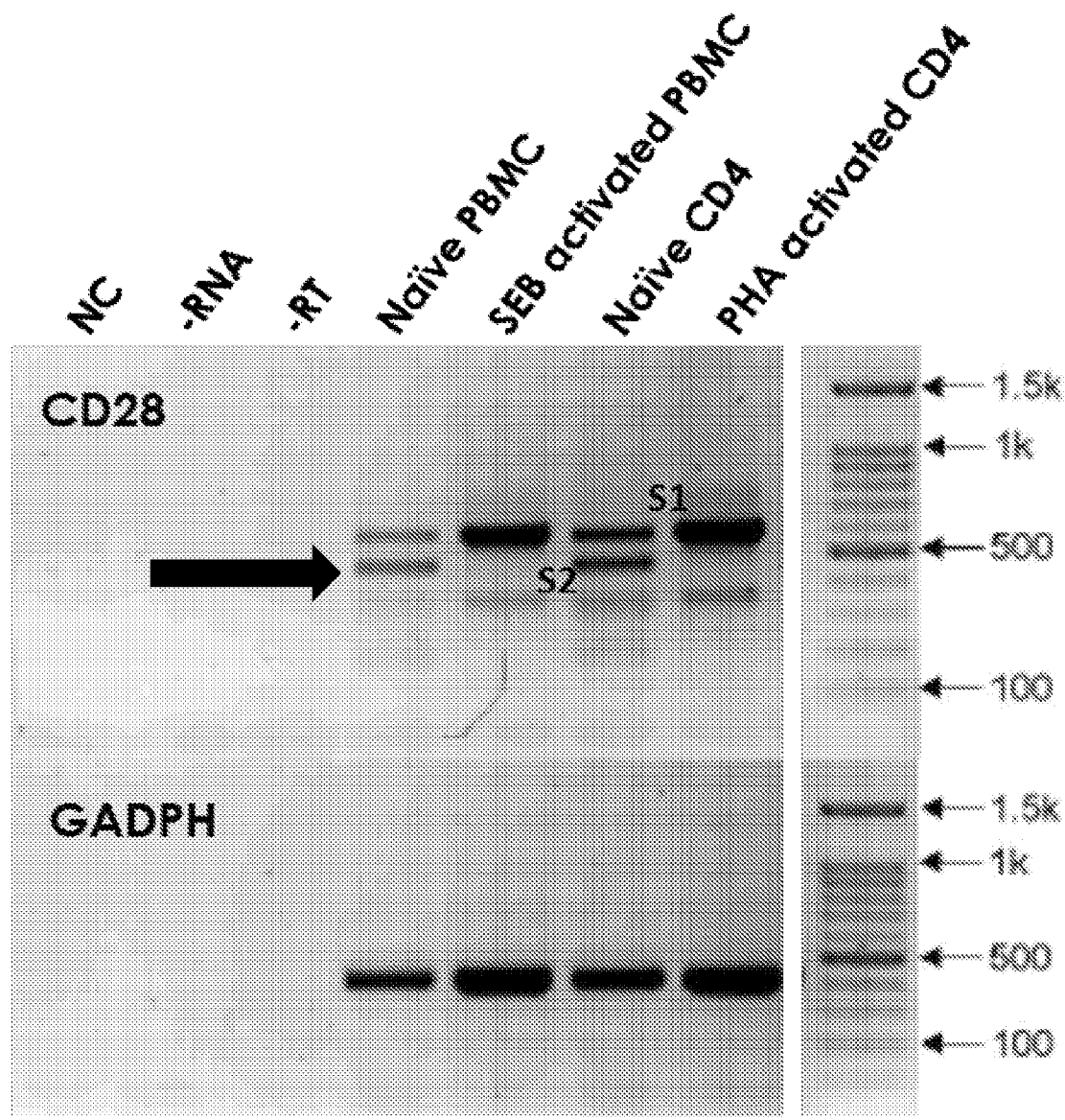
FIG. 5. The CD28 soluble splice variant is down-regulated in activated cells. Photos of gels showing the coding sequence of human CD28 amplified by PCR in non-stimulated PBMC (lane 4) and CD4 (lane 6), stimulated PBMCs (lane 5) and CD4 cells (lane 7). The amplified fragments were size-separated on a 1% agarose gel and visualized by ethidium bromide. GADPH cDNA was amplified as a control (lower panel). Bands taken for Sanger sequencing are marked by S1 (PHA activated CD4-650 bp) and S2 (naïve CD4-550 bp band)

A final piece of evidence that the source of sCD28 comes from proteolytic shedding was obtained by the observation that the known alternative spliced variant of CD28 is markedly down-regulated in activated lymphocytes (FIG. 5). Four CD28 mRNA products could be detected in non-stimulated samples, while only two were evident in activated cells. The uppermost band was confirmed by Sanger sequencing to correspond to the full-length mature CD28 which when translated is membrane bound and the second band (black arrow, ~500 bp) has previously been shown to be an alternatively spliced product which results in a secreted truncated protein. This band from naïve sequences was confirmed using Sanger sequencing to be the splice variant that lacks exon 3, and thus the transmembrane domain. SEB or PHA stimulation of PBMCs and T cells resulted in preferential expression of the full length CD28 mRNA, accompanied by suppression of the spliced transcript (FIG. 5, lanes 5 and 7). These results, taken together, demonstrate that the source of sCD28 from activated T cells is proteolytic shedding and not from alternative splicing at the gene level.

Example 2: Soluble Human CD28 has an Immune Suppressive Activity

Figure 6:
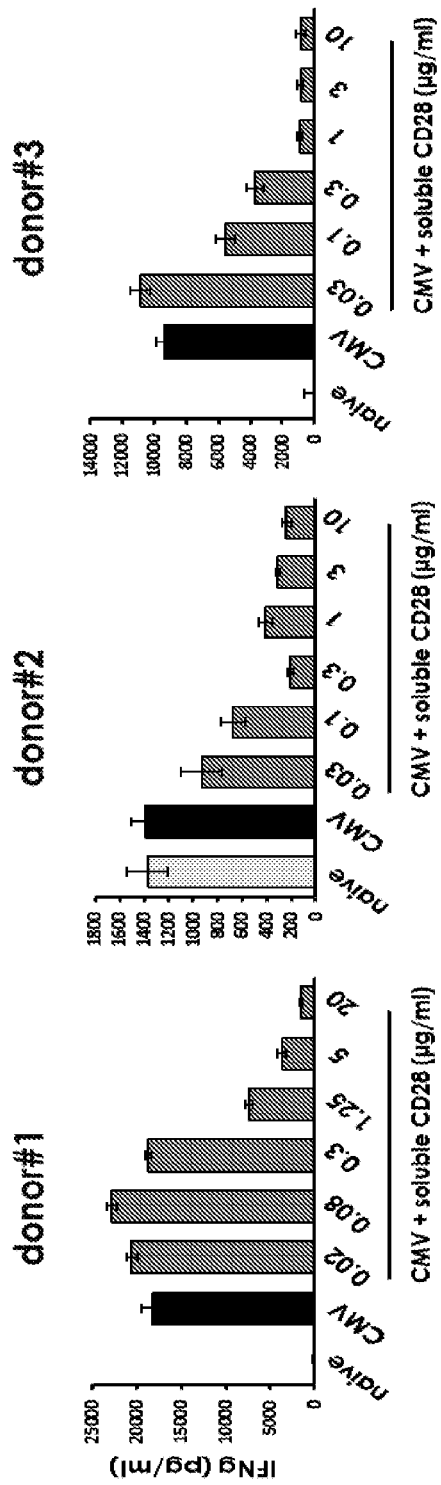
FIG. 6. Soluble CD28 inhibits effector cytokine secretion. Bar charts of human PBMCs stimulated with CMV (0.5 µg/mL) without (black bars) or with recombinant human CD28 at the indicated concentrations (grey bars). Naïve samples without CMV stimulation are indicated by light grey bars. The concentration of human IFN gamma in the supernatant was quantified with a standardized sandwich ELISA (Biolegend).

As can be seen in FIG. 1, lowering the levels of sCD28 using a protease inhibitor cocktail is directly correlated with elevation in T cell activation, as manifested by levels of secreted IFN gamma, suggesting that sCD28 has an immunosuppressive function. Increasing the concentration of protease inhibitor cocktail led to lower levels of sCD28 in the cells' media and these lower levels of sCD28 were inversely correlated with higher levels of secreted IFN gamma. To further explore immune suppression by sCD28, recombinant human CD28 lacking the transmembrane and cytoplasmic domains was added into cultures of human PBMCs stimulated with CMV. This resulted in a dose-dependent inhibition of IFN gamma secretion (FIG. 6). This immune suppression effect was observed in different human PBMCs donors, affirming the robustness of this signaling axis blocked by sCD28.

Figure 7:
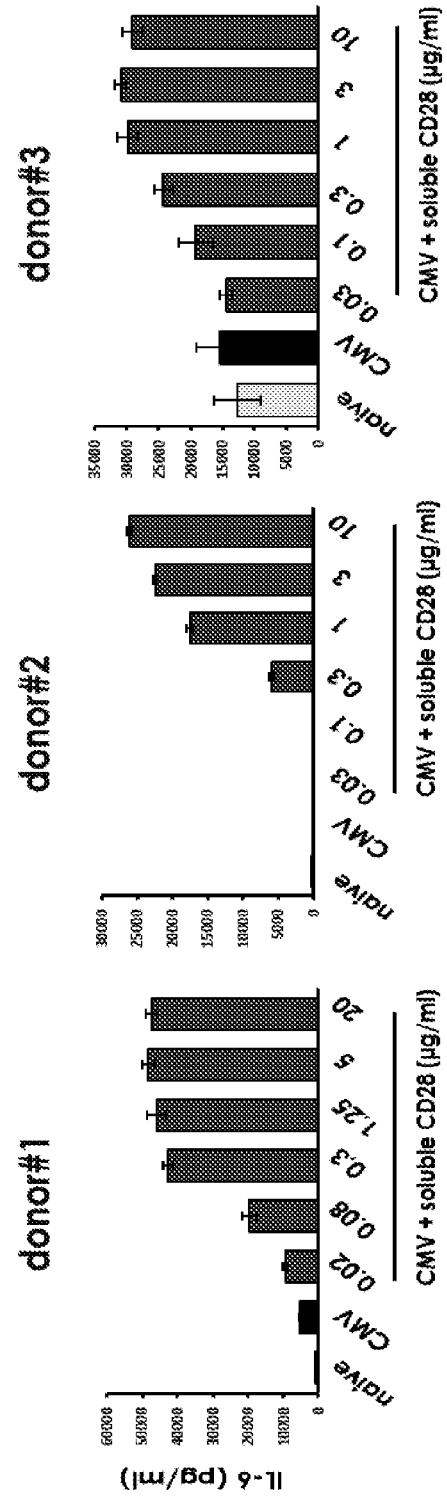
FIG. 7. Soluble CD28 increase IL-6 cytokine secretion. Bar charts of human PBMCs stimulated with CMV (0.5 µg/mL) without (black bars) or with recombinant human soluble CD28 at the indicated concentrations (grey bars). Naïve samples without CMV stimulation are indicated by light grey bars. The concentration of human IL-6 in the supernatant was quantified with a standardized sandwich ELISA (Biolegend).
Figure 8A:
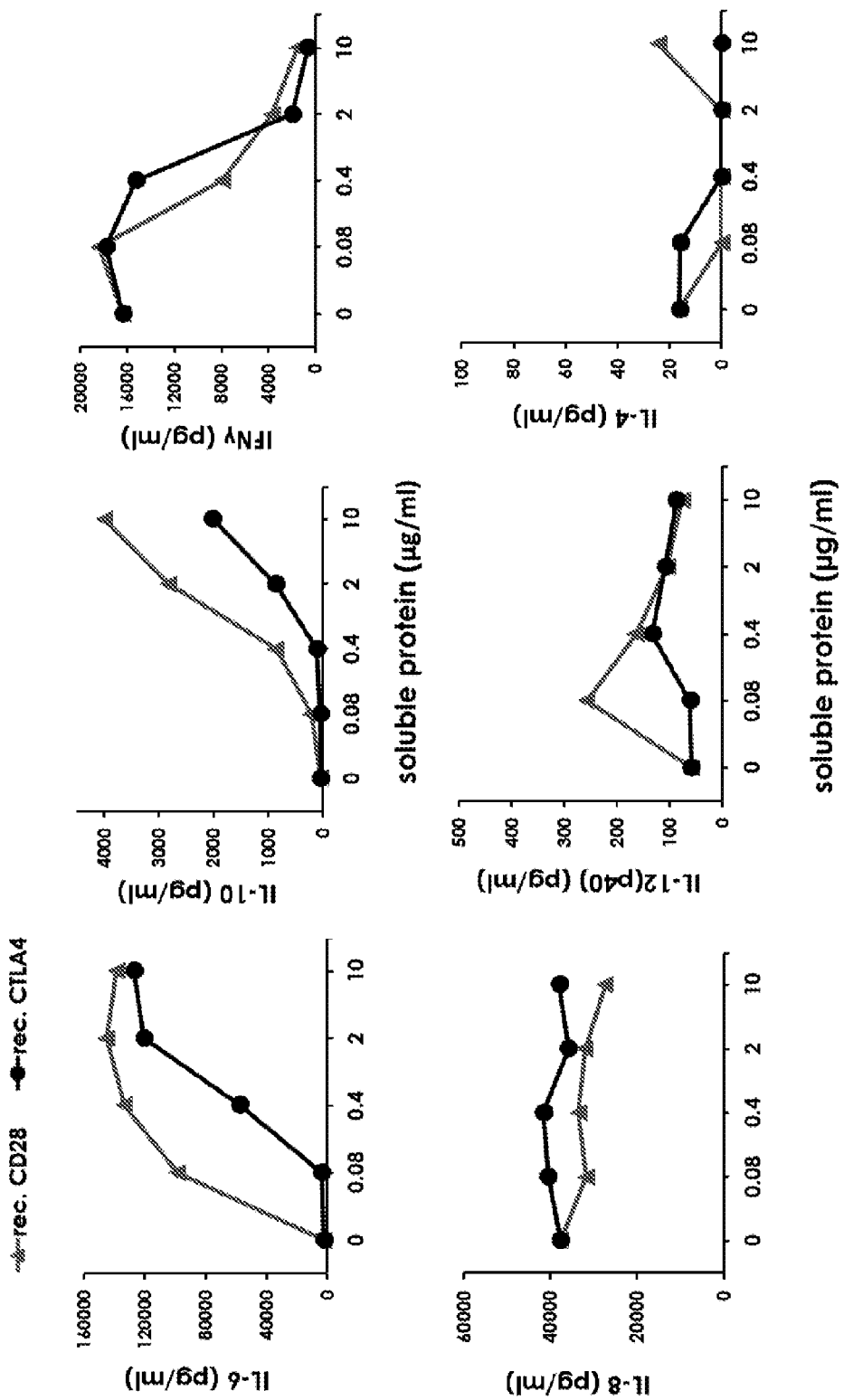
FIGS. 8A-E. (8A) Line graphs of human PBMCs stimulated with CMV (0.5 µg/mL) in the presence of recombinant human soluble CD28 (grey triangles) or recombinant human soluble CTLA-4 (black circles) at the indicated concentrations. The concentration of human L-6, IFN gamma and IL-4 in the supernatants were quantified with a standardized sandwich ELISA (Biolegend). The concentration of human IL-8, IL-12p(40) and IL-10 in the supernatants were quantified with a multiplex analysis using a Magpix system (Millipore). (8B) Bar graphs of cytokine secretion from autologous monocytes and CD3 MLR. Naïve samples without CMV stimulation are indicated by light grey bars. CMV alone or with IgG control are indicated with black bars. Increasing concentrations of sCD28 are indicated with dark grey bars. (8C) Line graphs of lymphocytes' clusters formation by human PBMCs stimulated with SEB in the presence of recombinant human soluble CD28 (grey circles) or with a control IgG (grey triangles). (8D) Bar graph of IDO secretion into culture as measured by Kynurenine ELISA kit from monocytes that were treated with and without recombinant human sCD28. (8E) Scatter plot of intracellular FACS for IDO in monocytes that were treated with and without recombinant human sCD28.

In parallel, an elevation of interleukin-6 secretion (FIGS. 7 and 8A) and interleukin-10 (FIG. 8A) was evident. These cytokines are reported to exhibit suppression of immune effector activity (IL-10) and skewing of the immune system toward a type-2 immune response which can support cancer proliferation and angiogenesis through STAT-3 signaling (IL-6). Additionally, a comparison with soluble CTLA-4 (mimicking Abatacept—a registered therapy for auto-immune disorders) was done and revealed an over-all similar impact on the immune system in terms of cytokine secretion profiles (FIG. 8A).

Figure 8B:
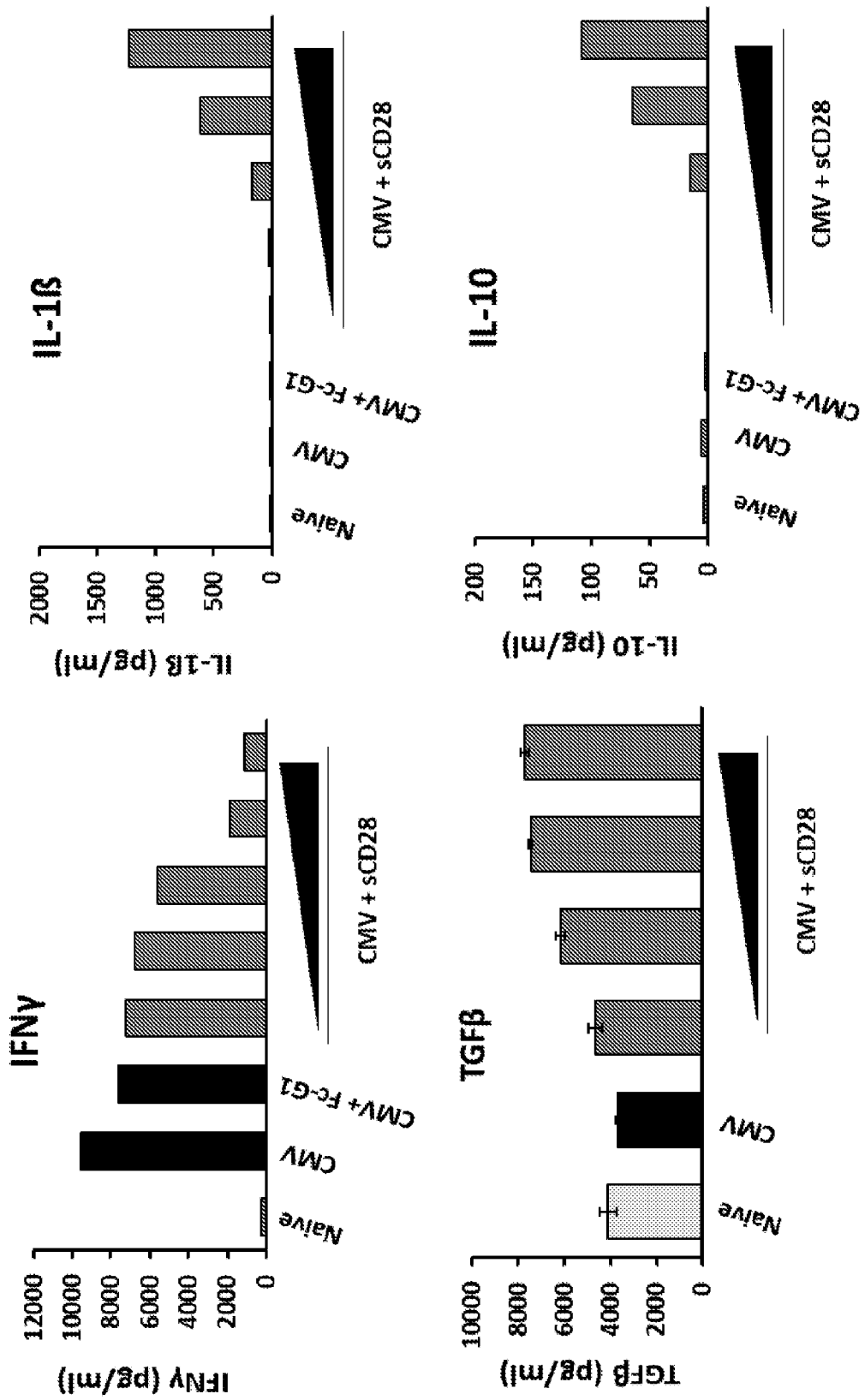
Figure 8C:
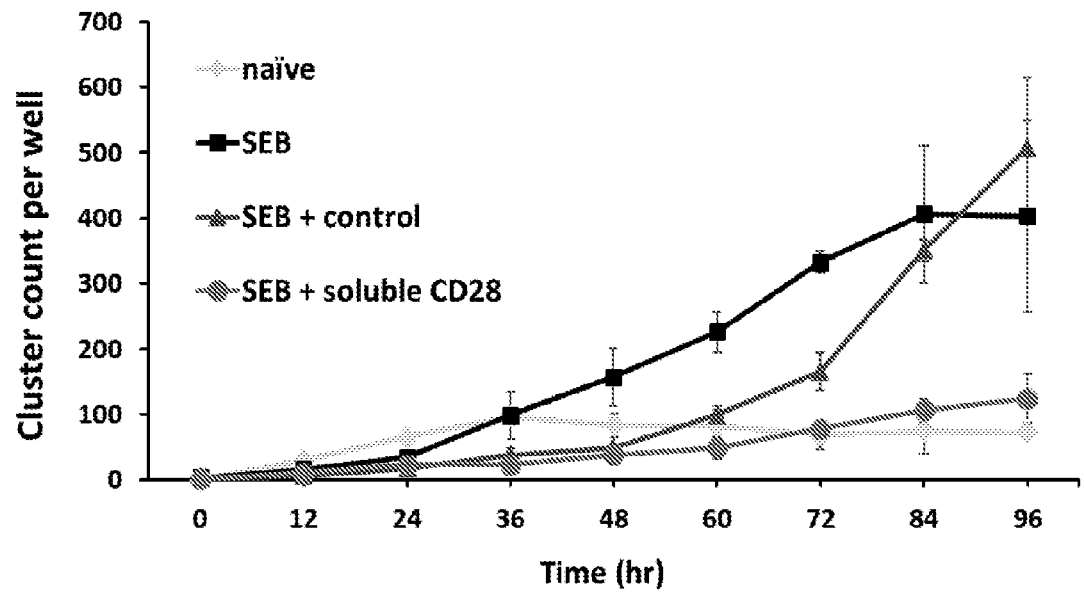

Next, human PBMCs were stimulated with SEB (1 ng/mL) without or in the presence of recombinant human CD28. Human IgG was used as control. Lymphocyte clustering, a hallmark of immune activation was monitored using the IncuCyte® S3 Live-Cell, with pictures taken every 12 hours. As can be seen in FIG. 8C, SEB had essentially no effect on the lymphocytes when the recombinant human sCD28 was present. It is well established that during in-vitro immune response antigen presenting cells (APC) cluster with one another and with other cell types, and clustering is essential for the antigen specific activation of resting lymphocytes. Soluble CD28 seems to diminish the amount and size of cluster formation during SEB immune response, meaning that it inhibits the first steps of T cells specific activation by APCs.

Figure 8D:
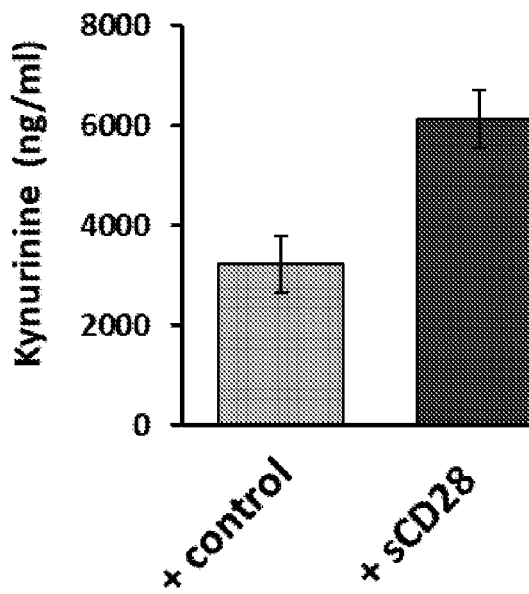
Figure 8E:
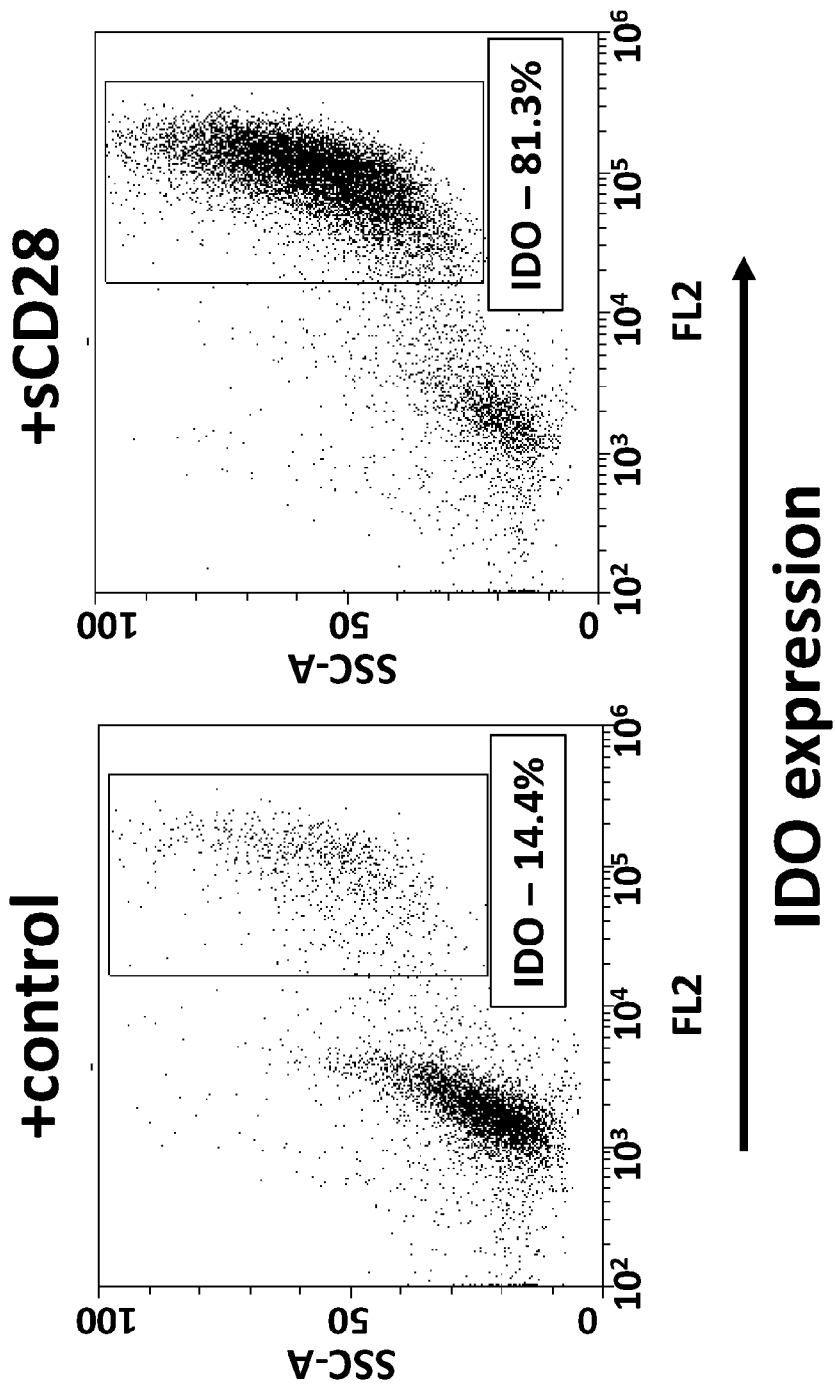

Similar results were observed when isolated autologous monocytes and CD3 T cells were cocultured in a mixed lymphocyte reaction (MLR). The mixed cells were stimulated for 5 days with CMV peptide (0.5 µg/mL) with and without increasing concentrations of recombinant human sCD28. Once again sCD28 was found to inhibit IFN gamma secretion, while simultaneously increasing the secretion of IL-1B, TGF beta and IL-10 (FIG. 8B).

sCD28 had a similar immunosuppressive effect on monocytes. The enzyme indoleamine 2,3-dioxygenase (IDO) has been implicated in immune modulation through its ability to catabolize the essential amino acid Tryptophan. It is expressed by different immune cells and also by many cancer cells. Tryptophan shortage inhibits T lymphocytes maturation and proliferation, while Kynurenine, the end product of tryptophan catabolism, is also known as immunosuppressive metabolite that promotes immune tolerance in various physiological and pathophysiological conditions. To test the effect of sCD28 on IDO, isolated human monocytes were stimulated for 48 hr with IFNγ (1000 U/mL) in the presence of control human IgG or with recombinant human CD28 (10 µg/mL). After incubation, the monocytes were stained intracellularly for human IDO (FIG. 8E). To facilitate intracellular staining the cells were fixed and permeabilized with BD Cytofix/Cytoperm Buffer Kit. The culture media of the different treatments were assessed for IDO activity using ImmuSmol specific Kynurenine ELISA kit (FIG. 8D). sCD28 strongly enhanced IDO expression in the monocytes.

Figure 9A:
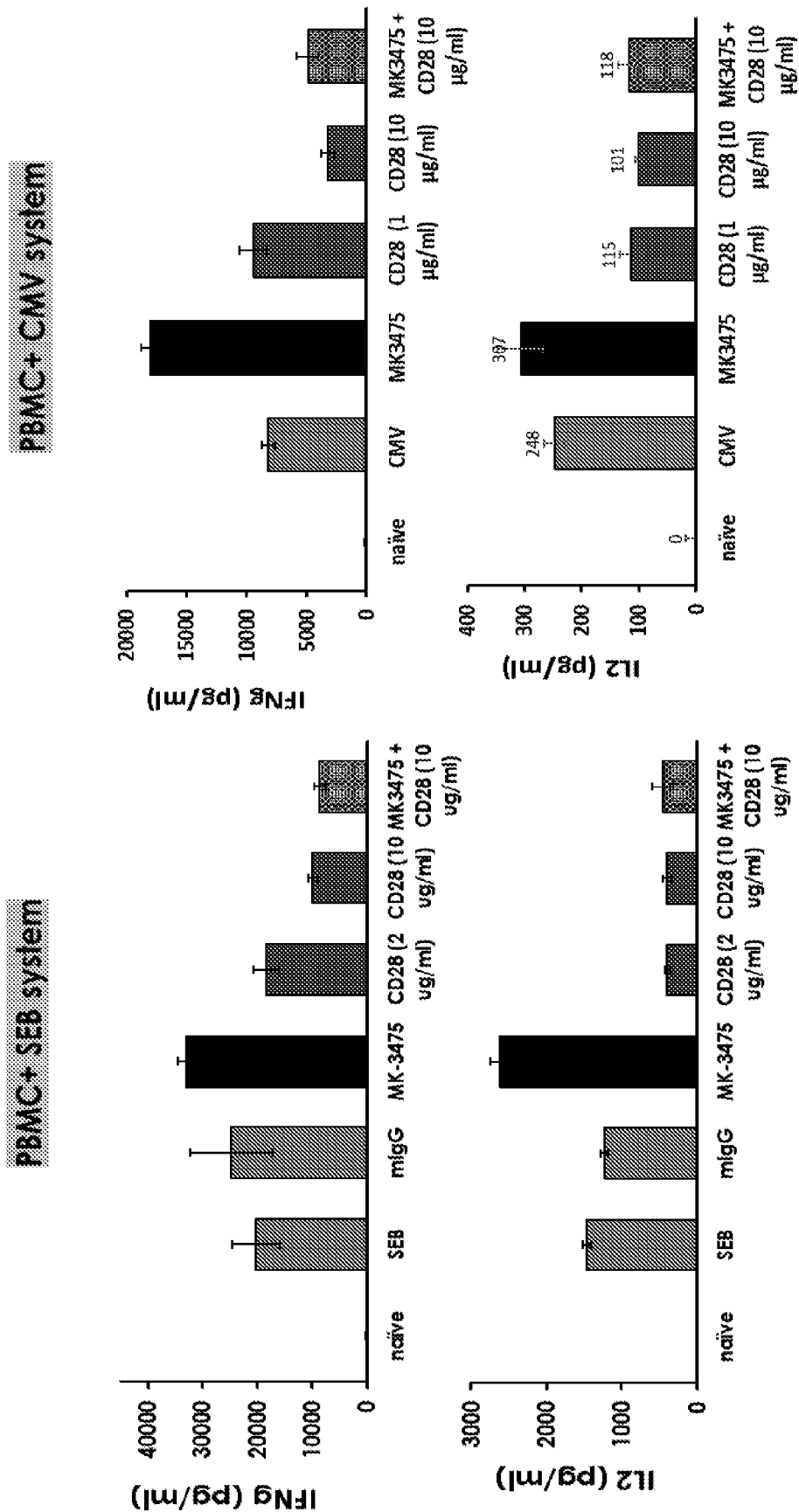
FIGS. 9A-C. Soluble CD28 impedes anti-PD1 treatment. (9A) Bar charts of human PBMCs stimulated for 3 days with SEB (200 ng/mL, left side charts) or CMV peptides (0.5 µg/mL, right side charts) in the presence of anti-PD1 (MK3475, 5 µg/mL, black bar) or recombinant human soluble CD28 (2 and 10 µg/mL, grey bars) or a combination of both (dotted bar). (9B) Bar charts of cytokine secretion from monocytes MLR setting, naïve-white bars, CMV alone-light gray bars, sCD28-black bars, MK-3475-dark grey, sCD28+MK-3475-plaid bars. The concentrations of human IFN gamma, TGF beta and IL-2 in the supernatants were quantified with standardized sandwich ELISAs (Biolegend). (9C) Histograms of surface PD-L1 (left) and PD-L2 (right) expression in monocytes after incubation with control and sCD28.

Further, it was surprisingly found that sCD28 is a potent inhibitor of anti-PD1 immuno-therapy. MK-3475 (Pembrolizumab or Keytruda, Merck) is an approved drug with unprecedent efficacy in multiple cancer indications. Its addition to PMBC culture increased proinflammatory cytokine secretion (IFN gamma and IL-2), however the presence of sCD28 abrogated completely this immune activation effect (FIG. 9A).

Figure 9B:
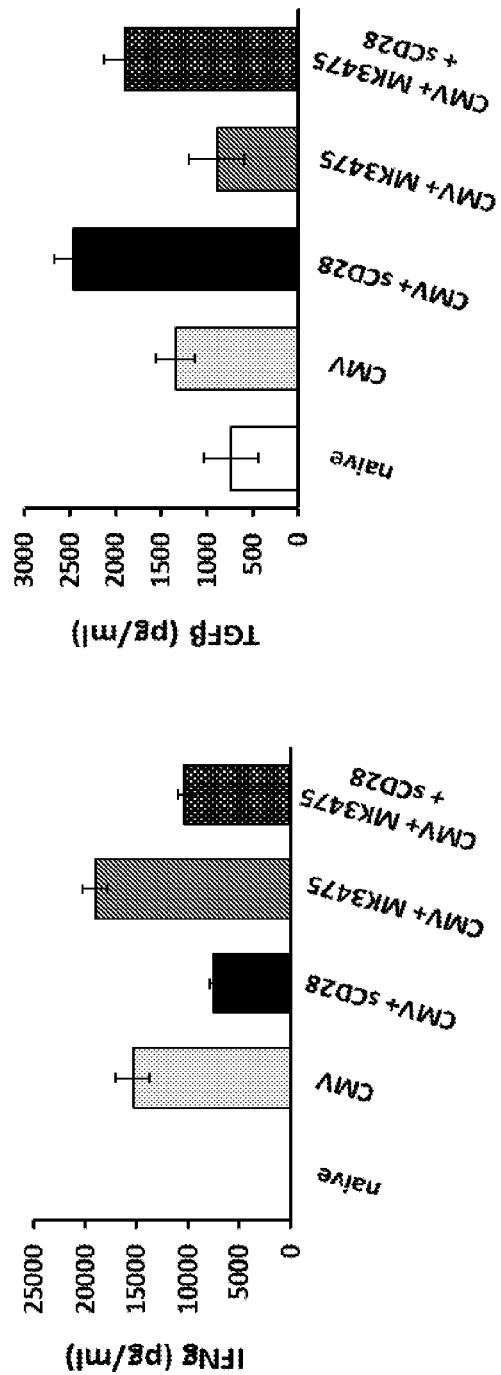

Similar results were again observed in an MLR setting. The MLR was run as before only with and without sCD28 and with and without an anti-PD1 antibody (MK3475, 5 µg/mL) (FIG. 9B). As expected, MK-3475 increased IFN gamma secretion and decreased TGF beta secretion. Notably, in the presence of sCD28 the effect of MK-3475 was significantly reduced.

Figure 9C:
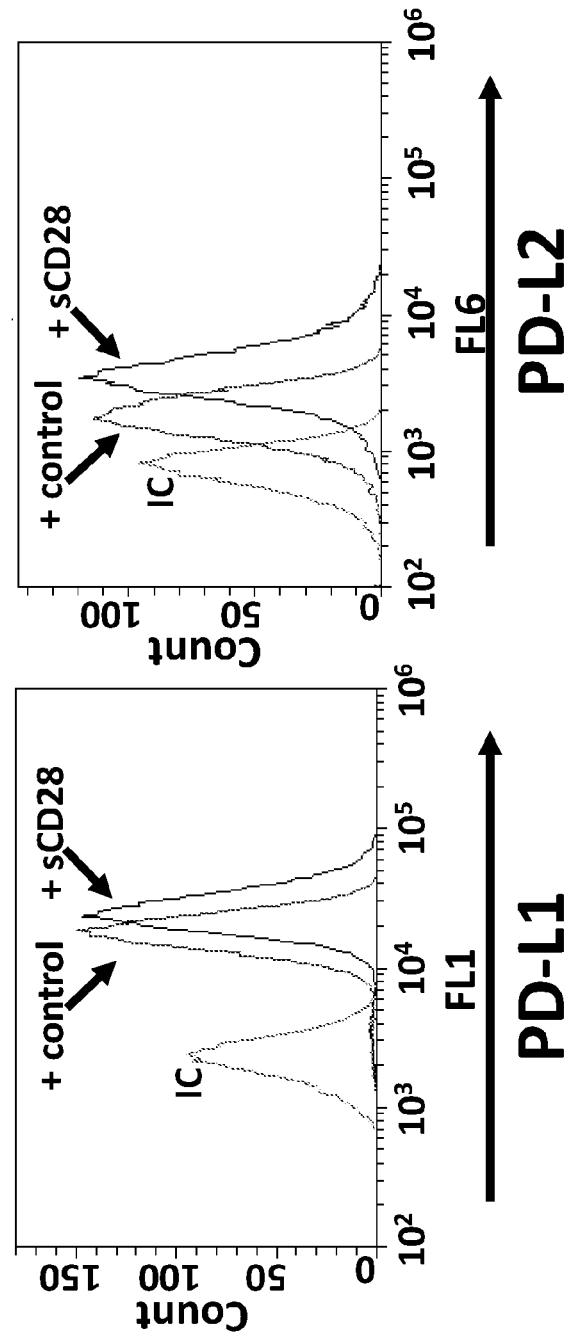

In order to elucidate the mechanism by which sCD28 inhibits the pro-activation effect of anti-PD-1 therapy, the expression of PD-1 ligands on immune cells in the presence of sCD28 was examined. Isolated human monocytes were stimulated for 48 hours with IFNγ (1000 U/mL) in the presence of control human IgG (10 µg/mL) or with recombinant human CD28 (10 µg/mL). After incubation the monocytes were stained for PD-L1 (FIG. 9C, left) and PD-L2 (FIG. 9C, right). Both ligands were upregulated on monocytes cultured with sCD28, suggesting one possible way in which sCD28 might circumvent the effects of anti-PD-1 immunotherapy.

Example 3: Soluble Human CD28 is Found in the Plasma of Cancer Patients

Figure 10A:
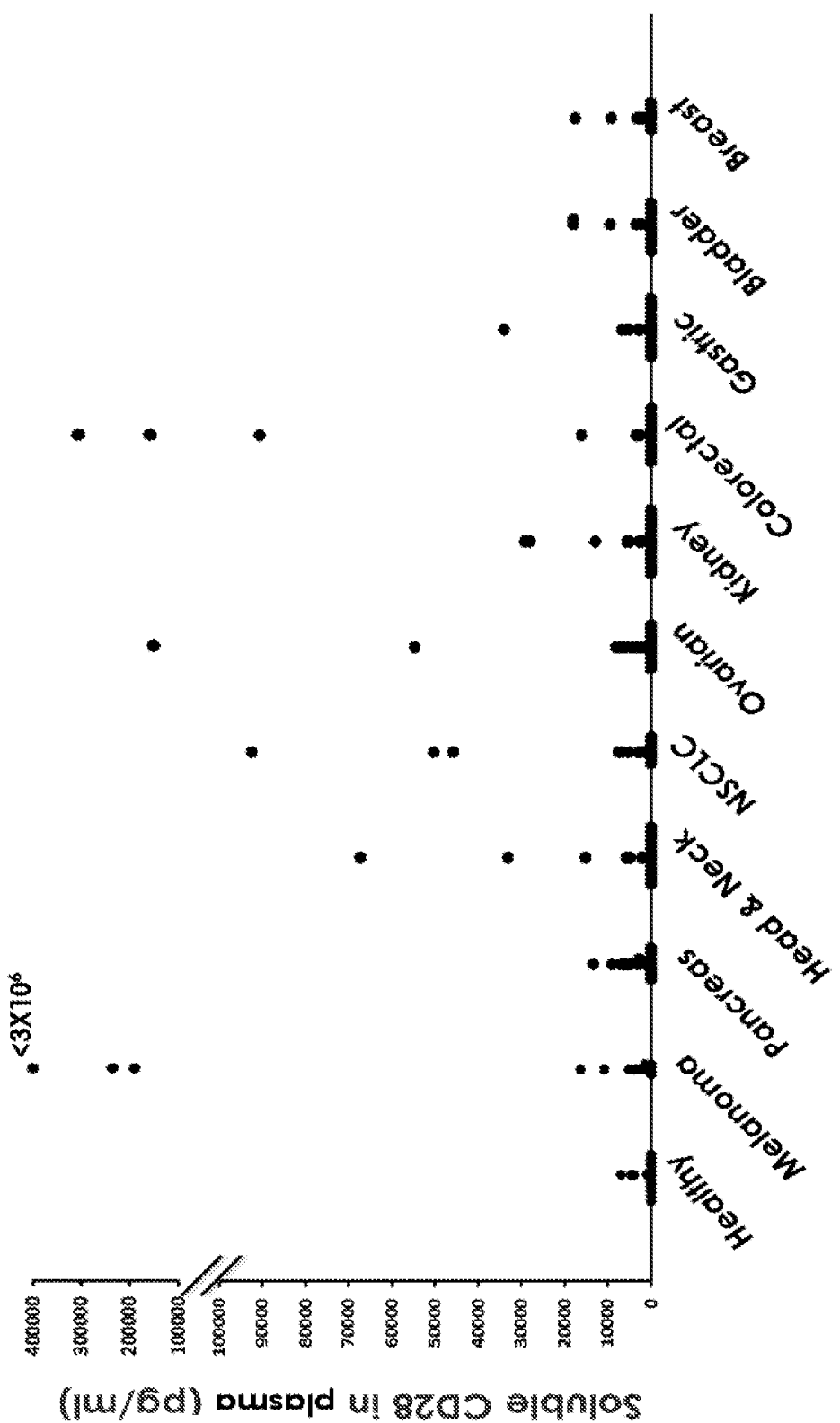
FIGS. 10A-D. Soluble CD28 in cancer patients. (10A) A dot plot showing 20 plasma samples in each of 10 cancer indications and healthy donors surveyed for the presence of soluble human CD28. Samples with high content of soluble CD28 were examined repeatedly with several dilution factors. The concentration of human CD28 in the supernatants was quantified with a standardized sandwich ELISA calibrated internally to accommodate readings from human plasma samples. (10B) Bar graph of ELISA detection of sCD28 from 20 melanoma patient samples using antibodies #1 and #3 of the invention and a commercially available CD28 ELISA kit. *-Measured amounts exceed 150 ng/ml. (10C) Bar charts of INF gamma secretion as measured by sandwich ELISA from SEB stimulated PBMC of cancer patients (a sarcoma patient-upper left, a kidney cancer patient-upper right, and two different head and neck cancer patients-lower) in the presence of sCD28, MK-3475 and a combination of the two. (10D) Bar charts of cancer cell SCC-25 viability and proliferation either alone, with IL-6, in coculture with monocytes or in coculture with monocytes and sCD28.
Figure 10B:
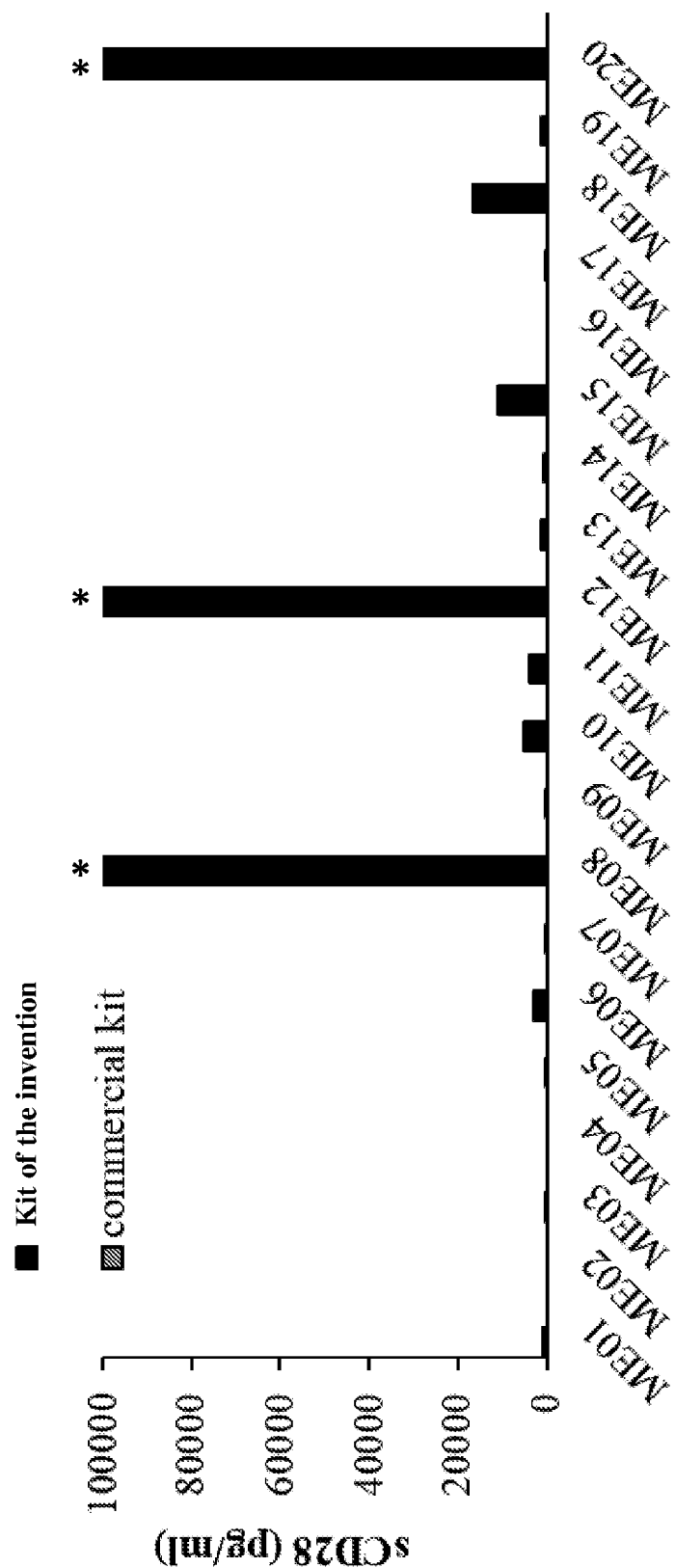

The levels of sCD28 in cancer has only been shown in a small number of breast cancer patients and were found to be only slightly elevated above what is observed in healthy individuals (Isitmangil, G., In vivo, 2016). Although the authors suggest that sCD28 might be used as a marker for breast cancer, no functional relationship is suggested. Now knowing that soluble CD28 may actually enhance cancer evasion of the immune system, a survey of 220 samples covering 10 different cancer indications and 20 samples from healthy donors was conducted. The survey found high sCD28 levels in several cancers, levels that were at times orders of magnitude higher than what was seen in healthy controls or even breast cancer patients (FIG. 10A). Indeed, when viewed in comparison to the sCD28 levels found in some melanoma, colorectal, ovarian, NSCLC and head and neck cancer patients, the levels in breast cancer patients appear to be comparable to healthy individuals. This survey was conducted using antibodies #1 and #3 of the invention. It was surprising that such high levels had not been previously reported in any study known to the inventors. Therefore, 20 melanoma patient samples were tested by sandwich ELISA using the antibodies of the invention (antibody #3 for capture and antibody #1 for detection) and also a commercially available CD28 kit available from R&D Systems (cat #DY342). Although the antibodies of the invention detected very high levels of sCD28 in three of the samples and lower levels in another fourteen, the commercially available kit did not detect sCD28 in any of the samples (FIG. 10B). Similar results were found with the commercially available CD28 ELISA kit BMS290, available from Thermo Fischer Scientific, which had been used in the study of Isitmangil et al. regarding breast cancer. The inability of commercially available kits to detect sCD28 shed from human cells may explain why high sCD28 in cancer patients was not a known phenomenon until now.

Figure 10C:
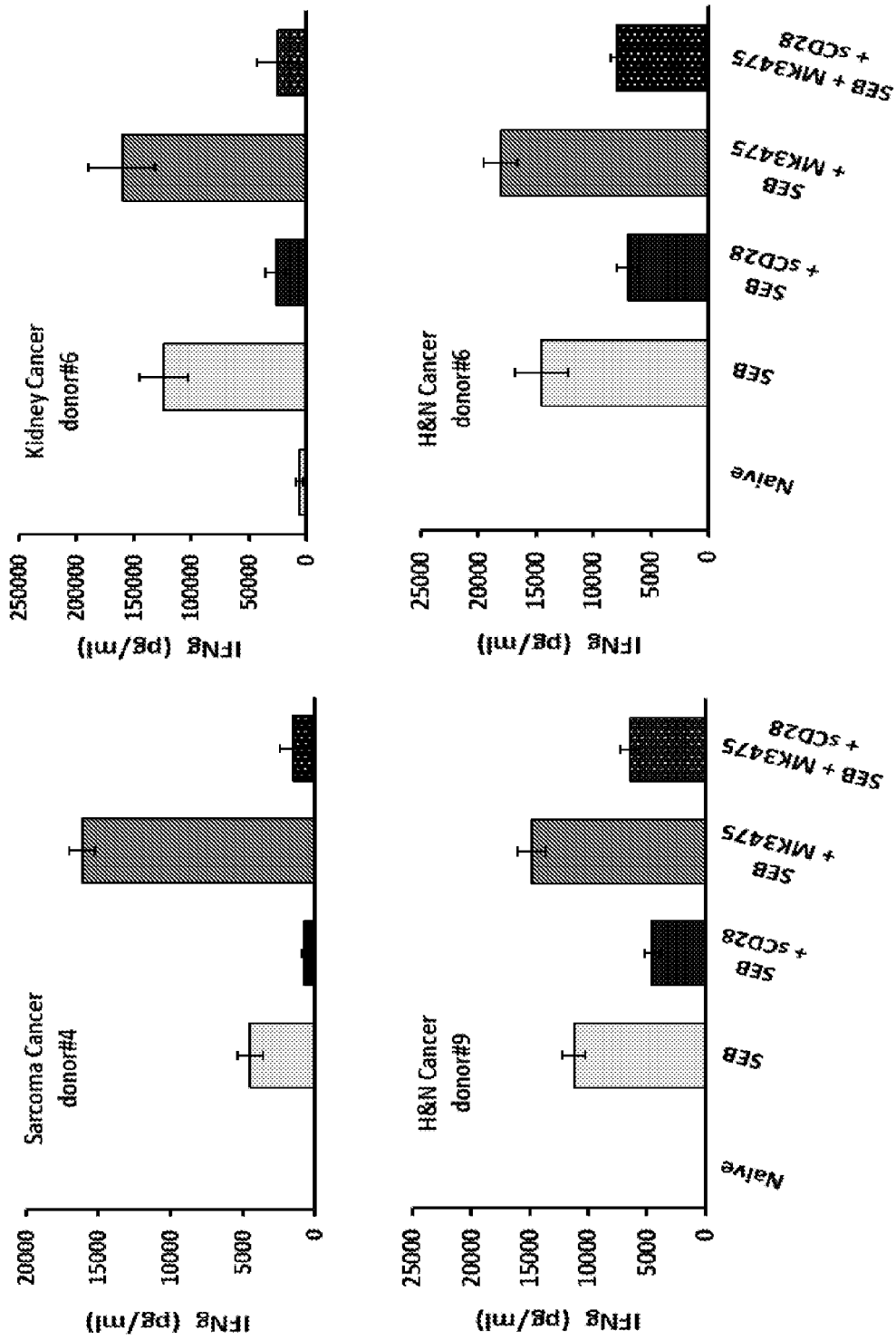

In order to further elucidate the role of sCD28 in cancer PBMCs were isolated from cancer patients with different indications. The cells were stimulated with SEB (5 ng/mL) for 3 days either, alone, with MK-3475, with recombinant human sCD28, or with a combination of both molecules. The concentration of human IFN gamma in the supernatant from the cells from all donors was greatly reduced in the presence of sCD28, even when MK-3475 was present (FIG. 10C). Indeed, sCD28 rendered the effect of MK-3475 nonexistent.

Figure 10D:
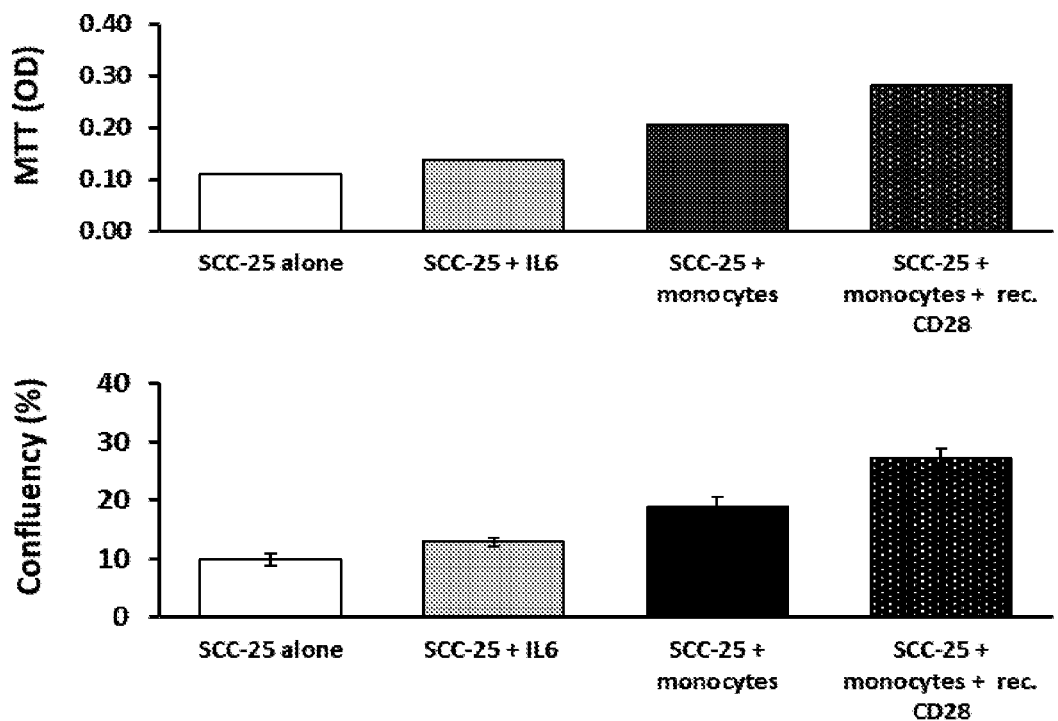

Next, cells of the head and neck cancer cell line SCC-25 were incubated either alone or with monocytes in a transwell assay. SCC-25 cells grown alone were administered IL-6 as a positive control, and indeed cell proliferation, as measured by MTT (FIG. 10D, upper) and as measured by % confluency (FIG. 10D, lower), was increased. Growing the cancer cells in the presence of the monocytes also increased proliferation, but by far the greatest increase was observed when the coculture included sCD28. This data further supports that sCD28 has a pro-cancer effect.

Example 4: sCD28 Inhibits CD80-Fc Efficacy

Figure 11A:
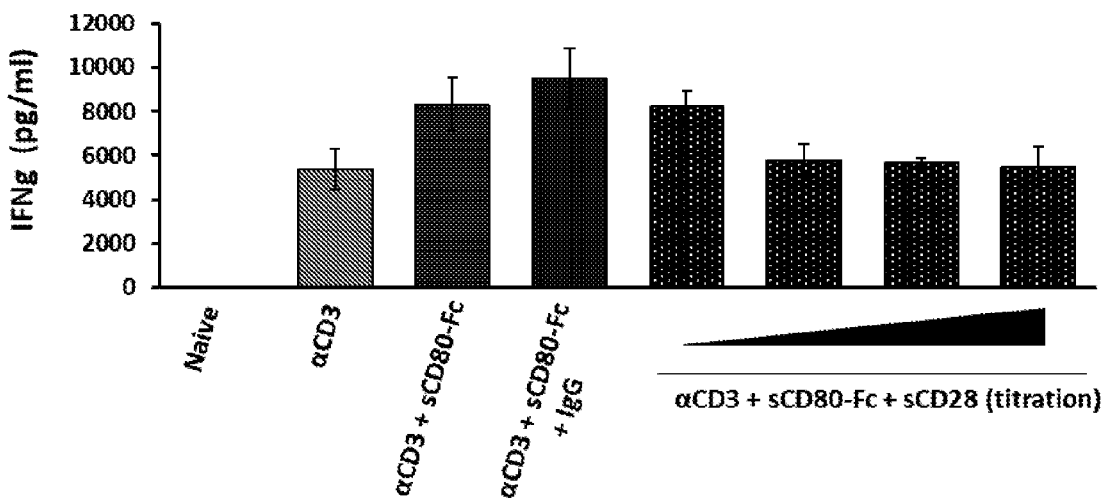
FIGS. 11A-B. (11A) Bar graphs of IFN gamma secretion from isolated CD3 T cells stimulated with anti-CD3 in the presence of constant CD80-Fc levels and titration of soluble CD28. (11B) Isolated PBMC stimulated with CMV in the presence of constant sCD28 levels and CD80-Fc titrations.
Figure 11B:
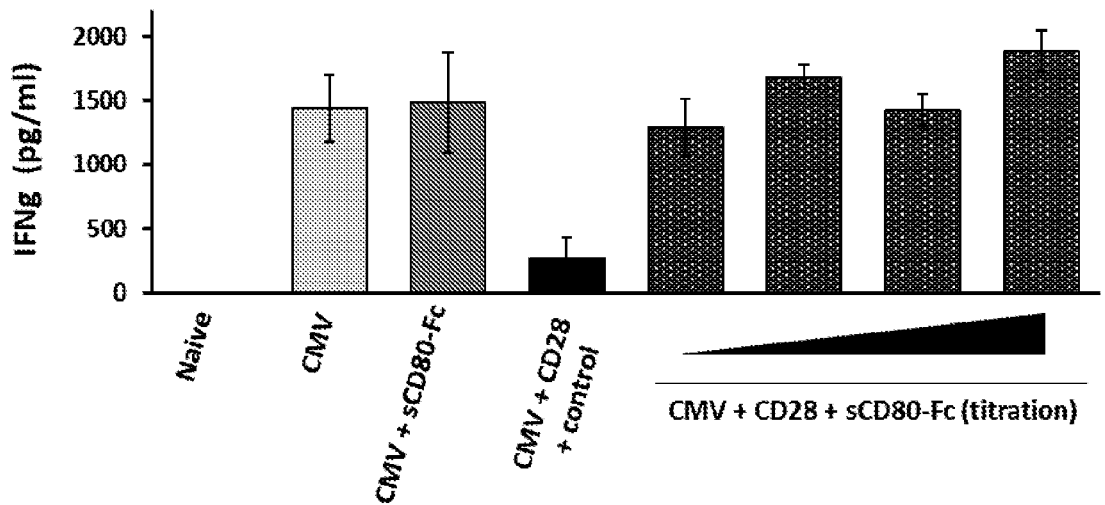

CD80 is one of the two main ligands for mCD28 along with CD86. The extracellular domain of CD80 fused to an Fc moiety has been used as an immune stimulatory molecule and is under investigation as a cancer therapy. In order to examine the effect of sCD28 on CD80-Fc efficacy, isolated CD3 human T cells were stimulated with plate bound anti-CD3 antibody (OKT3, 2 µg/mL) in the presence of 2 µg/mL soluble recombinant human CD80-Fc. As expected, CD80-Fc increased IFN gamma secretion. Addition of sCD28 however, counteracted the secondary activation effect of the CD80-Fc (FIG. 11A). Similarly, when isolated PBMCs were stimulated with CMV peptide for 3 days and then incubated with sCD28 an increased amount of CD80-Fc was required to generate the expected immune response (FIG. 11B).

Example 5: Effect of sCD28 on Cancer In Vivo

Figure 12A:
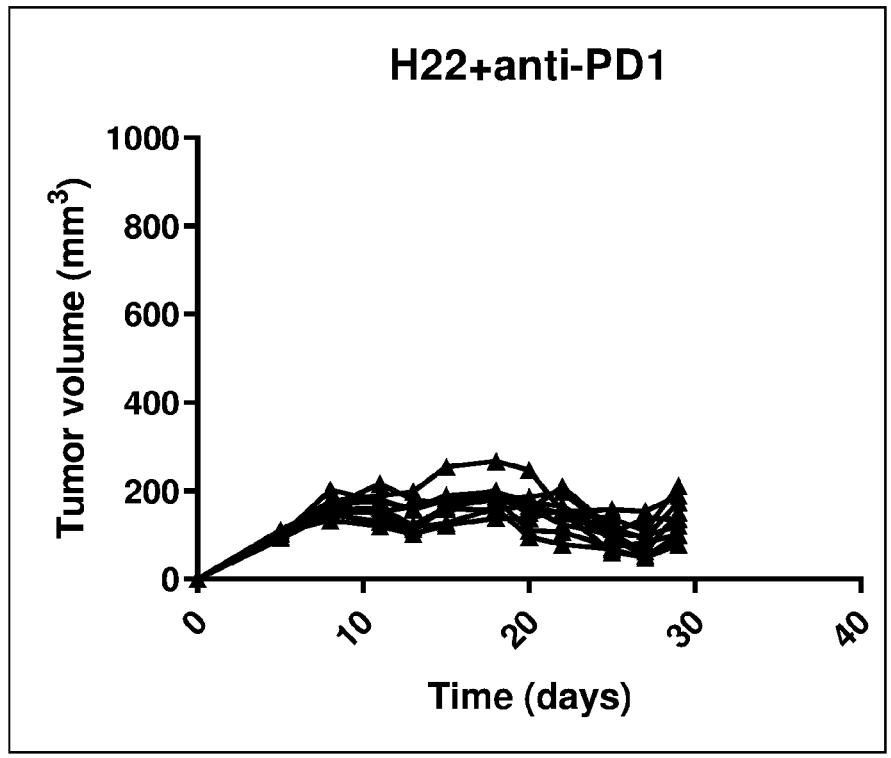
FIGS. 12A-B. (12A-B) Line graphs of tumor volume of inoculated H22 cells in an immunocompetent mouse treated with anti-PD-1 antibody without (12A) and with (12B) the administration of recombinant mouse CD28.
Figure 12B:
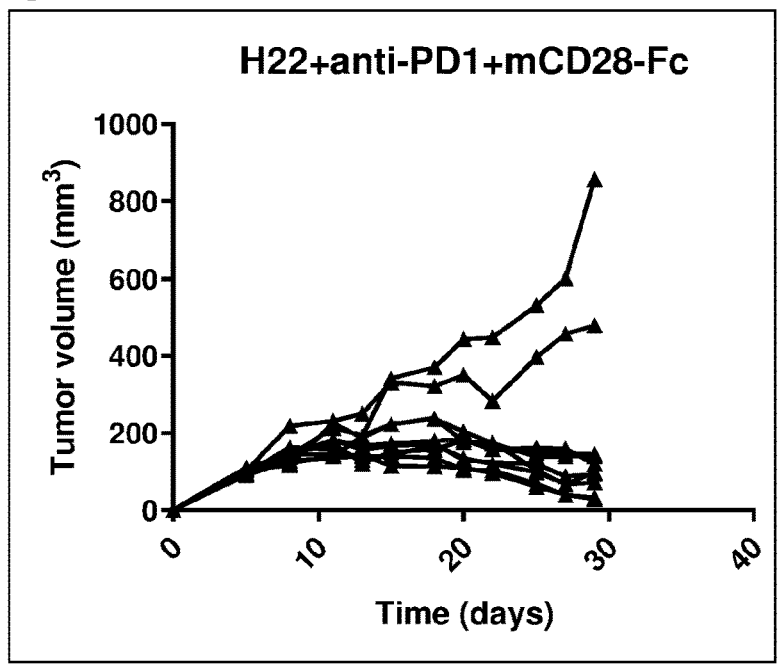

Because mice do not cleave mCD28, the effect of sCD28 cannot be easily examined in a mouse model. The closest option is to administer recombinant sCD28 to mice to mimic a situation of elevated sCD28 levels. This was investigated in a H22 syngeneic mouse model. Balb/c fully immunocompetent mice received an allograft of H22 hepatocellular carcinoma cells. The cells grew even in the fully immunocompetent mice, and addition of anti-PD-1 therapy nearly completely abolished tumor growth (FIG. 12A). When recombinant human sCD28 was added the effect of the anti-PD-1 therapy was nearly completely abrogated in two of the mice (FIG. 12B). This suggests that in some subjects, increased sCD28 levels can have a highly deleterious effect on cancer progression.

Example 6: Characterization of Antibody-Based Agents that Eliminate the Immune-Suppressing Effects of sCD28 (Anti-Cleavage)

The finding that human CD28 undergoes a proteolytic process by ADAM10 and ADAM17 prompted the inspection of its polypeptide sequence for candidate regions showing potential susceptibility for proteolytic shedding. Studies have suggested that ADAM10 and ADAM17 prefer leucine, valine and aromatic residues at the P1' site. The most attractive sequence region in human CD28 is the stalk section, ranging from Histidine 134 to Proline 152 (SEQ ID 10: HVKGKHLCPSPLFPGPSKP), connecting the globular IgV domain to the transmembrane region. This region holds 3 total leucine and valine residues, as well as a phenylalanine residue and is predicted to be devoid of any secondary structure elements that might hinder access of the proteases. Notably, the stalk region also contains Cysteine 141 that forms the inter-disulfide bond that facilitates the homo-dimerization of CD28. With the aim of generating an antibody or antibody fragments that specifically bind the CD28 stalk region and potentially block access of different proteases to shed CD28 while avoiding any compromising of CD28 oligomeric structure and function, CD1 mice were immunized with a dimeric peptide mimicking the CD28 stalk region. The peptide sequence used for immunization was SEQ ID: 40, GKHLCPSPLFPGPSKPK, the C-terminal Lysine was added in order to have a free amino group to allow KLH or BSA conjugation using hydrazide chemistry. The conjugations were performed between the hydrazide-terminated CD28 peptide and S-4FB modified BSA, which generates free aldehydes for site-specific conjugation. Dimerization was confirmed by running the peptide on a non-denaturing gel.

Six mice were immunized with the BSA conjugated peptides. Mice tail-bleed serums were routinely checked by ELISA for binding to the target antigen, recombinant human CD28 (rhCD28), and to the KLH-conjugated mixed peptides.

High throughput screening platforms were used for an initial clone screen for binding to antigen target in ELISA. About 2000 hybridomas were generated and screened in the initial EIA against rhCD28, using culture supernatants as the primary antibody and developed with HRP-conjugated goat-anti-mouse IgG (gamma) and TMB. 20 clones were attained all of which were IgG2a antibodies and further expanded for purification and isotyping. An ELISA assays confirm that all 20 IgGs have various levels of significant binding to recombinant soluble CD28 (Table 1).

TABLE 1

Anti-cleavage antibodies

| Clone Number | Clone name | CD28 ELISA | Irrelevant control | Isotype |
| --- | --- | --- | --- | --- |
| M1 | 1E09 | 3.45 | 0.13 | IgG2a |
| M2 | 1G02 | 3.48 | 0.1 | IgG2a |
| M3 | 2A07 | 3.04 | 0.05 | IgG2a |
| M4 | 2C10 | 3.23 | 0.05 | IgG2a |
| M5 | 2F11 | 3.46 | 0.11 | IgG2a |
| M6 | 3G01 | 3.41 | 0.12 | IgG2a |
| M7 | 3H09 | 3.31 | 0.12 | IgG2a |
| M8 | 4C02 | 3.43 | 0.13 | IgG2a |
| M9 | 4G07 | 3.36 | 0.06 | IgG2a |
| M10 | 5C07 | 3.34 | 0.07 | IgG2a |
| M11 | 5D03 | 3.22 | 0.06 | IgG2a |
| M12 | 5E02 | 3.34 | 0.1 | IgG2a |
| M13 | 6C07 | 3.38 | 0.05 | IgG2a |
| M14 | 7C08 | 3.46 | 0.11 | IgG2a |
| M15 | 6B08 | 3.45 | 0.08 | IgG2a |
| M16 | 8C05 | 3.41 | 0.08 | IgG2a |
| M17 | 8E09 | 3.39 | 0.05 | IgG2a |
| M18 | 9B09 | 3.31 | 0.08 | IgG2a |
| M19 | 9B06 | 3.18 | 0.05 | IgG2a |
| M20 | 10C04 | 3.06 | 0.15 | IgG2a |
| Negative Control | | 0.07 | 0.07 | |
| positive sera | | 3.36 | 3.16 | |

Figure 13A:
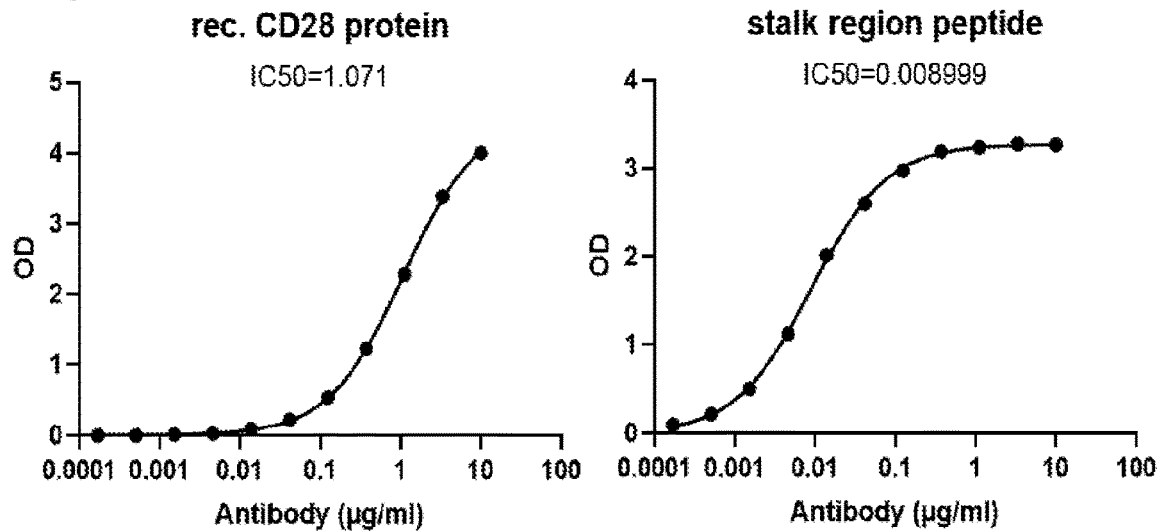
FIGS. 13A-C. (13A) Line graphs showing antigen binding by serial dilution of clone M9 to the BSA conjugated CD28 stalk region dimeric peptide (right) and recombinant human CD28 protein (left). Antigens were immobilized on maxisorp ELISA plates. A dilution series of clone M9 was preformed and detection of bound antibody was done with donkey anti mouse IgG (H&L)-HRP and development with TMB. (13B) Bar graphs of ELISA detection of recombinant human sCD28 (left) and sCD28 shed from human PBMCs activated with SEB (right). The ELISA used antibody #3 as a positive control (2 µg/mL, grey bars), irrelevant antibody M39 as a negative control (10 µg/mL, dark grey bars) and anti-cleavage antibody M9 (10 µg/mL, black bar). Detection of recombinant CD28 or shedded CD28 was done by using ELISA kit detection antibody conjugated to HRP (0.5 µg/mL). (13C) Line graph of results of ELISA assay on increasing concentrations recombinant human CD28-Fc, recombinant human CD28a, recombinant mouse CD28 and dimeric human CD28 stalk region peptide for commercially available MAB342, clone 37407.
Figure 13B:
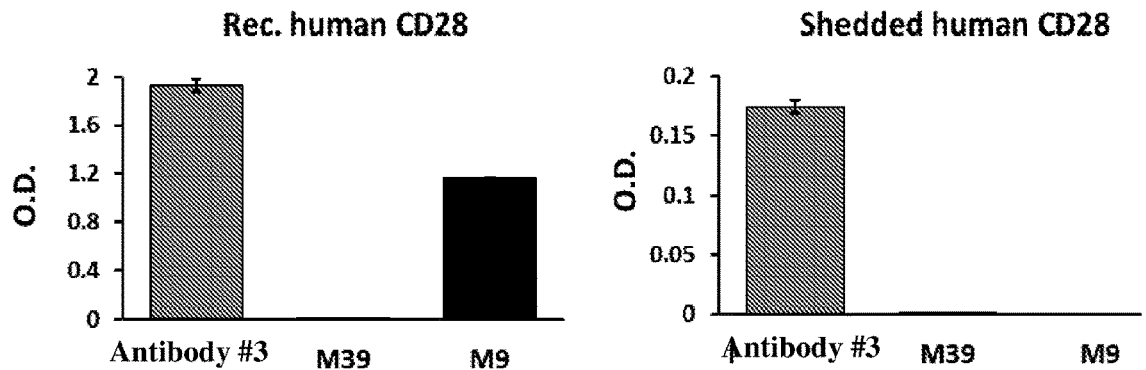

The three highest binding clones were all sequenced and found to be the same antibody (hereafter referred to as clone M9) and so experiments were continued with this antibody. The sequence of the M9 antibody can be found hereinabove. Serial dilution of antibody M9 was used to confirm its specific binding to recombinant human sCD28 and to the stalk region peptide (FIG. 13A). Interestingly, while the antibody was able to detect recombinant human sCD28 it was not able to detect sCD28 actually shed from immune cells (FIG. 13B). This strongly suggests that the antibody binds at the cleavage site, and the deisotope to which it binds is incomplete in the cleaved form. Direct inhibition of cleavage is checked by mixing rhCD28 with either ADAM10 or ADAM17 in the presence and absence of antibody M9. The resulting rhCD28 peptide is sequenced by mass spectrometry to determine if cleavage occurs.

Figure 13C:
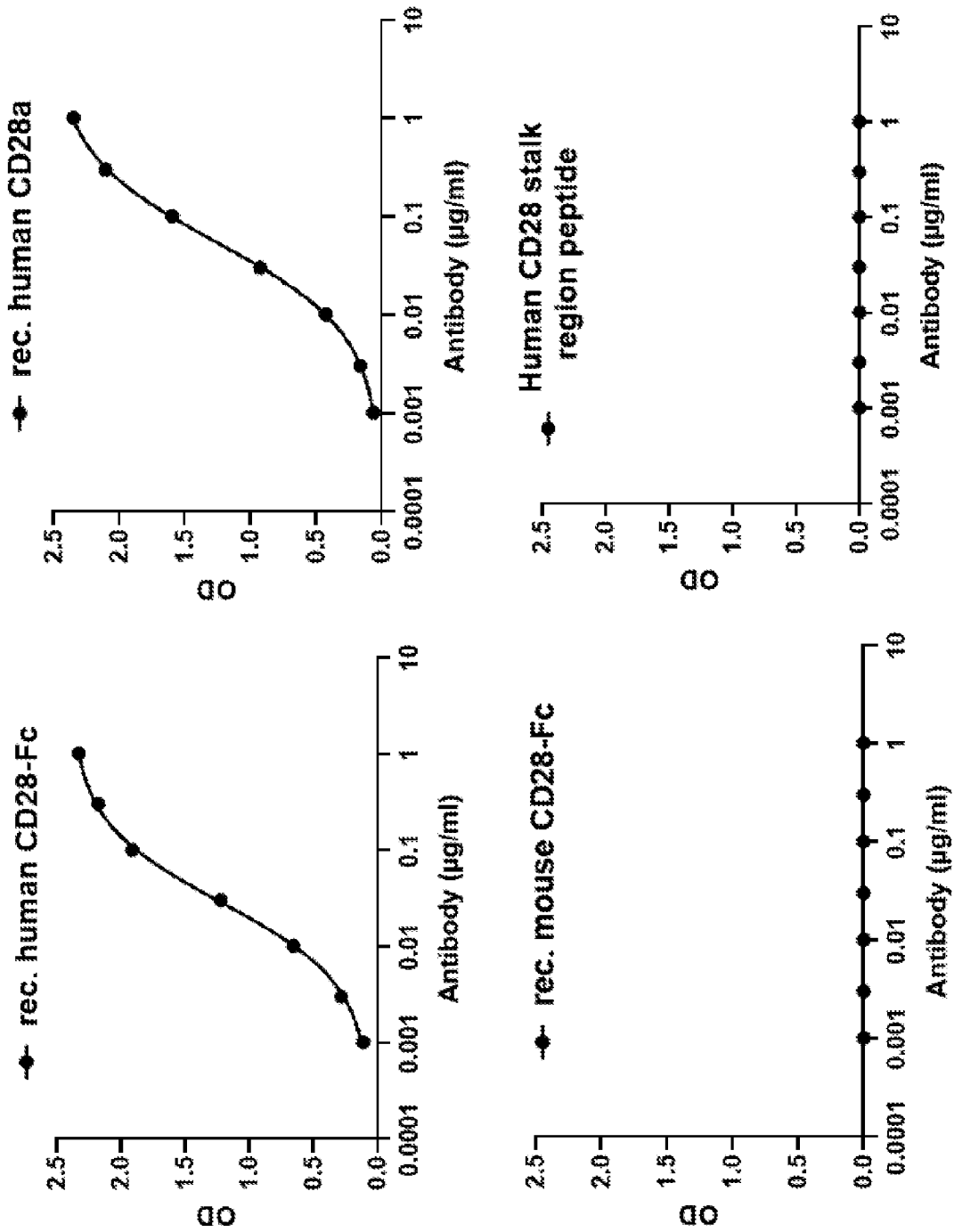

These results suggest that binding the stalk region may not have a direct effect on mCD28 signaling. However, it has been reported that monoclonal antibody MAB342, clone 37407 of R&D Systems binds in the stalk region of CD28 (see International Patent Application WO2004096139). Further, R&D systems reports that this antibody is a CD28 agonist (rndsystems.com/products/human-cd28-mab-clone-37407-37407_mab342). The binding of this antibody was therefore investigated. MAB342 was found to bind recombinant human CD28-Fc as well as recombinant human CD28a (the soluble splice variant lacking the stalk region sequence), but not recombinant mouse CD28 (FIG. 13C). However, when binding to human CD28 stalk peptide was assayed no binding was observed, strongly suggesting that this antibody does not in fact bind the CD28 stalk region (FIG. 13C).

Example 7: Characterization of Antibody-Based Agents that Eliminate the Immune-Suppressing Effects of sCD28 (Sweeping)

Three antibodies were obtained that strongly bind sCD28 and their potential efficacy as sweeping agents to lower sCD28 levels was investigated. The sequences of the three antibodies are provided hereinabove.

Figure 14A:
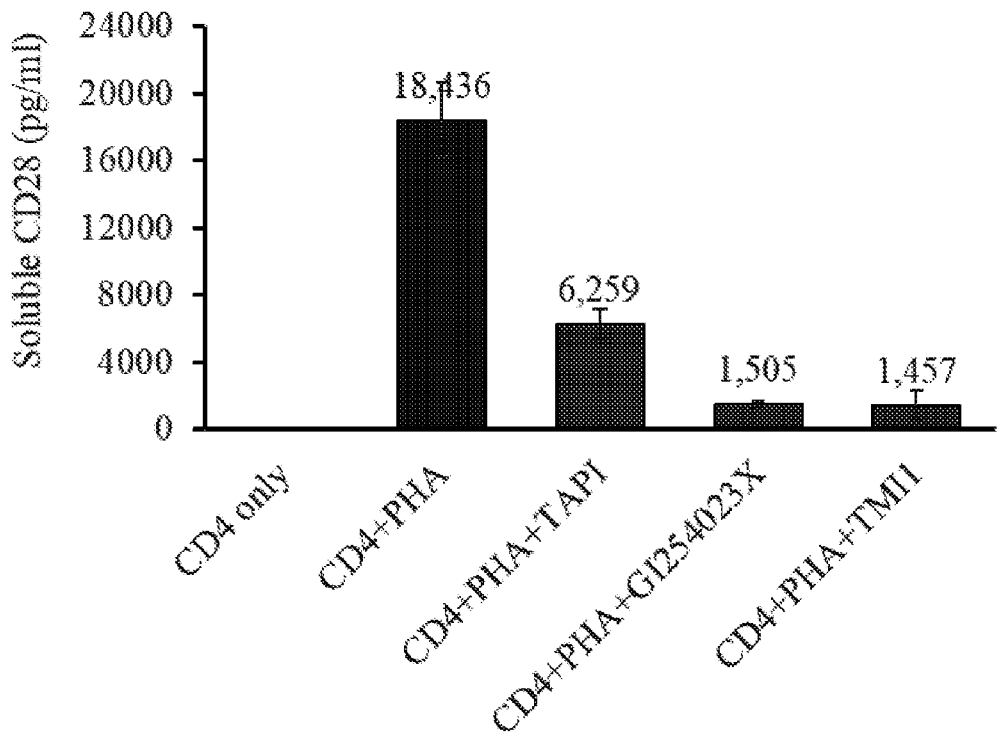
FIGS. 14A-E: (14A-B) Bar charts showing sCD28 levels in supernatant from (14A) human CD4+ T cells stimulated with PHA and (14B) human PBMCs stimulated with SEB. (14C) Line graph of results of ELISA assay on increasing concentrations of human sCD28 for antibodies #1 and #2 and the commercially available CD28.2. (14D) Line graph of results of ELISA assay on increasing concentrations of human sCD28 for each of antibodies #1, #2 and #3. (14E) Line graph of results of ELISA assay on increasing concentrations of mouse sCD28 for each of antibodies #1, #2 and #3.
Figure 14B:
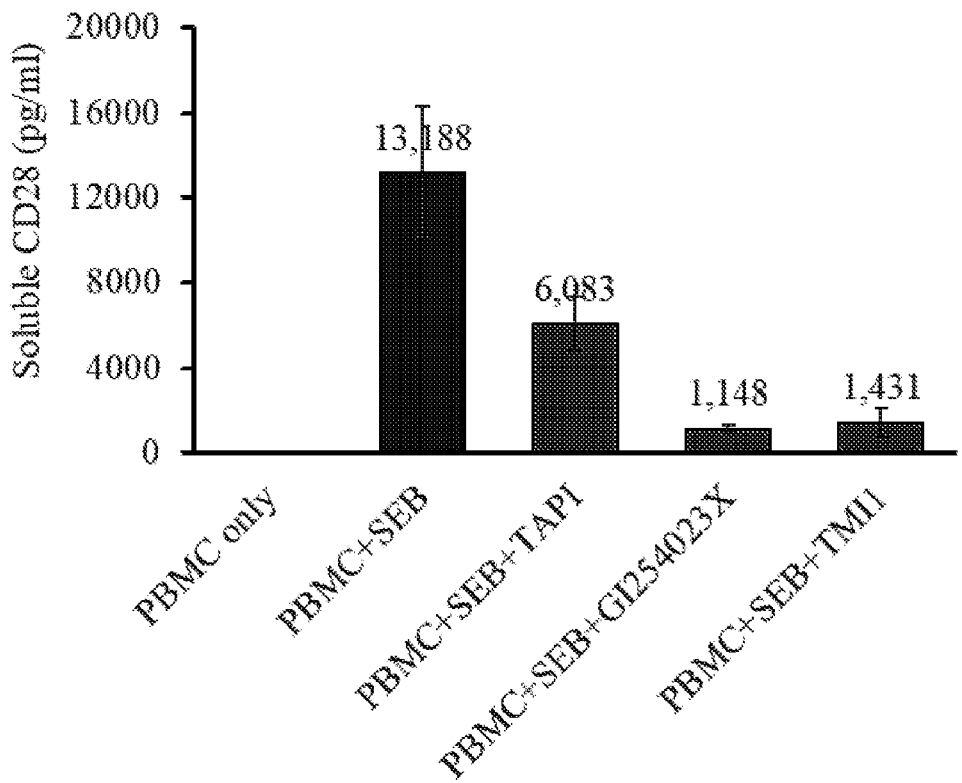

To confirm the ability of the three antibodies to binds human sCD28, human CD3 T cells were stimulated with PHA and sCD28 was measured by sandwich ELISA using two antibodies of the invention. A representative result, using antibody 1 as the detection antibody and antibody 2 as the capture antibody, is shown in FIG. 14A. Similarly, human PBMCs were stimulated with SEB and the antibodies of the invention were again capable of strongly detecting sCD28 (FIG. 14B). Lower levels of sCD28 are detected when protease inhibitors TAPI, GI254023X and TMI-1 are used confirming that it is indeed sCD28 being detected.

Figure 14C:
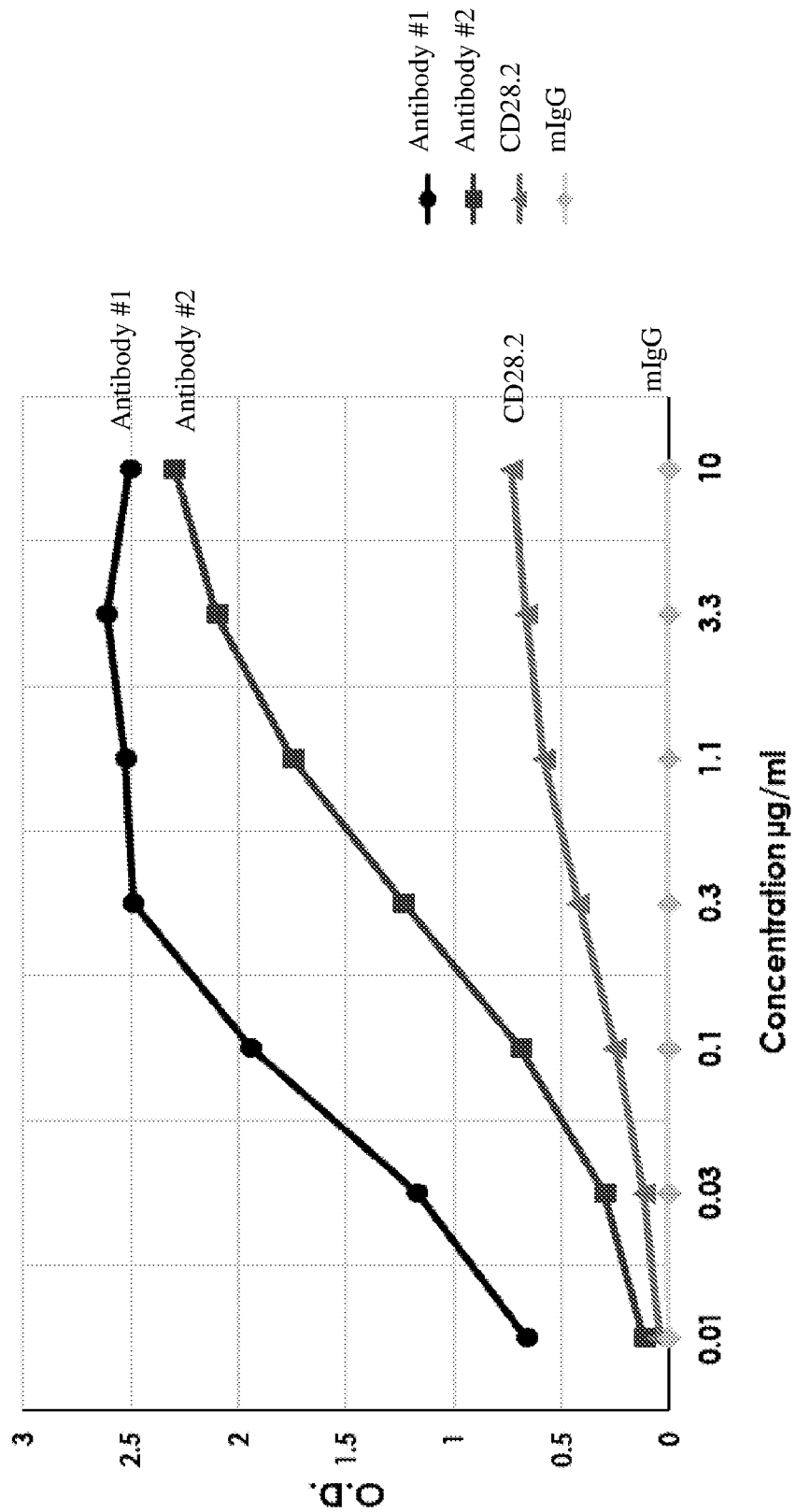
Figure 14D:
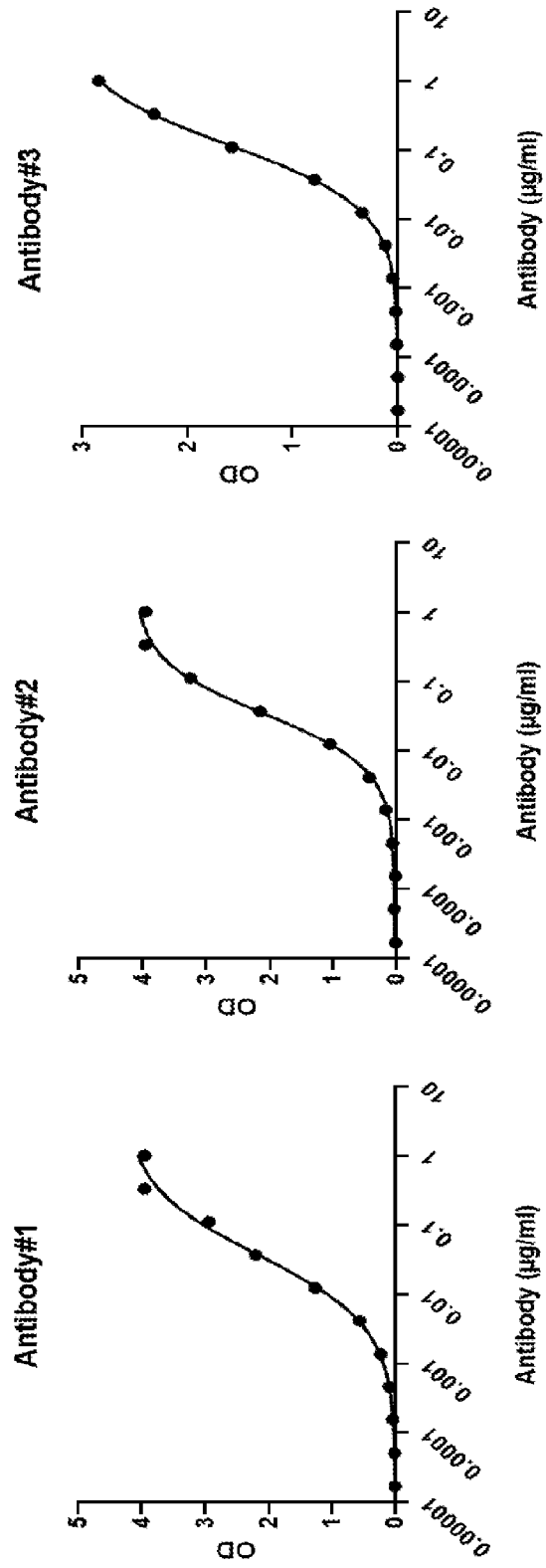
Figure 14E:
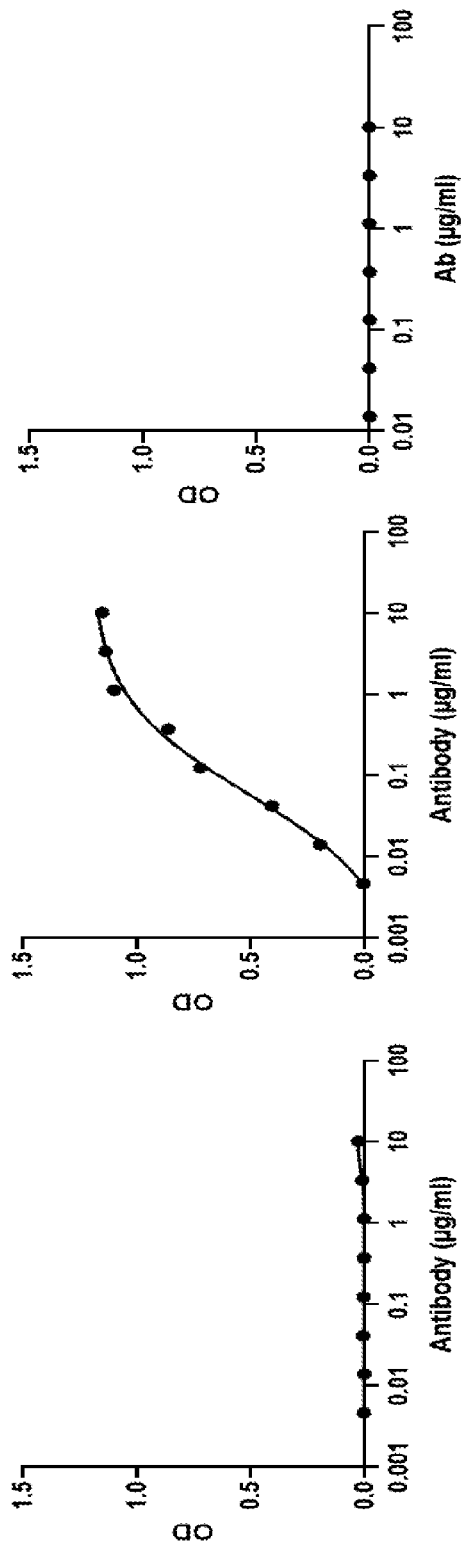

Antibodies #1 and #2 were compared to a control commercial CD28 antibody, CD28.2, which is known to bind mCD28. Direct ELISA was performed with each antibody (and mIgG as negative control) with varying concentrations of sCD28 (FIG. 14C). Recombinant human sCD28 protein was immobilized on maxisorp ELISA plates and binding was assessed by detection of bound antibody with donkey anti mouse IgG (H&L)-HRP and development with TMB. Though commercial antibody CD28.2 did bind sCD28, the binding was poor and with only a small increase in O.D. even when the input was increased 10-fold. By contrast, both antibody #1 and #2 showed much stronger binding to sCD28, with antibody #1 showing nearly ten-times greater detection, and antibody #2 showing a linear relationship to increasing antibody concentrations over the entire range examined. Direct ELISA for each antibody individually is provided in FIG. 14D. Interestingly, antibody #2 was also able to bind mouse CD28 while antibodies #1 and #3 were not (FIG. 14E).

Figure 15A:
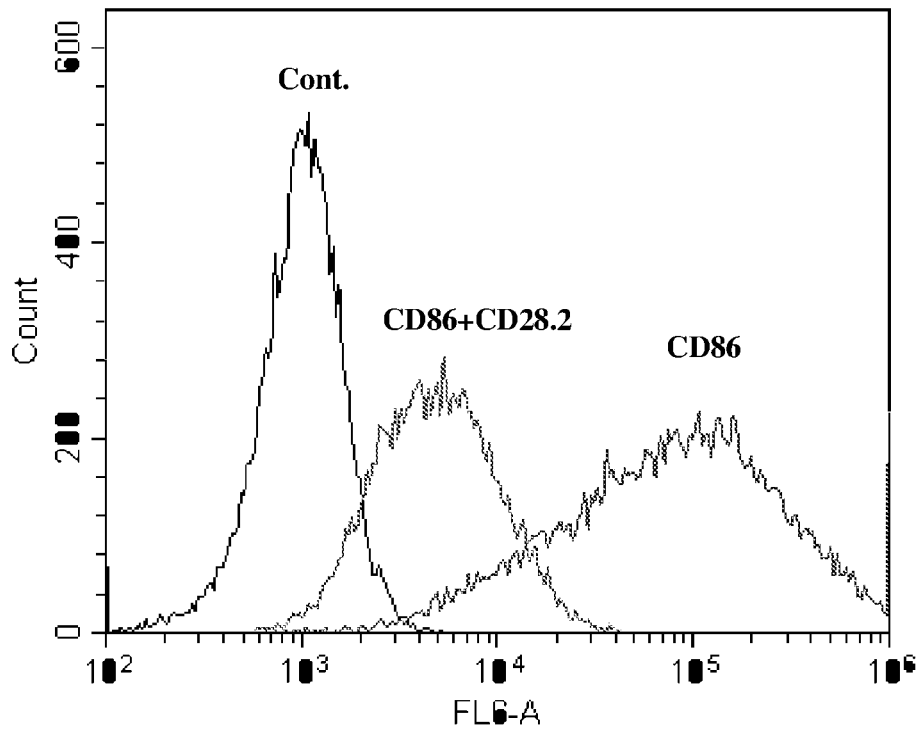
FIGS. 15A-I: (15A-D) FACS histograms showing CD86 binding to cells expressing mCD28, after addition of CD86 alone (red lines) or addition of CD86 and (15A) CD28.2, (15B) Antibody #1, (15C) Antibody #2, (15D) Antibody #3 and (15E) mIgG control (green lines). Secondary antibody alone was added to show unstained cells (black lines). (15F-G) Bar charts showing Interferon gamma (IFNγ) secretion from (15F) T cells after treatment with 2 µg/mL anti-CD3, and CD28.2 (2.0 µg/mL) or antibodies #1-3 in different dilutions (0.1-10 µg/mL, black bars), (15G) PBMCs after SEB stimulation and treatment with CD28.2 (2.0 µg/mL) or antibodies #1-3 in different dilutions (0.1-10 µg/mL, black bars), and (15H) T cells after treatment with CD80-Fc with and without varying concentration of antibodies #1-3. (15I) Histograms of the binding of antibodies #1-3 to naïve CD3 positive T cells.
Figure 15B:
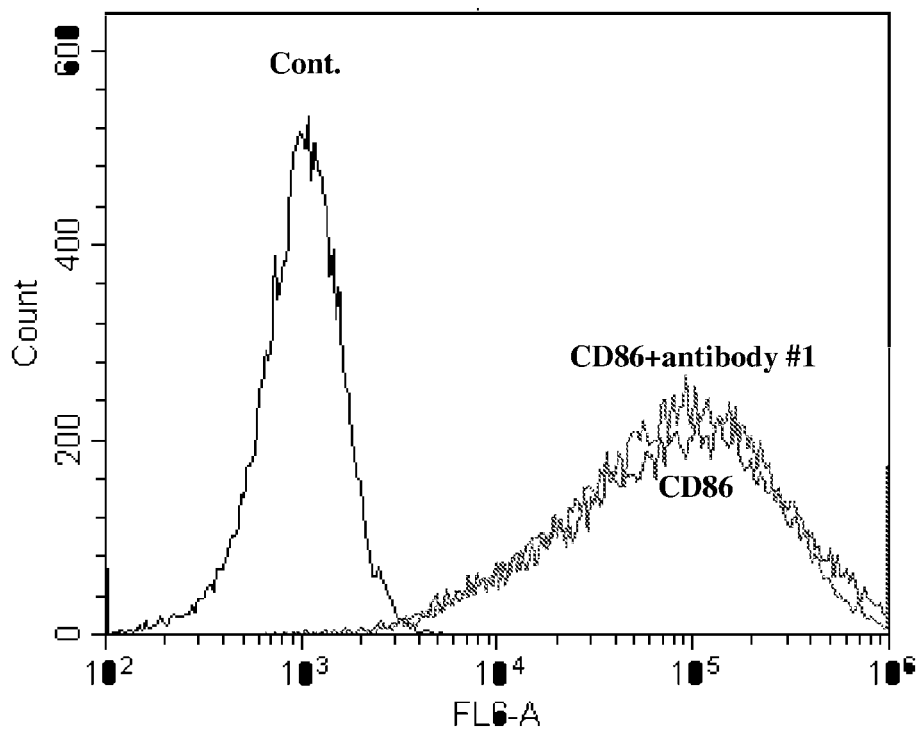
Figure 15C:
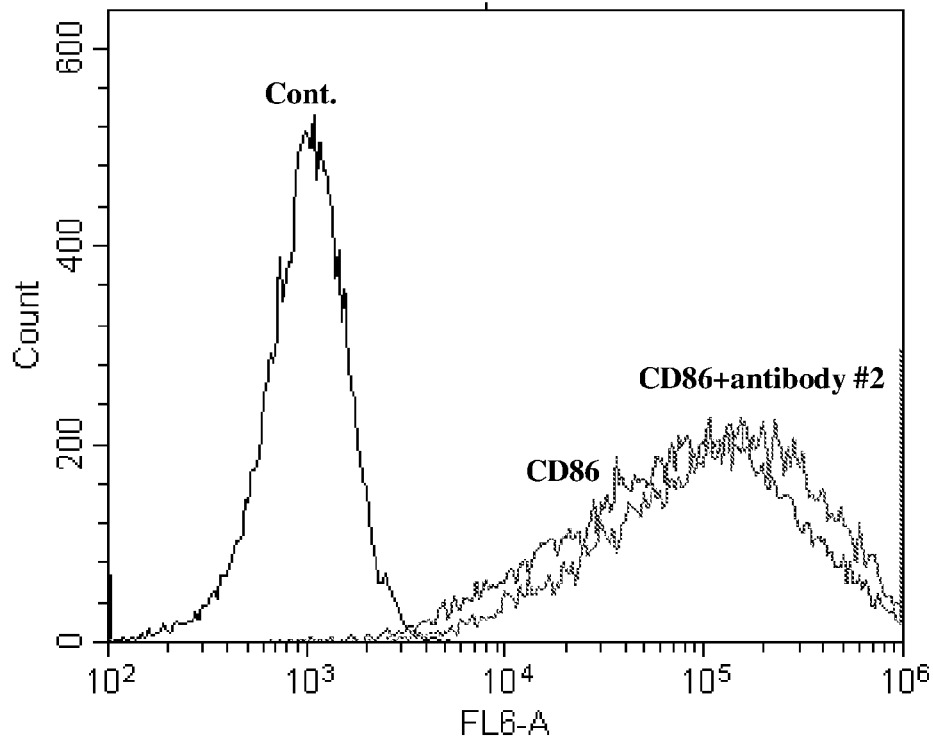
Figure 15D:
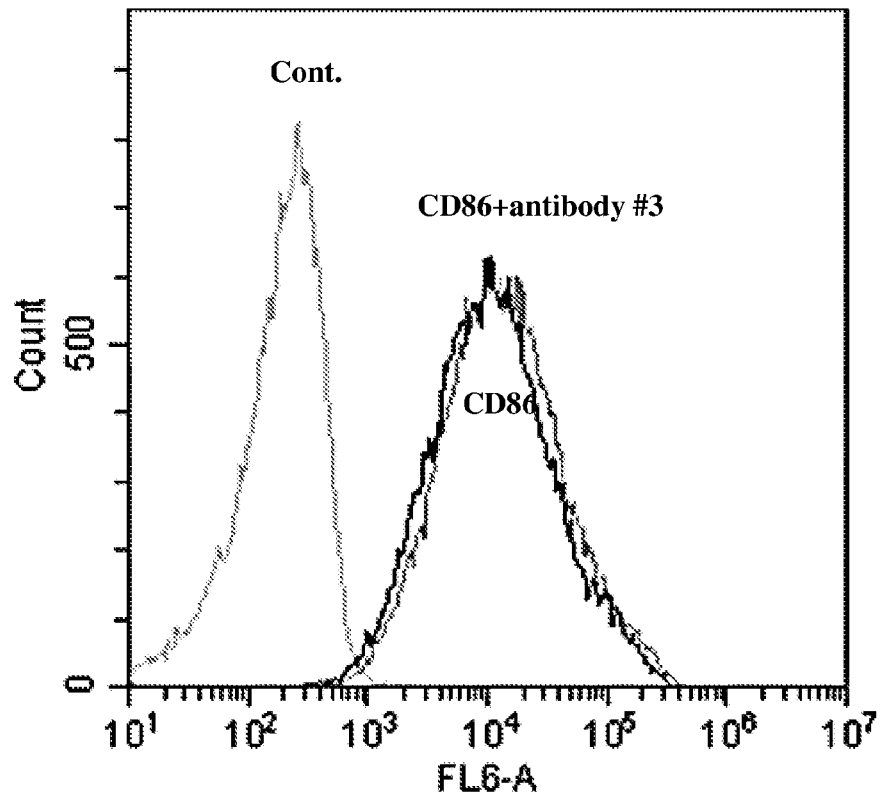
Figure 15E:
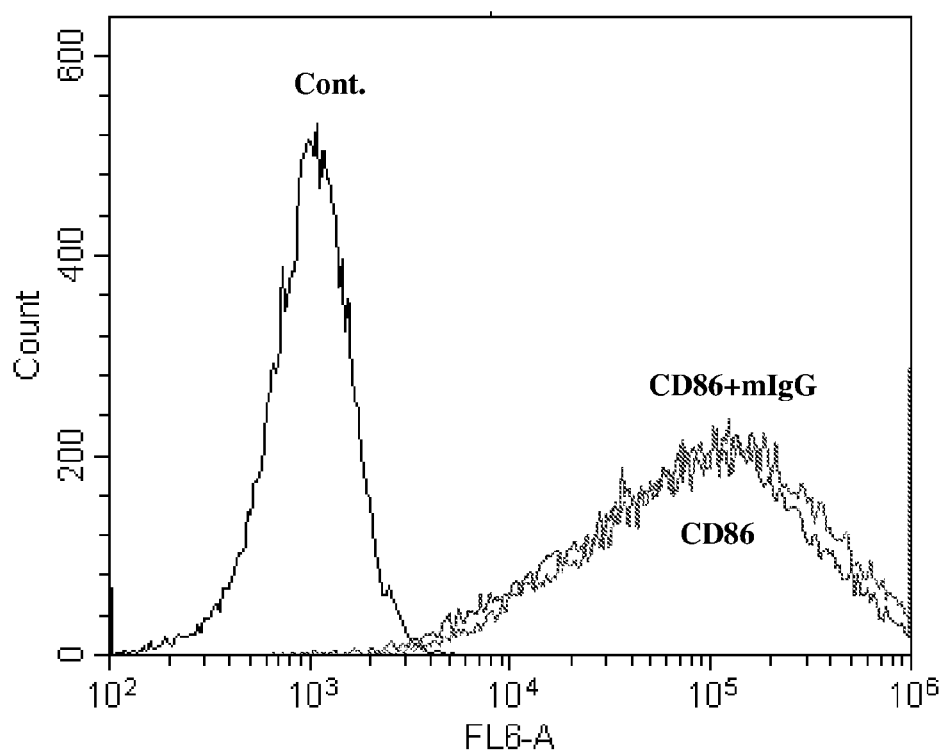

CD28.2 is known to stimulate T cell proliferation and cytokine secretion, as such it acts as a mCD28 agonist. Indeed, when binding of CD86 to mCD28 was measured by FACS, the addition of CD28.2 greatly decreased CD86 binding (FIG. 15A), indicating that CD28.2 binds to, or occludes, the ligand binding domain of mCD28. By contrast, none of antibody #1 (FIG. 15B), antibody #2 (FIG. 15C), or antibody #3 (FIG. 15D) blocked binding of CD86 to mCD28, and indeed both antibodies appear comparable to the mIgG control (FIG. 15E).

Figure 15F:
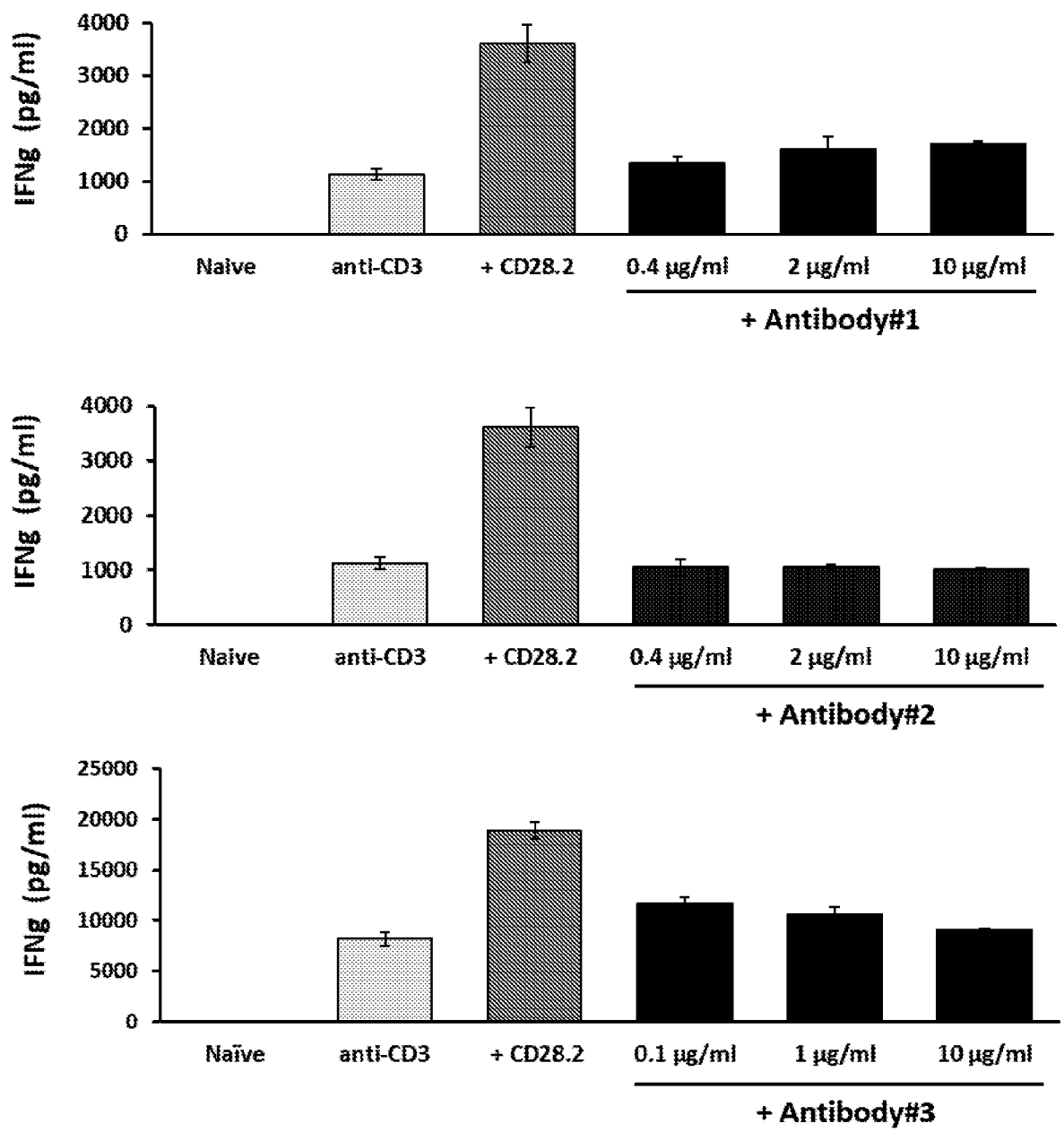
Figure 15G:
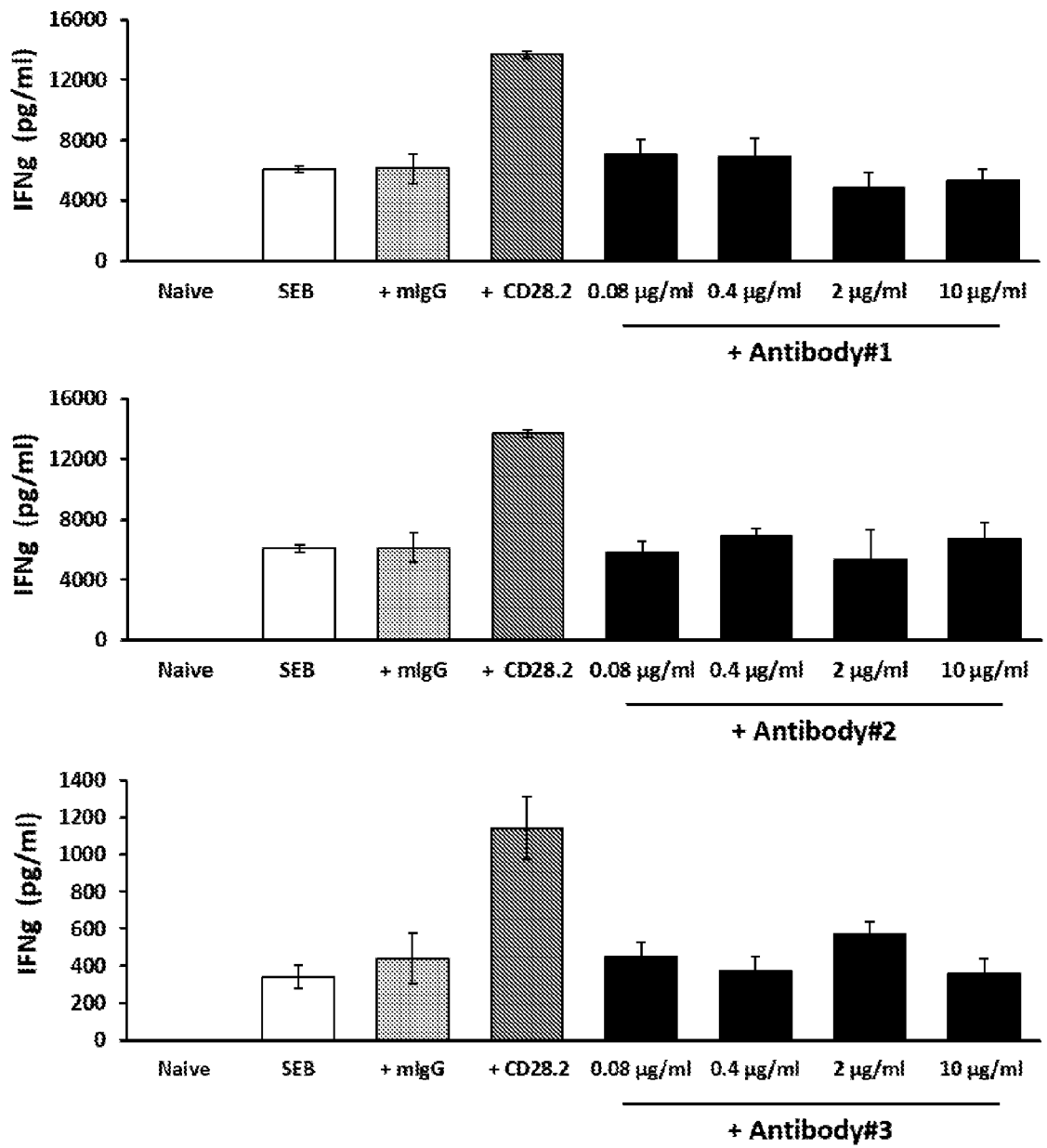

Interferon gamma (IFNγ) secretion was measured as a representative of pro-inflammatory cytokine secretion by T cells. In the presence of anti-CD3 stimulation, antibody CD28.2 induced robust IFNγ secretion indicating that the T cells had been activated. By contrast, Antibodies #1, #2 and #3 all had no effect on IFN secretion at various concentrations (FIG. 15F). Thus, while CD28.2 acts as a mCD28 agonist, antibodies #1-3 are not agonistic. Similar results were found when human PBMCs were stimulated with SEB (FIG. 15G).

Figure 15H:
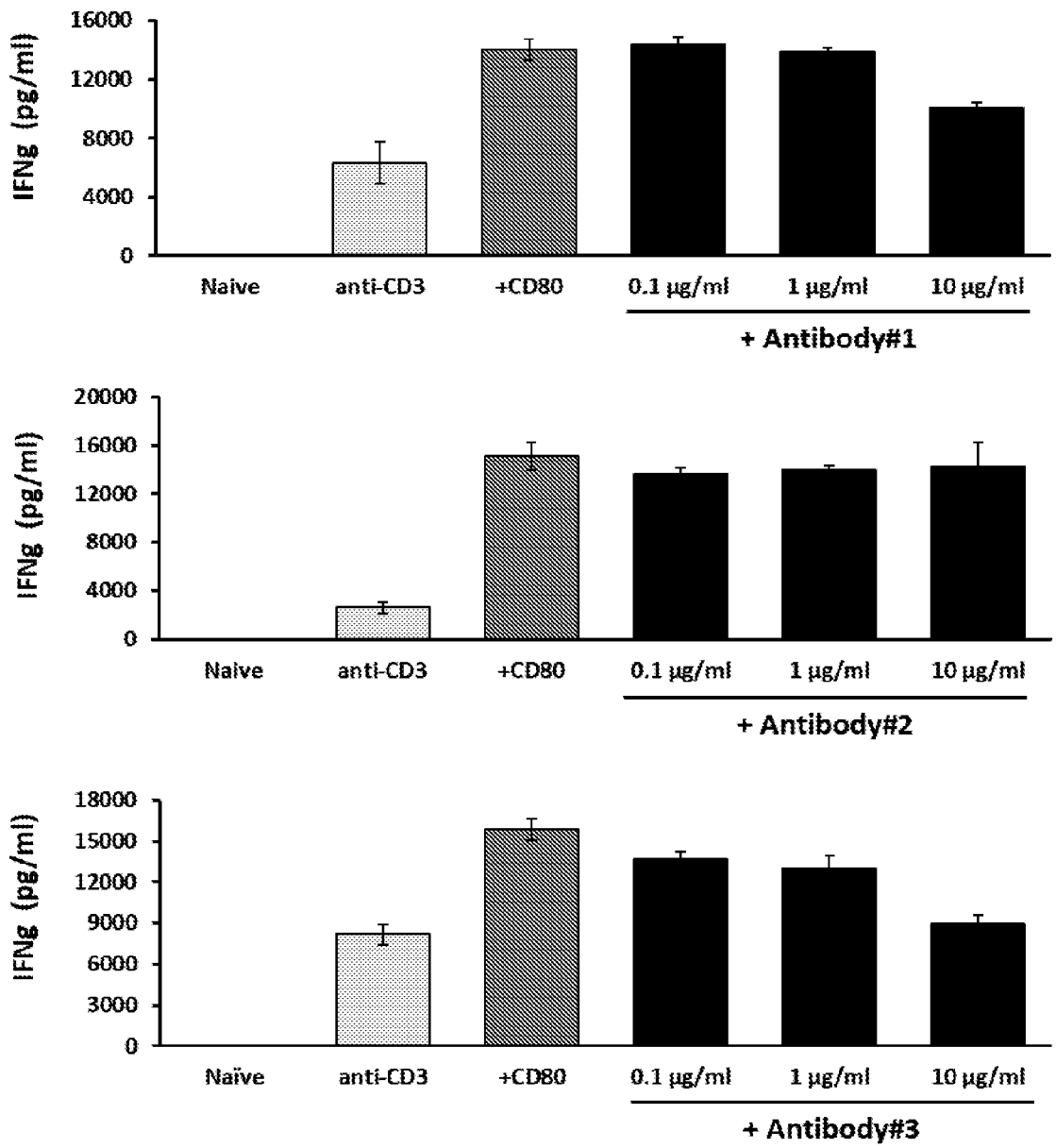

Similarly, when human isolated T cells were stimulated with anti-CD3 antibodies, CD80-Fc behaves as an agonist increasing IFN gamma secretion. Addition of an antagonist should decrease the effect of CD80, however, when antibodies #1-3 were added, no reduction in secretion was observed (FIG. 15H). This indicates that antibodies #1-3 are also not antagonistic.

Figure 15I:
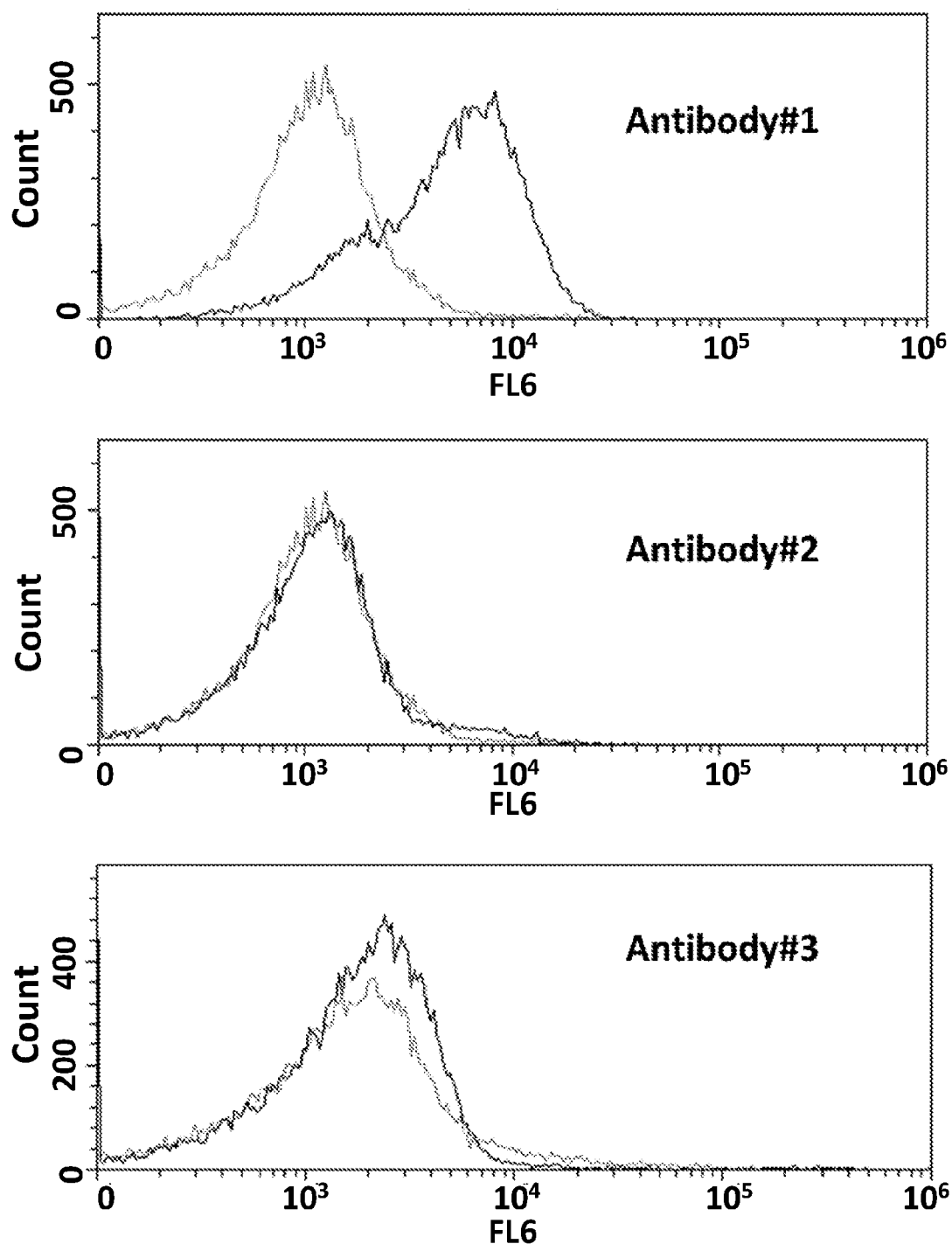

Lastly, the ability of antibodies #1-3 to bind to mCD28 at all was examined. While it is not essential that a sCD28 antibody not bind mCD28 it is advantageous. Such an antibody could be used for specific detection of the soluble protein, and if used therapeutically would have no effect on the membranal form. Naïve isolated CD3 T cells were evaluated by FACs to assay mCD28 binding. Cells were incubated with antibodies #1-3 (20 μg/mL dark grey histograms) or isotype controls (mIgG, 20 μg/mL, light grey histograms). Binding detection was performed with Alexa Fluor 647-conjugated goat anti mouse secondary antibody. As can be seen in FIG. 15I, only antibody #1 bound mCD28 at all. Antibodies #2 and #3 do not bind CD28 on the cell surface and thus are completely specific for sCD28.

Example 8: Antibodies can be Used to Remove sCD28 from Plasma

Figure 16A:
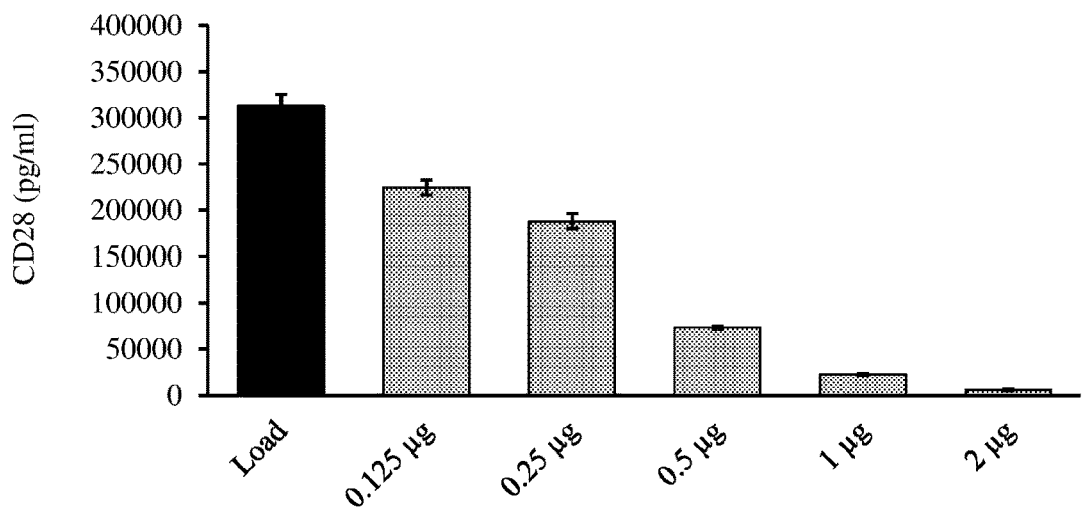
FIG. 16A-G: (16A-B) Bar graphs showing sCD28 remaining in blood from a cancer patient after mixing with beads conjugated to varying amounts of (16A) antibody #1 and (16B) antibody #2. (16C-G) Bar graphs showing sCD28 remaining in blood from (16C) a colorectal cancer patient, (16D-E) melanoma patients, (16F) an ovarian cancer patient, and (16G) a healthy patient after mixing with beads conjugated with antibody #1, CD80, CD86 and ICOSL.
Figure 16B:
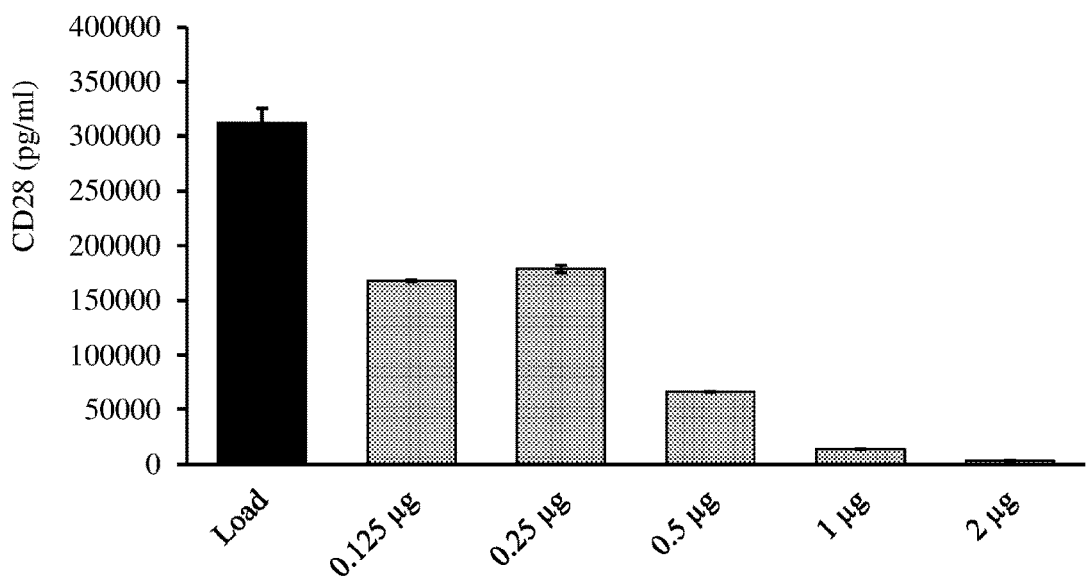

Varying amounts (0.125-2 μg) of antibodies #1 and #2 were loaded onto tosyl-activated magnetic beads according to the manufacturer's protocol (Thermo Fisher Scientific). The loaded beads were then added to plasma samples from a cancer patient, and the mixture was incubated in a thermomixer at 37° C. for 2 hours at 1000 RPM. The beads were isolated and removed from the plasma with a magnet and the amount of sCD28 remaining in the serum was measured by ELISA. Representative results from antibody #1 (FIG. 16A) and antibody #2 (FIG. 16B) are provided showing that the antibodies of the invention were capable of binding and removing sCD28 from plasma.

Figure 16C:
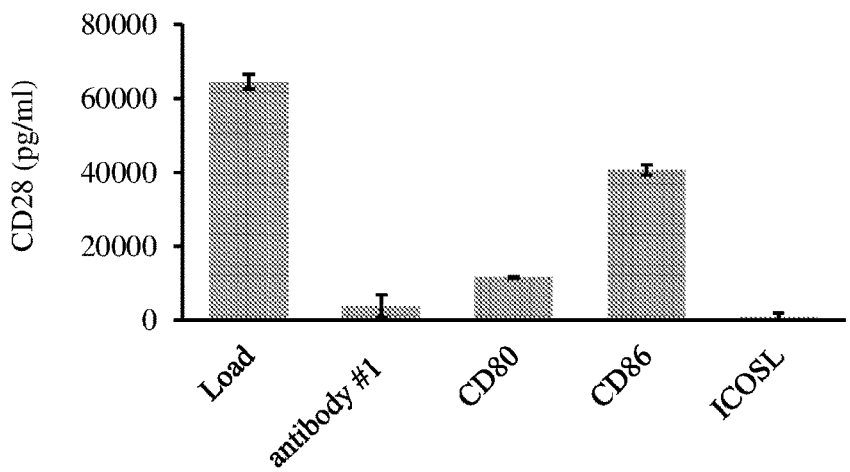
Figure 16D:
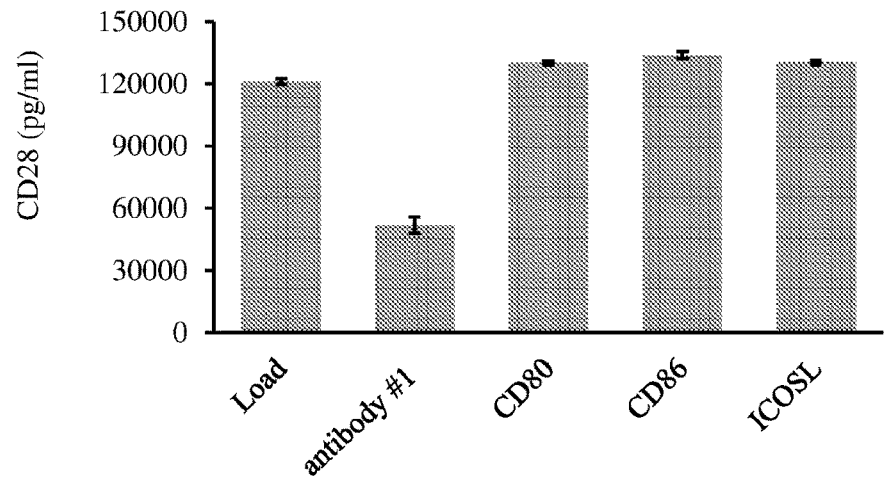
Figure 16E:
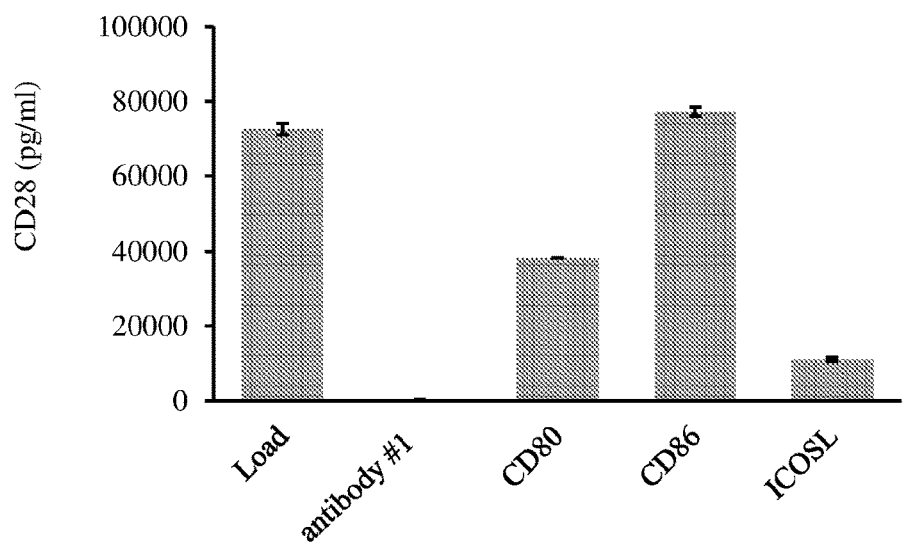
Figure 16F:
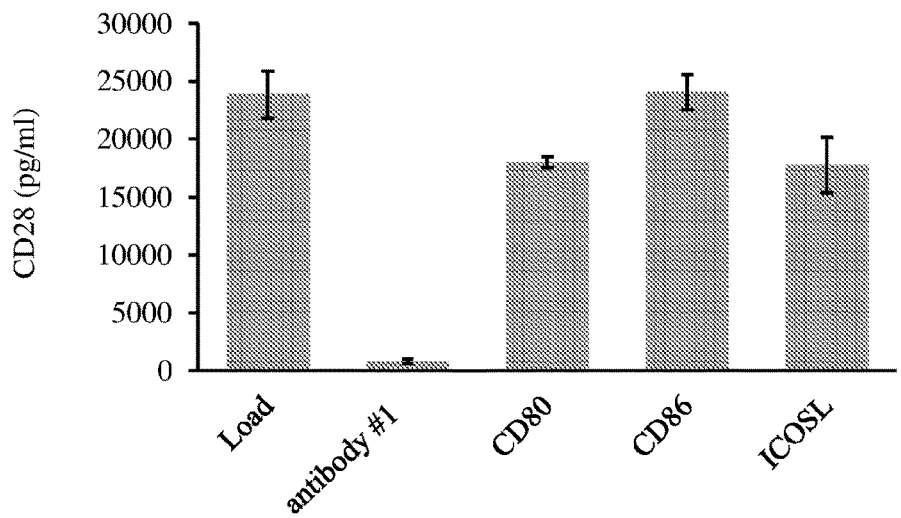
Figure 16G:
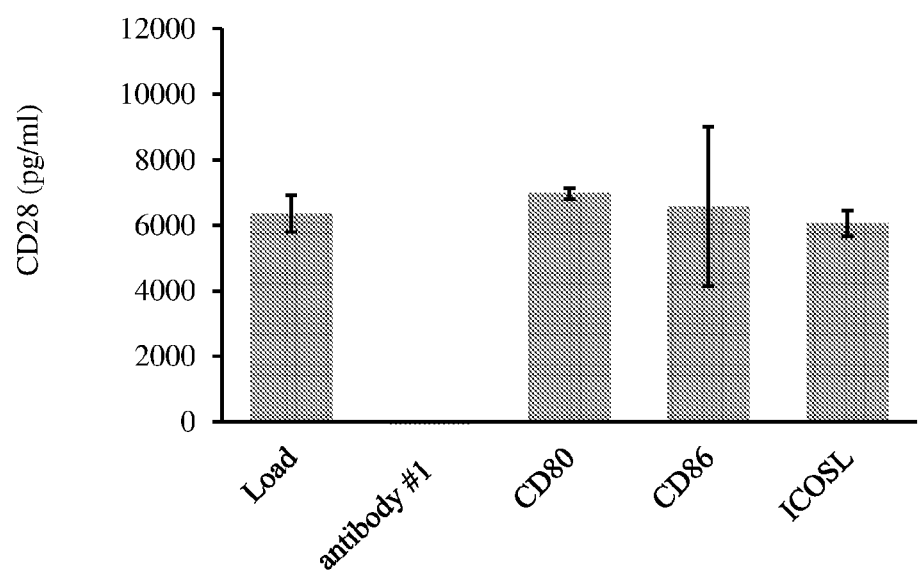

Antibody #1 was further tested on various cancer samples (melanoma, colorectal and ovarian) and compared to three B7 molecules which are known ligands of CD28. About 1.5 μg of antibody #1, CD80, CD86 and ICOSL were each loaded onto tosyl-activated magnetic beads and the beads were mixed with plasma as before. A colorectal sample (FIG. 16C), as well as two melanoma samples (FIG. 16D-E), an ovarian sample (FIG. 16F) and a sample from a healthy donor (FIG. 16G) were all tested. Antibody #1 was superior to the other three molecules tested, and in all cases was able to decrease sCD28 levels in the plasma to at or below the levels observed in the healthy sample. Indeed antibody #1 decreased sCD28 to nearly undetectable levels in all the samples with the exception of one of the melanoma samples (FIG. 16D), although even in this sample a reduction of greater than 50% was observed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of improving PD-1/PD-L1 based immunotherapy in a subject suffering from cancer, the method comprising decreasing soluble CD28 (sCD28) levels in said subject; thereby improving PD-1/PD-L1 based immunotherapy.

2. The method of claim 1, wherein said subject does not respond or lowly responds to PD-1 and/or PD-L1 based immunotherapy.

3. The method of claim 1, wherein said method does not degrade mCD28 or decrease mCD28-mediated immune cell activation.

4. The method of claim 1, wherein said subject's blood prior to said decreasing comprises at least 5 ng/ml sCD28.

5. The method of claim 1, further comprising administering another immunotherapy to said subject, optionally wherein said immunotherapy is selected from a checkpoint inhibitor, a chimeric antigen receptor (CAR) based therapy and a cancer vaccine.

6. The method of claim 1, further comprising administering to said subject said PD-1/PD-L1 based immunotherapy.

7. The method of claim 6, wherein said PD-1/PD-L1 based immunotherapy is a PD-1/PD-L1 checkpoint inhibitor.

8. The method of claim 7, wherein said PD-1/PD-L1 checkpoint inhibitor is a PD-1 or PD-L1 blocking antibody.

9. The method of claim 8, wherein said PD-1/PD-L1 checkpoint inhibitor is selected from pembrolizumab, nivolumab, pidilizumab, cemiplimab, atezolizumab, avelumab, and durvalumab.

10. The method of claim 1, wherein said subject suffers from a cancer selected from melanoma, head and neck cancer, non-small cell lung cancer, ovarian cancer, kidney cancer, gastric cancer and colorectal cancer.

* * * * *

SEQUENCE LISTING

```
<160> NUMBER OF SEQ ID NOS: 56

<210> SEQ ID NO 1
<211> LENGTH: 220
<212> TYPE: PRT
<213> ORGANISM: Homo sapiens

<400> SEQUENCE: 1

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175
```

```
Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 2
<211> LENGTH: 202
<212> TYPE: PRT
<213> ORGANISM: Homo sapiens

<400> SEQUENCE: 2

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro Phe Trp Val Leu Val Val Val Gly Gly Val
    130                 135                 140

Leu Ala Cys Tyr Ser Leu Leu Val Thr Val Ala Phe Ile Ile Phe Trp
145                 150                 155                 160

Val Arg Ser Lys Arg Ser Arg Leu Leu His Ser Asp Tyr Met Asn Met
                165                 170                 175

Thr Pro Arg Arg Pro Gly Pro Thr Arg Lys His Tyr Gln Pro Tyr Ala
            180                 185                 190

Pro Pro Arg Asp Phe Ala Ala Tyr Arg Ser
        195                 200

<210> SEQ ID NO 3
<211> LENGTH: 663
<212> TYPE: DNA
<213> ORGANISM: Homo sapiens

<400> SEQUENCE: 3
atgctcaggc tgctcttggc tctcaactta ttcccttcaa ttcaagtaac aggaaacaag      60
attttggtga agcagtcgcc catgcttgta gcgtacgaca atgcggtcaa ccttagctgc     120
aagtattcct acaatctctt ctcaagggag ttccgggcat ccttcacaa aggactggat     180 agtgctgtgg aagtctgtgt tgtatatggg aattactccc agcagcttca ggtttactca     240
aaaacggggt tcaactgtga tgggaaattg gcaatgaat cagtgacatt ctacctccag     300
aatttgtatg ttaaccaaac agatatttac ttctgcaaaa ttgaagttat gtatcctcct     360
ccttacctag acaatgagaa gagcaatgga accattatcc atgtgaaagg aaacaccttt     420
tgtccaagtc ccctatttcc cggaccttct aagcccttt gggtgctggt ggtggttggt     480
```

```
ggagtcctgg cttgctatag cttgctagta acagtggcct ttattatttt ctgggtgagg    540
agtaagagga gcaggctcct gcacagtgac tacatgaaca tgactccccg ccgcccggg     600 cccacccgca agcattacca gccctatgcc ccaccacgcg acttcgcagc ctatcgctcc    660
tga                                                                 663
```

<210> SEQ ID NO 4
<211> LENGTH: 27
<212> TYPE: PRT
<213> ORGANISM: Homo sapiens

<400> SEQUENCE: 4

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 5
<211> LENGTH: 139
<212> TYPE: PRT
<213> ORGANISM: Homo sapiens

<400> SEQUENCE: 5

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Glu Glu
    130                 135

<210> SEQ ID NO 6
<211> LENGTH: 121
<212> TYPE: PRT
<213> ORGANISM: Homo sapiens

<400> SEQUENCE: 6

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr

```
              65                  70                  75                  80
Leu Gln Asn Leu Tyr Val Asn Gln Thr Asp Ile Tyr Phe Cys Lys Ile
                    85                  90                  95

Glu Val Met Tyr Pro Pro Tyr Leu Asp Asn Glu Lys Ser Asn Gly
            100                 105                 110

Thr Ile Ile His Val Lys Gly Glu Glu
            115                 120
```

<210> SEQ ID NO 7
<211> LENGTH: 538
<212> TYPE: DNA
<213> ORGANISM: Homo sapiens

<400> SEQUENCE: 7

```
atgctcaggc tgctcttggc tctcaactta ttcccttcaa ttcaagtaac aggaaacaag     60
attttggtga agcagtcgcc catgcttgta gcgtacgaca atgcggtcaa ccttagctgc    120
aagtattcct acaatctctt ctcaagggag ttccggcat cccttcacaa aggactggat    180
agtgctgtgg aagtctgtgt tgtatatggg aattactccc agcagcttca ggtttactca    240
aaaacggggt tcaactgtga tgggaaattg ggcaatgaat cagtgacatt ctacctccag    300
aatttgtatg ttaaccaaac agatatttac ttctgcaaaa ttgaagttat gtatcctcct    360
ccttacctag acaatgagaa gagcaatgga accattatcc atgtgaaagg tgaggagtaa    420
gaggagcagg ctcctgcaca gtgactacat gaacatgact ccccgccgcc ccgggcccac    480
ccgcaagcat taccagccct atgccccacc acgcgacttc gcagcctatc gctcctga     538
```

<210> SEQ ID NO 8
<211> LENGTH: 110
<212> TYPE: PRT
<213> ORGANISM: Homo sapiens

<400> SEQUENCE: 8

```
Met Leu Val Ala Tyr Asp Asn Ala Val Asn Leu Ser Cys Lys Tyr Ser
1               5                   10                  15

Tyr Asn Leu Phe Ser Arg Glu Phe Arg Ala Ser Leu His Lys Gly Leu
            20                  25                  30

Asp Ser Ala Val Glu Val Cys Val Val Tyr Gly Asn Tyr Ser Gln Gln
        35                  40                  45

Leu Gln Val Tyr Ser Lys Thr Gly Phe Asn Cys Asp Gly Lys Leu Gly
    50                  55                  60

Asn Glu Ser Val Thr Phe Tyr Leu Gln Asn Leu Tyr Val Asn Gln Thr
65                  70                  75                  80

Asp Ile Tyr Phe Cys Lys Ile Glu Val Met Tyr Pro Pro Tyr Leu
                85                  90                  95

Asp Asn Glu Lys Ser Asn Gly Thr Ile Ile His Val Lys Gly
            100                 105                 110
```

<210> SEQ ID NO 9
<211> LENGTH: 16
<212> TYPE: PRT
<213> ORGANISM: Homo sapiens

<400> SEQUENCE: 9

```
Gly Lys His Leu Cys Pro Ser Pro Leu Phe Pro Gly Pro Ser Lys Pro
1               5                   10                  15
```

<210> SEQ ID NO 10

```
<211> LENGTH: 19
<212> TYPE: PRT
<213> ORGANISM: Homo sapiens

<400> SEQUENCE: 10

His Val Lys Gly Lys His Leu Cys Pro Ser Pro Leu Phe Pro Gly Pro
1               5                   10                  15

Ser Lys Pro

<210> SEQ ID NO 11
<211> LENGTH: 8
<212> TYPE: DNA
<213> ORGANISM: Homo sapiens

<400> SEQUENCE: 11 aaaggtga                                                                8

<210> SEQ ID NO 12
<211> LENGTH: 7
<212> TYPE: PRT
<213> ORGANISM: Artificial
<220> FEATURE:
<223> OTHER INFORMATION: Synthetic

<400> SEQUENCE: 12

Gly Tyr Thr Leu Thr Asn Tyr
1               5

<210> SEQ ID NO 13
<211> LENGTH: 6
<212> TYPE: PRT
<213> ORGANISM: Artificial
<220> FEATURE:
<223> OTHER INFORMATION: Synthetic

<400> SEQUENCE: 13

Asn Thr Tyr Thr Gly Lys
1               5

<210> SEQ ID NO 14
<211> LENGTH: 9
<212> TYPE: PRT
<213> ORGANISM: Artificial
<220> FEATURE:
<223> OTHER INFORMATION: Synthetic

<400> SEQUENCE: 14

Gly Asp Ala Asn Gln Gln Phe Ala Tyr
1               5

<210> SEQ ID NO 15
<211> LENGTH: 11
<212> TYPE: PRT
<213> ORGANISM: Artificial
<220> FEATURE:
<223> OTHER INFORMATION: Synthetic

<400> SEQUENCE: 15

Lys Ala Ser Gln Asp Ile Asn Ser Tyr Leu Ser
1               5                   10

<210> SEQ ID NO 16
<211> LENGTH: 7
<212> TYPE: PRT
<213> ORGANISM: Artificial
<220> FEATURE:
```

```
<223> OTHER INFORMATION: Synthetic

<400> SEQUENCE: 16

Arg Ala Asn Arg Leu Val Asp
1               5

<210> SEQ ID NO 17
<211> LENGTH: 9
<212> TYPE: PRT
<213> ORGANISM: Artificial
<220> FEATURE:
<223> OTHER INFORMATION: Synthetic

<400> SEQUENCE: 17

Leu Gln Tyr Asp Glu Phe Pro Pro Thr
1               5

<210> SEQ ID NO 18
<211> LENGTH: 7
<212> TYPE: PRT
<213> ORGANISM: Artificial
<220> FEATURE:
<223> OTHER INFORMATION: Synthetic

<400> SEQUENCE: 18

Gly Tyr Thr Phe Thr Ser Tyr
1               5

<210> SEQ ID NO 19
<211> LENGTH: 6
<212> TYPE: PRT
<213> ORGANISM: Artificial
<220> FEATURE:
<223> OTHER INFORMATION: Synthetic

<400> SEQUENCE: 19

Tyr Pro Gly Asp Gly Asp
1               5

<210> SEQ ID NO 20
<211> LENGTH: 9
<212> TYPE: PRT
<213> ORGANISM: Artificial
<220> FEATURE:
<223> OTHER INFORMATION: Synthetic

<400> SEQUENCE: 20

Asn Tyr Arg Tyr Ser Ser Phe Gly Tyr
1               5

<210> SEQ ID NO 21
<211> LENGTH: 17
<212> TYPE: PRT
<213> ORGANISM: Artificial
<220> FEATURE:
<223> OTHER INFORMATION: Synthetic

<400> SEQUENCE: 21

Lys Ser Ser Gln Ser Leu Leu Asn Ser Gly Asn Gln Lys Asn Tyr Leu
1               5                   10                  15

Thr

<210> SEQ ID NO 22
<211> LENGTH: 7
<212> TYPE: PRT
<213> ORGANISM: Artificial
```

```
<220> FEATURE:
<223> OTHER INFORMATION: Synthetic

<400> SEQUENCE: 22

Trp Ala Ser Thr Arg Glu Ser
1               5

<210> SEQ ID NO 23
<211> LENGTH: 9
<212> TYPE: PRT
<213> ORGANISM: Artificial
<220> FEATURE:
<223> OTHER INFORMATION: Synthetic

<400> SEQUENCE: 23

Gln Ser Asp Tyr Ser Tyr Pro Leu Thr
1               5

<210> SEQ ID NO 24
<211> LENGTH: 7
<212> TYPE: PRT
<213> ORGANISM: Artificial
<220> FEATURE:
<223> OTHER INFORMATION: Synthetic

<400> SEQUENCE: 24

Gly Tyr Thr Phe Thr Asp Tyr
1               5

<210> SEQ ID NO 25
<211> LENGTH: 6
<212> TYPE: PRT
<213> ORGANISM: Artificial
<220> FEATURE:
<223> OTHER INFORMATION: Synthetic

<400> SEQUENCE: 25

Asn Pro Asn Tyr Asp Ser
1               5

<210> SEQ ID NO 26
<211> LENGTH: 12
<212> TYPE: PRT
<213> ORGANISM: Artificial
<220> FEATURE:
<223> OTHER INFORMATION: Synthetic

<400> SEQUENCE: 26

Ser Ser Pro Tyr Tyr Asp Ser Asn His Phe Asp Tyr
1               5                   10

<210> SEQ ID NO 27
<211> LENGTH: 10
<212> TYPE: PRT
<213> ORGANISM: Artificial
<220> FEATURE:
<223> OTHER INFORMATION: Synthetic

<400> SEQUENCE: 27

Ser Ala Arg Ser Ser Ile Asn Tyr Met His
1               5                   10

<210> SEQ ID NO 28
<211> LENGTH: 7
<212> TYPE: PRT
<213> ORGANISM: Artificial
<220> FEATURE:
```

```
<223> OTHER INFORMATION: Synthetic

<400> SEQUENCE: 28

Asp Thr Ser Lys Leu Ala Ser
1               5

<210> SEQ ID NO 29
<211> LENGTH: 9
<212> TYPE: PRT
<213> ORGANISM: Artificial
<220> FEATURE:
<223> OTHER INFORMATION: Synthetic

<400> SEQUENCE: 29

His Gln Arg Asn Ser Tyr Pro Phe Thr
1               5

<210> SEQ ID NO 30
<211> LENGTH: 10
<212> TYPE: PRT
<213> ORGANISM: Artificial
<220> FEATURE:
<223> OTHER INFORMATION: Synthetic

<400> SEQUENCE: 30

Gly Phe Thr Phe Ser Ser Tyr Tyr Met Ser
1               5                   10

<210> SEQ ID NO 31
<211> LENGTH: 17
<212> TYPE: PRT
<213> ORGANISM: Artificial
<220> FEATURE:
<223> OTHER INFORMATION: Synthetic

<400> SEQUENCE: 31

Thr Ile Ser Asp Gly Gly Asp Asn Thr Tyr Tyr Ala Gly Thr Val Thr
1               5                   10                  15

Gly

<210> SEQ ID NO 32
<211> LENGTH: 9
<212> TYPE: PRT
<213> ORGANISM: Artificial
<220> FEATURE:
<223> OTHER INFORMATION: Synthetic

<400> SEQUENCE: 32

Ile His Trp Pro Tyr Tyr Phe Asp Ser
1               5

<210> SEQ ID NO 33
<211> LENGTH: 10
<212> TYPE: PRT
<213> ORGANISM: Artificial
<220> FEATURE:
<223> OTHER INFORMATION: Synthetic

<400> SEQUENCE: 33

Arg Ala Ser Ser Ser Val Ser Tyr Met Asn
1               5                   10

<210> SEQ ID NO 34
<211> LENGTH: 7
<212> TYPE: PRT
<213> ORGANISM: Artificial
```

```
<220> FEATURE:
<223> OTHER INFORMATION: Synthetic

<400> SEQUENCE: 34

Ala Thr Ser Asp Leu Ala Ser
1               5

<210> SEQ ID NO 35
<211> LENGTH: 9
<212> TYPE: PRT
<213> ORGANISM: Artificial
<220> FEATURE:
<223> OTHER INFORMATION: Synthetic

<400> SEQUENCE: 35

Gln Gln Trp Ser Ser His Pro Pro Thr
1               5

<210> SEQ ID NO 36
<211> LENGTH: 15
<212> TYPE: PRT
<213> ORGANISM: Artificial
<220> FEATURE:
<223> OTHER INFORMATION: Synthetic

<400> SEQUENCE: 36

Lys Gly Lys His Leu Cys Pro Ser Pro Leu Phe Pro Gly Pro Ser
1               5                   10                  15

<210> SEQ ID NO 37
<211> LENGTH: 134
<212> TYPE: PRT
<213> ORGANISM: Artificial
<220> FEATURE:
<223> OTHER INFORMATION: Synthetic

<400> SEQUENCE: 37

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
                20                  25                  30

Phe Arg Ala Ser Leu His Lys Gly Leu Asp Ser Ala Val Glu Val Cys
            35                  40                  45

Val Val Tyr Gly Asn Tyr Ser Gln Gln Leu Gln Val Tyr Ser Lys Thr
        50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro
    130

<210> SEQ ID NO 38
<211> LENGTH: 27
<212> TYPE: DNA
<213> ORGANISM: Artificial
<220> FEATURE:
<223> OTHER INFORMATION: Synthetic
```

```
<400> SEQUENCE: 38
atgctgaggc tgctcttggc tctcaac                                    27

<210> SEQ ID NO 39
<211> LENGTH: 27
<212> TYPE: DNA
<213> ORGANISM: Artificial
<220> FEATURE:
<223> OTHER INFORMATION: Synthetic

<400> SEQUENCE: 39
tcaggagcga taggctgcga agtcgcg                                    27

<210> SEQ ID NO 40
<211> LENGTH: 17
<212> TYPE: PRT
<213> ORGANISM: Artificial
<220> FEATURE:
<223> OTHER INFORMATION: Synthetic

<400> SEQUENCE: 40

Gly Lys His Leu Cys Pro Ser Pro Leu Phe Pro Gly Pro Ser Lys Pro
1               5                   10                  15

Lys

<210> SEQ ID NO 41
<211> LENGTH: 117
<212> TYPE: PRT
<213> ORGANISM: Artificial
<220> FEATURE:
<223> OTHER INFORMATION: Synthetic

<400> SEQUENCE: 41

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Leu Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Lys Pro Thr Tyr Val Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Asp Ala Asn Gln Gln Phe Ala Tyr Trp Gly Gln Gly Thr
            100                 105                 110

Leu Val Thr Val Ser
        115

<210> SEQ ID NO 42
<211> LENGTH: 442
<212> TYPE: PRT
<213> ORGANISM: Artificial
<220> FEATURE:
<223> OTHER INFORMATION: Synthetic

<400> SEQUENCE: 42

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Leu Thr Asn Tyr
```

```
            20                  25                  30
Gly Met Asn Trp Val Lys Gln Ala Pro Gly Lys Gly Leu Lys Trp Met
        35                  40                  45

Gly Trp Ile Asn Thr Tyr Thr Gly Lys Pro Thr Tyr Val Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Asp Ala Asn Gln Gln Phe Ala Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440
```

```
<210> SEQ ID NO 43
<211> LENGTH: 107
<212> TYPE: PRT
<213> ORGANISM: Artificial
<220> FEATURE:
<223> OTHER INFORMATION: Synthetic

<400> SEQUENCE: 43

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Asp Asp Met Gly Ile Tyr Tyr Cys Leu Gln Tyr Asp Glu Phe Pro Pro
                85                  90                  95

Thr Phe Gly Ala Gly Thr Lys Leu Glu Leu Lys
            100                 105

<210> SEQ ID NO 44
<211> LENGTH: 214
<212> TYPE: PRT
<213> ORGANISM: Artificial
<220> FEATURE:
<223> OTHER INFORMATION: Synthetic

<400> SEQUENCE: 44

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Asp Asp Met Gly Ile Tyr Tyr Cys Leu Gln Tyr Asp Glu Phe Pro Pro
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
```

```
                    195                 200                 205

Phe Asn Arg Asn Glu Cys
    210

<210> SEQ ID NO 45
<211> LENGTH: 118
<212> TYPE: PRT
<213> ORGANISM: Artificial
<220> FEATURE:
<223> OTHER INFORMATION: Synthetic

<400> SEQUENCE: 45

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Ile Lys Lys Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Ala Ser Glu Asp Ser Ala Val Tyr Phe Cys
                85                  90                  95

Ala Arg Asn Tyr Arg Tyr Ser Ser Phe Gly Tyr Trp Gly Gln Gly Thr
            100                 105                 110

Leu Val Thr Val Ser Ala
        115

<210> SEQ ID NO 46
<211> LENGTH: 454
<212> TYPE: PRT
<213> ORGANISM: Artificial
<220> FEATURE:
<223> OTHER INFORMATION: Synthetic

<400> SEQUENCE: 46

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Ile Lys Lys Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Ala Ser Glu Asp Ser Ala Val Tyr Phe Cys
                85                  90                  95

Ala Arg Asn Tyr Arg Tyr Ser Ser Phe Gly Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Cys Gly Asp Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160
```

```
Ser Gly Ser Leu Ser Ser Val His Thr Phe Pro Ala Leu Leu Gln
            165                 170                 175

Ser Gly Leu Tyr Thr Met Ser Ser Val Thr Val Pro Ser Ser Thr
            180                 185                 190

Trp Pro Ser Gln Thr Val Thr Cys Ser Val Ala His Pro Ala Ser Ser
            195                 200                 205

Thr Thr Val Asp Lys Lys Leu Glu Pro Ser Gly Pro Ile Ser Thr Ile
        210                 215                 220

Asn Pro Cys Pro Pro Cys Lys Glu Cys His Lys Cys Pro Ala Pro Asn
225                 230                 235                 240

Leu Glu Gly Gly Pro Ser Val Phe Ile Phe Pro Pro Asn Ile Lys Asp
                245                 250                 255

Val Leu Met Ile Ser Leu Thr Pro Lys Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ser Pro Ile Glu Arg Thr Ile Ser Lys Ile Lys Gly Leu Val Arg Ala
            340                 345                 350

Pro Gln Val Tyr Ile Leu Pro Pro Ala Glu Gln Leu Ser Arg Lys
        355                 360                 365

Asp Val Ser Leu Thr Cys Leu Val Val Gly Phe Asn Pro Gly Asp Ile
370                 375                 380

Ser Val Glu Trp Thr Ser Asn Gly His Thr Glu Glu Asn Tyr Lys Asp
385                 390                 395                 400

Thr Ala Pro Val Leu Asp Ser Asp Gly Ser Tyr Phe Ile Tyr Ser Lys
                405                 410                 415

Leu Asn Met Lys Thr Ser Lys Trp Glu Lys Thr Asp Ser Phe Ser Cys
            420                 425                 430

Asn Val Arg His Glu Gly Leu Lys Asn Tyr Tyr Leu Lys Lys Thr Ile
        435                 440                 445

Ser Arg Ser Pro Gly Lys
    450

<210> SEQ ID NO 47
<211> LENGTH: 113
<212> TYPE: PRT
<213> ORGANISM: Artificial
<220> FEATURE:
<223> OTHER INFORMATION: Synthetic

<400> SEQUENCE: 47

Asp Ile Val Met Thr Gln Ser Pro Ser Ser Leu Thr Val Thr Ala Gly
1               5                   10                  15

Glu Lys Val Thr Leu Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Gln Leu Leu Ile Tyr Trp Ala Ser Thr Arg Glu Ser Gly Val
    50                  55                  60
```

```
Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Ser
                 85                  90                  95

Asp Tyr Ser Tyr Pro Leu Thr Phe Gly Ala Gly Thr Lys Leu Glu Leu
                100                 105                 110

Lys

<210> SEQ ID NO 48
<211> LENGTH: 220
<212> TYPE: PRT
<213> ORGANISM: Artificial
<220> FEATURE:
<223> OTHER INFORMATION: Synthetic

<400> SEQUENCE: 48

Asp Ile Val Met Thr Gln Ser Pro Ser Ser Leu Thr Val Thr Ala Gly
  1               5                  10                  15

Glu Lys Val Thr Leu Ser Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Gln Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Ser
                 85                  90                  95

Asp Tyr Ser Tyr Pro Leu Thr Phe Gly Ala Gly Thr Lys Leu Glu Leu
                100                 105                 110

Lys Arg Ala Asp Ala Ala Pro Thr Val Ser Ile Phe Pro Pro Ser Ser
            115                 120                 125

Glu Gln Leu Thr Ser Gly Gly Ala Ser Val Val Cys Phe Leu Asn Asn
        130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220

<210> SEQ ID NO 49
<211> LENGTH: 121
<212> TYPE: PRT
<213> ORGANISM: Artificial
<220> FEATURE:
<223> OTHER INFORMATION: Synthetic

<400> SEQUENCE: 49

Glu Val Gln Leu Gln Gln Phe Gly Ala Glu Leu Val Lys Pro Gly Ala
  1               5                  10                  15

Ser Val Lys Ile Ser Cys Lys Ala Ser Gly Tyr Thr Phe Thr Asp Tyr
                 20                  25                  30
```

Asn Met Asp Trp Val Lys Gln Ser His Gly Lys Ser Leu Glu Trp Ile
         35                  40                  45

Gly Asp Ile Asn Pro Asn Tyr Asp Ser Thr Ala Tyr Asn Gln Lys Phe
 50                  55                  60

Met Gly Lys Ala Thr Leu Thr Val Asp Lys Ser Ser Asn Thr Ala Tyr
 65                  70                  75                  80

Met Glu Leu Arg Ser Leu Thr Ser Glu Asp Thr Ala Val Tyr Tyr Cys
                 85                  90                  95

Ala Arg Ser Ser Pro Tyr Tyr Asp Ser Asn His Phe Asp Tyr Trp Gly
                100                 105                 110

Gln Gly Thr Ser Leu Thr Val Ser Ser
            115                 120

<210> SEQ ID NO 50
<211> LENGTH: 445
<212> TYPE: PRT
<213> ORGANISM: Artificial
<220> FEATURE:
<223> OTHER INFORMATION: Synthetic

<400> SEQUENCE: 50

Glu Val Gln Leu Gln Gln Phe Gly Ala Glu Leu Val Lys Pro Gly Ala
 1               5                  10                  15

Ser Val Lys Ile Ser Cys Lys Ala Ser Gly Tyr Thr Phe Thr Asp Tyr
                 20                  25                  30

Asn Met Asp Trp Val Lys Gln Ser His Gly Lys Ser Leu Glu Trp Ile
         35                  40                  45

Gly Asp Ile Asn Pro Asn Tyr Asp Ser Thr Ala Tyr Asn Gln Lys Phe
 50                  55                  60

Met Gly Lys Ala Thr Leu Thr Val Asp Lys Ser Ser Asn Thr Ala Tyr
 65                  70                  75                  80

Met Glu Leu Arg Ser Leu Thr Ser Glu Asp Thr Ala Val Tyr Tyr Cys
                 85                  90                  95

Ala Arg Ser Ser Pro Tyr Tyr Asp Ser Asn His Phe Asp Tyr Trp Gly
                100                 105                 110

Gln Gly Thr Ser Leu Thr Val Ser Ser Ala Lys Thr Thr Pro Pro Ser
            115                 120                 125

Val Tyr Pro Leu Ala Pro Gly Ser Ala Ala Gln Thr Asn Ser Met Val
130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
                180                 185                 190

Ser Ser Thr Trp Pro Ser Glu Thr Val Thr Cys Asn Val Ala His Pro
            195                 200                 205

Ala Ser Ser Thr Lys Val Asp Lys Lys Ile Val Pro Arg Asp Cys Gly
210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
                260                 265                 270

```
Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
                340                 345                 350

Lys Glu Gln Met Ala Lys Asp Lys Val Ser Leu Thr Cys Met Ile Thr
                355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
                420                 425                 430

His His Thr Glu Lys Ser Leu Ser His Ser Pro Gly Lys
            435                 440                 445

<210> SEQ ID NO 51
<211> LENGTH: 106
<212> TYPE: PRT
<213> ORGANISM: Artificial
<220> FEATURE:
<223> OTHER INFORMATION: Synthetic

<400> SEQUENCE: 51

Gln Ile Val Leu Thr Gln Ser Pro Ala Ile Met Ser Ala Ser Pro Gly
1               5                   10                  15

Glu Lys Val Thr Met Thr Cys Ser Ala Arg Ser Ser Ile Asn Tyr Met
                20                  25                  30

His Trp Phe Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys His Gln Arg Asn Ser Tyr Pro Phe Thr
                85                  90                  95

Phe Gly Ser Gly Thr Lys Leu Glu Ile Lys
            100                 105

<210> SEQ ID NO 52
<211> LENGTH: 213
<212> TYPE: PRT
<213> ORGANISM: Artificial
<220> FEATURE:
<223> OTHER INFORMATION: Synthetic

<400> SEQUENCE: 52

Gln Ile Val Leu Thr Gln Ser Pro Ala Ile Met Ser Ala Ser Pro Gly
1               5                   10                  15

Glu Lys Val Thr Met Thr Cys Ser Ala Arg Ser Ser Ile Asn Tyr Met
                20                  25                  30
```

His Trp Phe Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys His Gln Arg Asn Ser Tyr Pro Phe Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
        210

<210> SEQ ID NO 53
<211> LENGTH: 118
<212> TYPE: PRT
<213> ORGANISM: Artificial
<220> FEATURE:
<223> OTHER INFORMATION: Synthetic

<400> SEQUENCE: 53

Asp Val Lys Leu Val Glu Ser Gly Gly Gly Leu Val Lys Leu Gly Gly
1               5                   10                  15

Ser Leu Lys Leu Ser Cys Val Ala Ser Gly Phe Thr Phe Ser Ser Tyr
            20                  25                  30

Tyr Met Ser Trp Val Arg Gln Thr Pro Glu Lys Arg Leu Glu Trp Val
        35                  40                  45

Ala Thr Ile Ser Asp Gly Gly Asp Asn Thr Tyr Tyr Ala Gly Thr Val
    50                  55                  60

Thr Gly Arg Phe Thr Ile Ser Arg Asp Phe Ala Lys Asn Thr Leu Tyr
65                  70                  75                  80

Leu Gln Met Asn Ser Leu Thr Ser Glu Asp Thr Ala Val Tyr Tyr Cys
                85                  90                  95

Ala Arg Ile His Trp Pro Tyr Tyr Phe Asp Ser Trp Gly Gln Gly Thr
            100                 105                 110

Thr Leu Thr Val Ser Ser
        115

<210> SEQ ID NO 54
<211> LENGTH: 354
<212> TYPE: PRT
<213> ORGANISM: Artificial
<220> FEATURE:
<223> OTHER INFORMATION: Synthetic

<400> SEQUENCE: 54

```
Gly Ala Cys Gly Thr Gly Ala Ala Gly Cys Thr Cys Gly Thr Gly
1               5                   10                  15
Ala Gly Thr Cys Thr Gly Gly Gly Gly Ala Gly Gly Cys Thr Thr
                20                  25                  30
Ala Gly Thr Gly Ala Ala Gly Cys Thr Thr Gly Gly Ala Gly Gly
                35                  40                  45
Thr Cys Cys Cys Thr Gly Ala Ala Ala Cys Thr Cys Thr Cys Thr
                50                  55                  60
Gly Thr Gly Thr Ala Gly Cys Cys Thr Cys Thr Gly Gly Ala Thr Thr
65                  70                  75                  80
Cys Ala Cys Thr Thr Thr Cys Ala Gly Thr Ala Gly Cys Thr Ala Thr
                85                  90                  95
Thr Ala Cys Ala Thr Gly Thr Cys Thr Thr Gly Gly Gly Thr Thr Cys
                100                 105                 110
Gly Cys Cys Ala Gly Ala Cys Thr Cys Cys Gly Gly Ala Gly Ala Ala
                115                 120                 125
Gly Ala Gly Gly Cys Thr Gly Gly Ala Gly Thr Gly Gly Gly Thr Cys
                130                 135                 140
Gly Cys Gly Ala Cys Cys Ala Thr Ala Ala Gly Thr Gly Ala Thr Gly
145                 150                 155                 160
Gly Thr Gly Gly Thr Gly Ala Thr Ala Ala Cys Ala Cys Cys Thr Ala
                165                 170                 175
Cys Thr Ala Cys Gly Cys Ala Gly Gly Cys Ala Cys Thr Gly Thr Gly
                180                 185                 190
Ala Cys Gly Gly Gly Cys Cys Gly Ala Thr Thr Cys Ala Cys Cys Ala
                195                 200                 205
Thr Cys Thr Cys Cys Ala Gly Ala Gly Ala Cys Thr Thr Thr Gly Cys
                210                 215                 220
Cys Ala Ala Gly Ala Ala Cys Ala Cys Cys Cys Thr Gly Thr Ala Cys
225                 230                 235                 240
Cys Thr Gly Cys Ala Ala Ala Thr Gly Ala Ala Cys Ala Gly Thr Cys
                245                 250                 255
Thr Gly Ala Cys Cys Thr Cys Thr Gly Ala Gly Gly Ala Cys Ala Cys
                260                 265                 270
Ala Gly Cys Cys Gly Thr Gly Thr Ala Thr Thr Ala Cys Thr Gly Thr
                275                 280                 285
Gly Cys Ala Ala Gly Ala Ala Thr Thr Cys Ala Thr Thr Gly Gly Cys
                290                 295                 300
Cys Thr Thr Ala Cys Thr Ala Thr Thr Thr Gly Ala Cys Thr Ala Cys
305                 310                 315                 320
Cys Thr Gly Gly Gly Gly Cys Cys Ala Ala Gly Gly Cys Ala Cys Cys
                325                 330                 335
Ala Cys Thr Cys Thr Cys Ala Cys Ala Gly Thr Cys Thr Cys Cys Thr
                340                 345                 350
Cys Ala
```

<210> SEQ ID NO 55
<211> LENGTH: 106
<212> TYPE: PRT
<213> ORGANISM: Artificial
<220> FEATURE:
<223> OTHER INFORMATION: Synthetic

<400> SEQUENCE: 55

```
Gln Phe Val Leu Ser Gln Ser Pro Ala Ile Leu Ser Ala Ser Pro Gly
 1               5                  10                  15

Glu Met Leu Thr Met Thr Cys Arg Ala Ser Ser Val Ser Tyr Met
             20                  25                  30

Asn Trp Tyr Gln Gln Lys Pro Gly Ser Ser Pro Lys Pro Trp Ile Tyr
             35                  40                  45

Ala Thr Ser Asp Leu Ala Ser Gly Val Pro Ala Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Ser His Pro Pro Thr
                 85                  90                  95

Phe Gly Gly Gly Thr Lys Leu Glu Ile Arg
             100                 105

<210> SEQ ID NO 56
<211> LENGTH: 318
<212> TYPE: PRT
<213> ORGANISM: Artificial
<220> FEATURE:
<223> OTHER INFORMATION: Synthetic

<400> SEQUENCE: 56

Cys Ala Ala Thr Thr Thr Gly Thr Thr Cys Thr Cys Thr Cys Cys Cys
 1               5                  10                  15

Ala Gly Thr Cys Thr Cys Cys Ala Gly Cys Ala Ala Thr Cys Cys Thr
             20                  25                  30

Gly Thr Cys Thr Gly Cys Ala Thr Cys Thr Cys Cys Gly Gly Gly Gly
         35                  40                  45

Gly Ala Gly Ala Thr Gly Cys Thr Cys Ala Cys Ala Ala Thr Gly Ala
     50                  55                  60

Cys Thr Thr Gly Cys Ala Gly Gly Cys Cys Ala Gly Cys Thr Cys Ala
 65                  70                  75                  80

Ala Ala Gly Thr Gly Thr Ala Ala Gly Thr Thr Ala Cys Ala Thr Gly
                 85                  90                  95

Ala Ala Cys Thr Gly Gly Thr Ala Cys Ala Gly Cys Ala Gly Ala Ala
             100                 105                 110

Ala Gly Cys Cys Ala Gly Gly Ala Thr Cys Thr Thr Cys Cys Cys Cys
         115                 120                 125

Cys Ala Ala Ala Cys Cys Cys Thr Gly Gly Ala Thr Thr Thr Ala Thr
     130                 135                 140

Gly Cys Cys Ala Cys Ala Thr Cys Cys Gly Ala Cys Cys Thr Gly Gly
145                 150                 155                 160

Cys Thr Thr Cys Thr Gly Gly Ala Gly Thr Cys Cys Cys Thr Gly Cys
                 165                 170                 175

Thr Cys Gly Cys Thr Thr Cys Ala Gly Thr Gly Gly Cys Ala Gly Thr
             180                 185                 190

Gly Gly Gly Thr Cys Thr Gly Gly Gly Ala Cys Cys Thr Cys Thr Thr
         195                 200                 205

Ala Thr Thr Cys Thr Cys Thr Cys Ala Cys Ala Ala Thr Cys Ala Gly
     210                 215                 220

Cys Ala Gly Ala Gly Thr Gly Gly Ala Gly Gly Cys Thr Gly Ala Ala
225                 230                 235                 240

Gly Ala Thr Gly Cys Thr Gly Cys Cys Ala Cys Thr Thr Ala Thr Thr
                 245                 250                 255
```

```
Ala Cys Thr Gly Cys Cys Ala Gly Cys Ala Gly Thr Gly Gly Ala Gly
            260                 265                 270

Thr Ala Gly Thr Cys Ala Cys Cys Cys Ala Cys Cys Cys Ala Cys Gly
        275                 280                 285

Thr Thr Cys Gly Gly Ala Gly Gly Gly Gly Gly Ala Cys Cys Ala
        290                 295                 300

Ala Gly Cys Thr Gly Gly Ala Ala Ala Thr Ala Ala Gly Ala
305                 310                 315
```